United States Patent
Bourderioux et al.

(10) Patent No.: US 10,294,262 B2
(45) Date of Patent: *May 21, 2019

(54) 7-DEAZAPURINE NUCLEOSIDES FOR THERAPEUTIC USES

(71) Applicant: Institute of Organic Chemistry and Biochemistry ASCR, V.V.I., Prague (CZ)

(72) Inventors: Aurelie Bourderioux, Etrechy (FR); Michal Hocek, Prague (CZ); Petr Naus, Prague (CZ)

(73) Assignee: INSTITUTE OF ORGANIC CHEMISTRY AND BIOCHEMISTRY ASCR, V.V.I. (CZ)

(*) Notice: Subject to any disclaimer, the term of this patent is extended or adjusted under 35 U.S.C. 154(b) by 0 days.

This patent is subject to a terminal disclaimer.

(21) Appl. No.: 15/453,702

(22) Filed: Mar. 8, 2017

(65) Prior Publication Data

US 2017/0240584 A1 Aug. 24, 2017

Related U.S. Application Data

(63) Continuation of application No. 15/073,502, filed on Mar. 17, 2016, now Pat. No. 9,624,257, which is a continuation of application No. 14/394,262, filed as application No. PCT/CZ2010/000050 on Apr. 19, 2010, now Pat. No. 9,321,800.

(60) Provisional application No. 61/171,656, filed on Apr. 22, 2009.

(51) Int. Cl.
  *C07H 19/14* (2006.01)
  *A61K 31/7064* (2006.01)
  *A61K 45/06* (2006.01)

(52) U.S. Cl.
  CPC ......... *C07H 19/14* (2013.01); *A61K 31/7064* (2013.01); *A61K 45/06* (2013.01)

(58) Field of Classification Search
  None
  See application file for complete search history.

(56) References Cited

U.S. PATENT DOCUMENTS

| | | | |
|---|---|---|---|
| 9,321,800 B2* | 4/2016 | Bourderioux | A61K 31/7064 |
| 9,624,257 B2* | 4/2017 | Bourderioux | A61K 31/7064 |
| 2006/0079468 A1 | 4/2006 | Roberts et al. | |
| 2011/0306573 A1* | 12/2011 | Avolio | A61K 31/7064 |
| | | | 514/52 |

FOREIGN PATENT DOCUMENTS

| | | | |
|---|---|---|---|
| WO | 2005/044835 A1 | 5/2005 | |
| WO | 2010/026153 A1 | 3/2010 | |

OTHER PUBLICATIONS

Bergstrom et al., Journal of Organic Chemistry, 1991, 56, pp. 5598-5602.*
Database CA, Chemical Abstracts Service, Zhang et al.: "Studies on synthesis of derivatives of 7-deaza-adenosine and their biological activities". XP002623432. retrieved from STN Database accession No. 142:366727 and Zhongguo Yaowu Huaxue Zazhi, vol. 13, No. 2, pp. 63-66 (2003).
Schram, et al., "Pyrrolopyrimidine nucleosides VIII. synthesis of sangivamycin derivatives possessing exocyclic heterocycles at C5," *Journal of Carbohydrates, Nucleotides*, vol. 1(1), pp. 39-54 (1974).
Seela, et al., "7-Functionalized 7-deazapurine β-D and β-L-ribonucleosides related to tubercidin and 7-deazainosine: glycosylation of pyrrolo[2.3-d]pyrimidines with 1-0-acetyl-2.3.5-tri-0-benzoyl-β-D or β-L-ribofuranose," *Tetrahedron*, vol. 63(39), pp. 9850-9861 (2007).
Zhang, et al., "Study on the Synthesis and PKA-I Binding Activities of 5-Alkynyl Tubercidin Analogues," *Bioorganic & Medicinal Chemistry*, vol. 10, pp. 907-912 (2002).
International Search Report and Written Opinion for International Application No. PCT/CZ2010/000050, dated May 4, 2011, 15 pages.
Bergstrom, et al., "Palladium• Mediated Synthesis of C-5 Pyrimidine Nucleoside Thioethers from Disulfides and Mercurinucleosides," Journal of Organize Chemistry, pp. 5598-5602 (1991).

* cited by examiner

*Primary Examiner* — Traviss C McIntosh, III
(74) *Attorney, Agent, or Firm* — Mintz, Levin, Cohn, Fems, Glovsky and Popeo, P.C.

(57) ABSTRACT

The invention provides compounds of formula I, wherein $R_1$, $R_2$ and $R_3$ have values defined in the specification and a pharmaceutically acceptable salt thereof; or an optical isomer thereof; or a mixture of optical isomers, as well as compositions comprising such compounds and therapeutic methods that utilize such compounds and/or compositions.

15 Claims, 1 Drawing Sheet

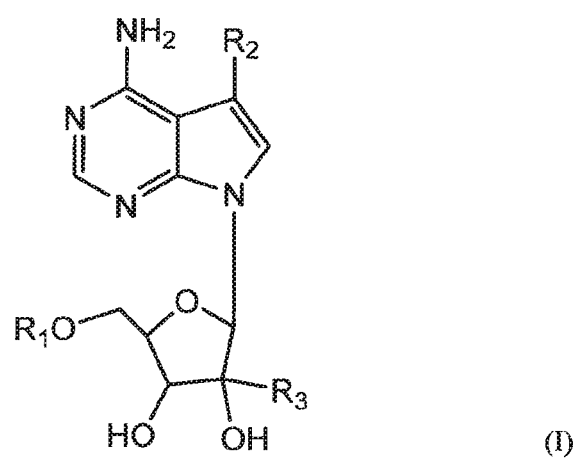
(I)

7-DEAZAPURINE NUCLEOSIDES FOR THERAPEUTIC USES

CROSS-REFERENCES TO RELATED APPLICATIONS

This application is a continuation of U.S. application Ser. No. 15/073,502, filed Mar. 17, 2016, now U.S. Pat. No. 9,624,257, which is a continuation of U.S. application Ser. No. 14/394,262, filed Feb. 19, 2015, now U.S. Pat. No. 9,321,800, the National Stage Entry of PCT Application No. PCT/CZ2010/000050, filed Apr. 19, 2010, claiming priority to U.S. Provisional Application No. 61/171,656, filed Apr. 22, 2009, each of which is incorporated by reference herein in its entirety.

BACKGROUND OF THE INVENTION

The present invention relates to novel anti-proliferation compounds and their therapeutic uses.

SUMMARY OF THE INVENTION

The present invention provides anti-cancer compounds. Accordingly, in one aspect the present invention provides a compound of the invention, which is a compound of formula I:

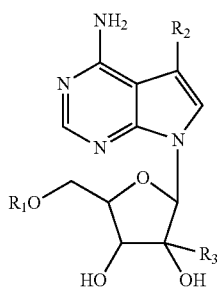

(I)

wherein:

$R_1$ is hydrogen, mono-, di-, or tri-phosphate;

$R_2$ is aryl, heteroaryl, or alkynyl, wherein said aryl is optionally substituted by one or two substituents selected from the group consisting of alkoxy, alkylthio, or halogen;

$R_3$ is hydrogen or alkyl; or a pharmaceutically acceptable salt thereof; or an optical isomer thereof; or a mixture of optical isomers.

In another aspect, the present invention provides a compound of formula (I), wherein $R_1$ is hydrogen, mono-, di-, or tri-phosphate; $R_2$ is aryl that is optionally substituted by one substituent selected from the group consisting of alkoxy, alkylthio, or halogen; $R_3$ is hydrogen; or a pharmaceutically acceptable salt thereof; or an optical isomer thereof; or a mixture of optical isomers.

In another aspect, the present invention provides a compound of formula (I), wherein $R_1$ is hydrogen, mono-, di-, or tri-phosphate; $R_2$ is aryl that is optionally substituted by one substituent selected from the group consisting of alkoxy, alkylthio, or halogen; $R_3$ is alkyl; or a pharmaceutically acceptable salt thereof; or an optical isomer thereof; or a mixture of optical isomers.

In another aspect, the present invention provides a compound of formula (I), wherein $R_1$ is hydrogen, mono-, di-, or tri-phosphate; $R_2$ is heteroaryl; $R_3$ is hydrogen, with the proviso that $R_2$ is not 1,3-oxazol-2-yl, furan-2-yl, 1,2,4-triazin-3-yl, 5, 6-dimethyl-1,2,4-triazin-3-yl, 5,6-diphenyl-1,2,4-triazin-3-yl, 1,2,4-oxadiazol-3-yl, 4H-1,2,4-triazol-3-yl, 5-thioxo-4,5-dihydro-1H-1,2,4-triazol-3-yl, 4,5-dihydro-1H-imidazol-2-yl, 4-phenylthiazol-2-yl, 1H-tetrazol-5-yl, 1,4,5,6-tetrahydropyrimidin-2-yl, or 9-oxo-9H-indeno[1,2-e][1,2,4]triazin-3-yl;

or a pharmaceutically acceptable salt thereof; or an optical isomer thereof; or a mixture of optical isomers.

In another aspect, the present invention provides a compound of formula (I), wherein $R_1$ is hydrogen, mono-, di-, or tri-phosphate; $R_2$ is heteroaryl; $R_3$ is alkyl, with the proviso that $R_2$ is not 1,3-oxazol-2-yl, furan-2-yl, 1,2,4-triazin-3-yl, 5, 6-dimethyl-1,2,4-triazin-3-yl, 5,6-diphenyl-1,2,4-triazin-3-yl, 1,2,4-oxadiazol-3-yl, 4H-1,2,4-triazol-3-yl, 5-thioxo-4,5-dihydro-1H-1,2,4-triazol-3-yl, 4,5-dihydro-1H-imidazol-2-yl, 4-phenylthiazol-2-yl, 1H-tetrazol-5-yl, 1,4,5,6-tetrahydropyrimidin-2-yl, or 9-oxo-9H-indeno[1,2-e][1,2,4]triazin-3-yl;

or a pharmaceutically acceptable salt thereof; or an optical isomer thereof; or a mixture of optical isomers.

In another aspect, the present invention provides a compound of formula (I), wherein $R_1$ is hydrogen, mono-, di-, or tri-phosphate; $R_2$ is alkynyl; $R_3$ is hydrogen; or a pharmaceutically acceptable salt thereof; or an optical isomer thereof, or a mixture of optical isomers.

The invention also provides a pharmaceutical composition comprising a compound of formula I, or a pharmaceutically acceptable salt thereof, and a pharmaceutically acceptable excipient.

The invention also provides a method of inhibiting tumor growth or cell proliferation in tumor/cancer cells in vitro or in vivo comprising contacting a subject in need of such treatment with a compound of formula I, or a pharmaceutically acceptable salt thereof.

The invention also provides a method of treating cancer in an animal comprising administering to said animal a compound of formula I, or a pharmaceutically acceptable salt thereof.

The invention also provides a method of inhibiting a neoplastic disease in an animal comprising, administering to said animal a compound of formula I, or a pharmaceutically acceptable salt thereof.

The invention also provides the use of a compound of formula I, or a pharmaceutically acceptable salt thereof, to prepare a medicament for inhibiting tumor/cancer cell growth or cell proliferation in tumor/cancer cells, slowing down cell cycle progression in tumor/cancer cells, and for treating cancer in an animal.

The invention also provides the use of a compound of formula I, or a pharmaceutically acceptable salt thereof, to prepare a medicament for inhibiting a neoplastic disease in an animal.

The invention also provides synthetic processes and synthetic intermediated disclosed herein that are useful for preparing compounds of formula (I) or salts thereof.

BRIEF DESCRIPTION OF THE DRAWINGS

FIG. 1 shows Formula I of the instant invention.

DETAILED DESCRIPTION

For purposes of interpreting this specification, the following definitions will apply and whenever appropriate, terms used in the singular will also include the plural and vice versa.

As used herein, the term "alkyl" refers to a branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. When an alkyl group includes one or more unsaturated bonds, it may be referred to as an alkenyl (double bond) or an alkynyl (triple bond) group. Furthermore, when an alkyl group is linked to an aryl group (defined below), it may be referred to as an "arylalkyl" group.

As used herein, the term "alkynyl" refers to both straight- and branched-chain hydrocarbon groups of 2 to 12 carbon atoms having one or more carbon-carbon triple bonds. Preferably the alkynyl contains 2 to 8 or 2 to 4 carbon atoms. Non-limiting examples of alkynyl includes ethynyl, propynyl, butynyl, octynyl, decynyl, and the like.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. As used herein, the term "lower alkoxy" refers to the alkoxy groups having 1-7 carbons and preferably 1-4 carbons.

The term "aryl" refers to monocyclic or bicyclic aromatic hydrocarbon groups having 6-20 carbon atoms in the ring portion. Preferably, the aryl is a ($C_6$-$C_{10}$) aryl. Non-limiting examples include phenyl, biphenyl, naphthyl or tetrahydronaphthyl, each of which may optionally be substituted by 1-4 substituents, such as optionally substituted alkyl, trifluoromethyl, cycloalkyl, halo, hydroxy, alkoxy, acyl, alkyl-C(O)—O—, aryl-O—, heteroaryl-O—, optionally substituted amino, thiol, alkylthio, arylthio, nitro, cyano, carboxy, alkyl-O—C(O)—, carbamoyl, alkylthiono, sulfonyl, sulfonamido, heterocycloalkyl and the like.

Furthermore, the term "aryl" as used herein, also refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "heteroaryl" refers to a 5-14 membered monocyclic- or bicyclic- or fused polycyclic-ring system, having 1 to 8 heteroatoms selected from N, O, S or Se. Preferably, the heteroaryl is a 5-10 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocycloalkyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinolinyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halo" or "halogen" refers to fluoro, chloro, bromo, and iodo.

As used herein, the term "isomers" refers to different compounds that have the same molecular formula. Also as used herein, the term "an optical isomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-lngold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S). The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto (e.g., phenol or hydroxyamic acid). Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences*, 20th ed., Mack Publishing Company, Easton, Pa., (1985), which is herein incorporated by reference.

As used herein, the term "pharmaceutically acceptable carrier/excipient" includes any and all solvents, dispersion media, coatings, surfactants, antioxidants, preservatives (e.g., antibacterial agents, antifungal agents), isotonic agents, absorption delaying agents, salts, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except in so far as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that inhibits or reduces proliferation of cancer cells, or inhibiting or reducing tumor/cancer growth in vitro or in vivo, or inhibiting or reducing a neoplastic disease in a subject such as a mammal. In another preferred embodiment, it also refers to the amount that reduces the primary tumor/cancer size, inhibits cancer cell infiltration into peripheral organs, slows or stops tumor metastasis, or relieves at least to some extent one or more symptoms associated with tumor or cancer, etc.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See *Dorland's Illustrated Medical Dictionary*, (W.B. Saunders Co. 27th ed. 1988).

As used herein, the term "inhibition" or "inhibiting" refers to the reduction or suppression of a given condition, symptom, or disease, or a significant decrease in the baseline activity of a biological activity or process. In one embodiment, it refers to ability to cause reduction of a tumor or cancer growth, or reduction of the tumor or cancer size.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The present invention provides anti-cancer compounds. Accordingly, in one aspect the present invention provides a compound of the invention, which is a compound of formula I:

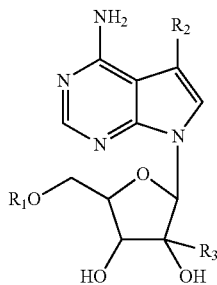

(I)

wherein:
R₁ is hydrogen, mono-, di-, or tri-phosphate;
R₂ is aryl, heteroaryl, or alkynyl, wherein said aryl is optionally substituted by one or two substituents selected from the group consisting of alkoxy, alkylthio, or halogen;
R₃ is hydrogen or alkyl; or
a pharmaceutically acceptable salt thereof; or an optical isomer thereof; or a mixture of optical isomers.

In another aspect, the present invention provides a compound of formula (I), wherein R₁ is hydrogen, mono-, di-, or tri-phosphate; R₂ is aryl that is optionally substituted by one substituent selected from the group consisting of alkoxy, alkylthio, or halogen; R₃ is hydrogen; or a pharmaceutically acceptable salt thereof; or an optical isomer thereof; or a mixture of optical isomers.

Preferably, the present invention provides a compound of formula (I), in which R₁ is hydrogen, R₂ is phenyl that is optionally substituted by one substituent selected from the group consisting of (C₁-C₄) alkoxy, (C₁-C₄) alkylthio, or halogen; R₃ is hydrogen; or a pharmaceutically acceptable salt thereof; or an optical isomer thereof; or a mixture of optical isomers.

In another aspect, the present invention provides a compound of formula (I), wherein R₁ is hydrogen, mono-, di-, or tri-phosphate; R₂ is aryl that is optionally substituted by one substituent selected from the group consisting of alkoxy, alkylthio, or halogen; R₃ is alkyl; or a pharmaceutically acceptable salt thereof; or an optical isomer thereof; or a mixture of optical isomers.

Preferably, the present invention provides a compound of formula (I), in which R₁ is hydrogen, R₂ is phenyl that is optionally substituted by one substituent selected from the group consisting of (C₁-C₄) alkoxy, (C₁-C₄) alkylthio, or halogen; R₃ is (C₁-C₄) alkyl; or a pharmaceutically acceptable salt thereof; or an optical isomer thereof; or a mixture of optical isomers.

In another aspect, the present invention provides a compound of formula (I), wherein R₁ is hydrogen, mono-, di-, or tri-phosphate; R₂ is heteroaryl; R₃ is hydrogen, with the proviso that R₂ is not 1,3-oxazol-2-yl, furan-2-yl, 1,2,4-triazin-3-yl, 5,6-dimethyl-1,2,4-triazin-3-yl, 5,6-diphenyl-1,2,4-triazin-3-yl, 1,2,4-oxadiazol-3-yl, 4H-1,2,4-triazol-3-yl, 5-thioxo-4,5-dihydro-1H-1,2,4-triazol-3-yl, 4,5-dihydro-1H-imidazol-2-yl, 4-phenylthiazol-2-yl, 1H-tetrazol-5-yl, 1,4,5,6-tetrahydropyrimidin-2-yl, or 9-oxo-9H-indeno[1,2-e][1,2,4]triazin-3-yl;

or a pharmaceutically acceptable salt thereof; or an optical isomer thereof; or a mixture of optical isomers.

Preferably, the present invention provides a compound of formula (I), in which R₁ is hydrogen, R₂ is (5-7) membered heteroaryl; R₃ is hydrogen, with the proviso that R₂ is not 1,3-oxazol-2-yl, furan-2-yl, 1,2,4-triazin-3-yl, 5,6-dimethyl-1,2,4-triazin-3-yl, 5,6-diphenyl-1,2,4-triazin-3-yl, 1,2,4-oxadiazol-3-yl, 4H-1,2,4-triazol-3-yl, 5-thioxo-4,5-dihydro-1H-1,2,4-triazol-3-yl, 4,5-dihydro-1H-imidazol-2-yl, 4-phenylthiazol-2-yl, 1H-tetrazol-5-yl, 1,4,5,6-tetrahydropyrimidin-2-yl, or 9-oxo-9H-indeno[1,2-e][1,2,4]triazin-3-yl;

or a pharmaceutically acceptable salt thereof; or an optical isomer thereof; or a mixture of optical isomers.

In another aspect, the present invention provides a compound of formula (I), wherein R₁ is hydrogen, mono-, di-, or tri-phosphate; R₂ is heteroaryl; R₃ is alkyl, with the proviso that R₂ is 1,3-oxazol-2-yl, furan-2-yl, 1,2,4-triazin-3-yl, 5,6-dimethyl-1,2,4-triazin-3-yl, 5,6-diphenyl-1,2,4-triazin-3-yl, 1,2,4-oxadiazol-3-yl, 4H-1,2,4-triazol-3-yl, 5-thioxo-4,5-dihydro-1H-1,2,4-triazol-3-yl, 4,5-dihydro-1H-imidazol-2-yl, 4-phenylthiazol-2-yl, 1H-tetrazol-5-yl, 1,4,5,6-tetrahydropyrimidin-2-yl, or 9-oxo-9H-indeno[1,2-e][1,2,4]triazin-3-yl;

or a pharmaceutically acceptable salt thereof; or an optical isomer thereof; or a mixture of optical isomers.

Preferably, the present invention provides a compound of formula (I), in which R₁ is hydrogen, R₂ is (5-7) membered heteroaryl; R₃ is (C₁-C₄) alkyl, with the proviso that R₂ is not 1,3-oxazol-2-yl, furan-2-yl, 1,2,4-triazin-3-yl, 5,6-dimethyl-1,2,4-triazin-3-yl, 5,6-diphenyl-1,2,4-triazin-3-yl, 1,2,4-oxadiazol-3-yl, 4H-1,2,4-triazol-3-yl, 5-thioxo-4,5-dihydro-1H-1,2,4-triazol-3-yl, 4,5-dihydro-1H-imidazol-2-yl, 4-phenylthiazol-2-yl, 1H-tetrazol-5-yl, 1,4,5,6-tetrahydropyrimidin-2-yl, or 9-oxo-9H-indeno[1,2-e][1,2,4]triazin-3-yl;

or a pharmaceutically acceptable salt thereof; or an optical isomer thereof; or a mixture of optical isomers.

In another aspect, the present invention provides a compound of formula (I), wherein R₁ is hydrogen, mono-, di-, or tri-phosphate; R₂ is alkynyl; R₃ is hydrogen; or a pharmaceutically acceptable salt thereof; or an optical isomer thereof; or a mixture of optical isomers. Preferably, R₁ and R₃ are hydrogen, R₂ is (C₂-C₄) alkynyl. Also preferably, R₁ and R₃ are hydrogen, R₂ is ethynyl.

In one embodiment, the present invention provides the compounds of formula (I) or a pharmaceutically acceptable salt thereof; or an optical isomer thereof; or a mixture of optical isomers, represented by the following structures:

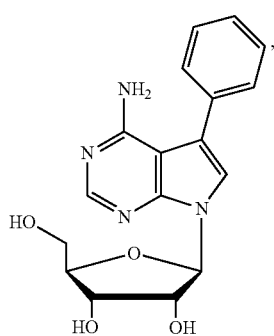

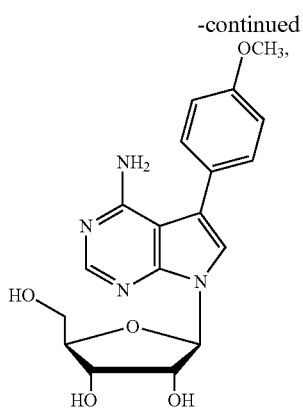
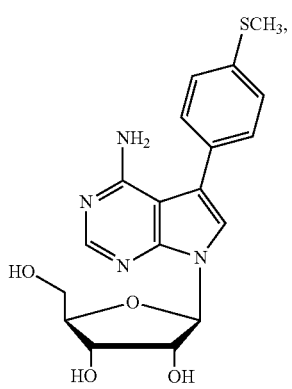
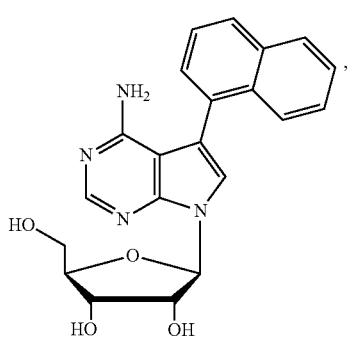
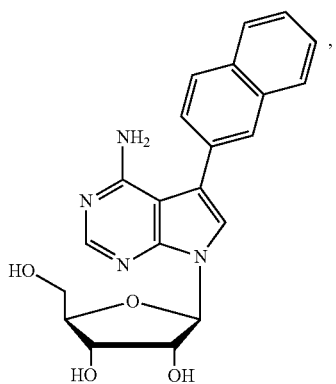
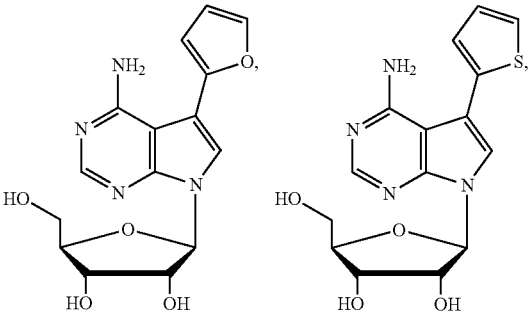
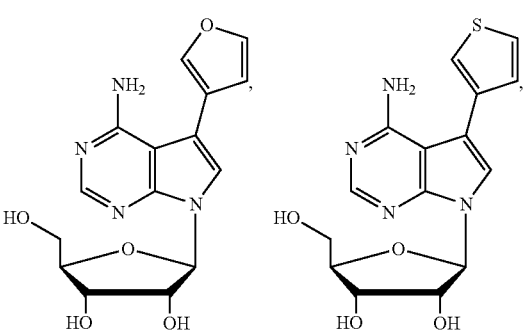
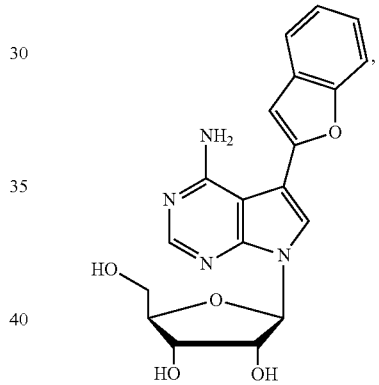
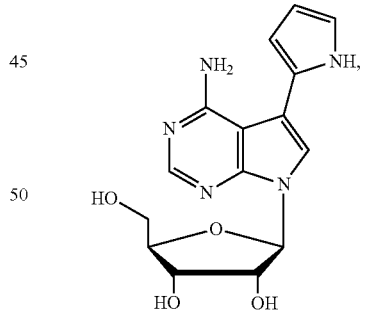
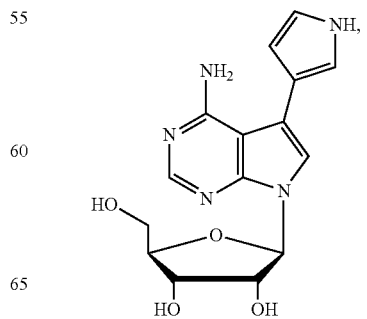

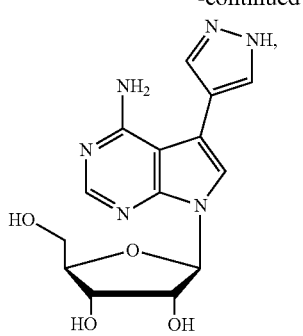
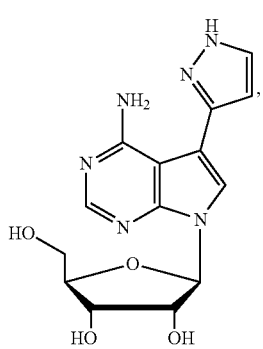
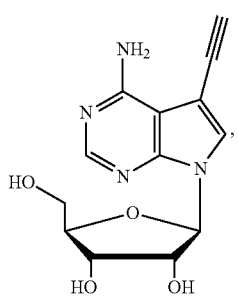
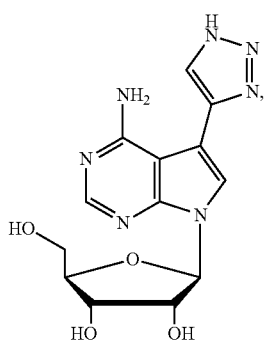
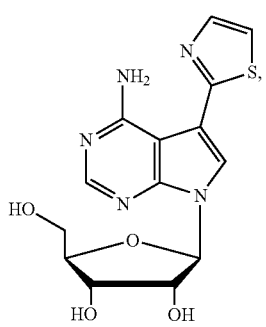
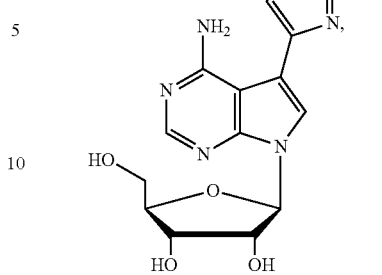
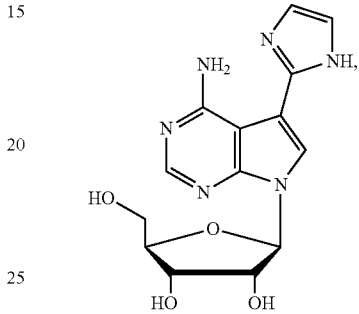
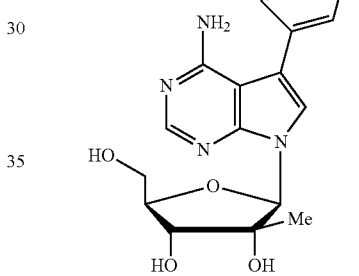
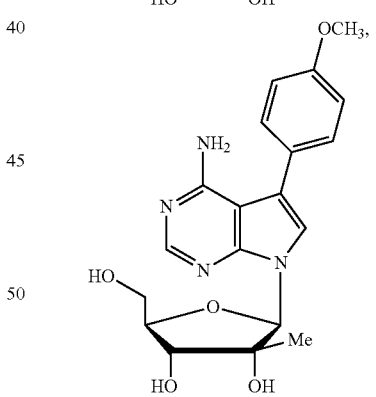
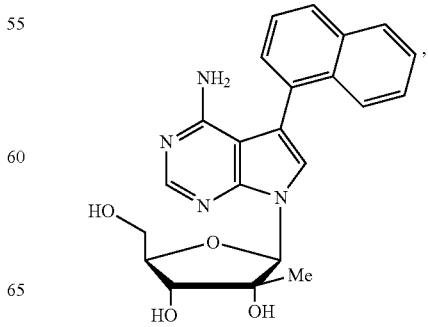

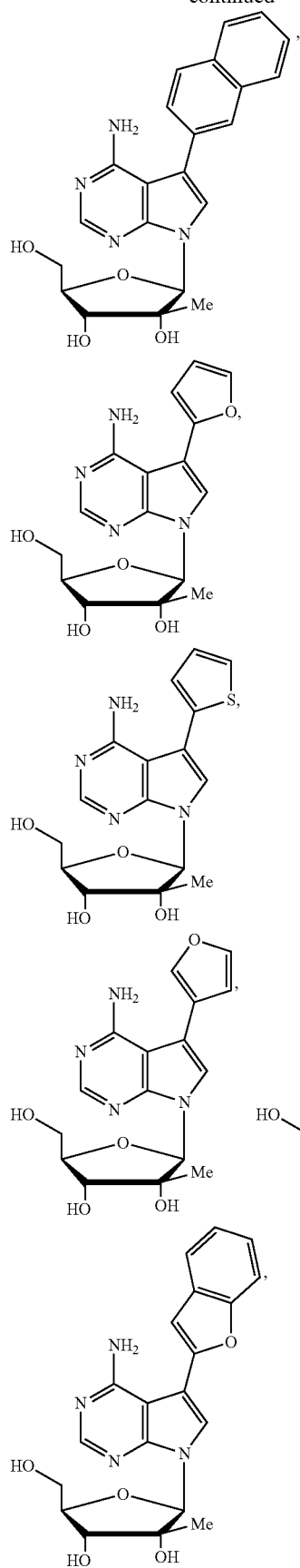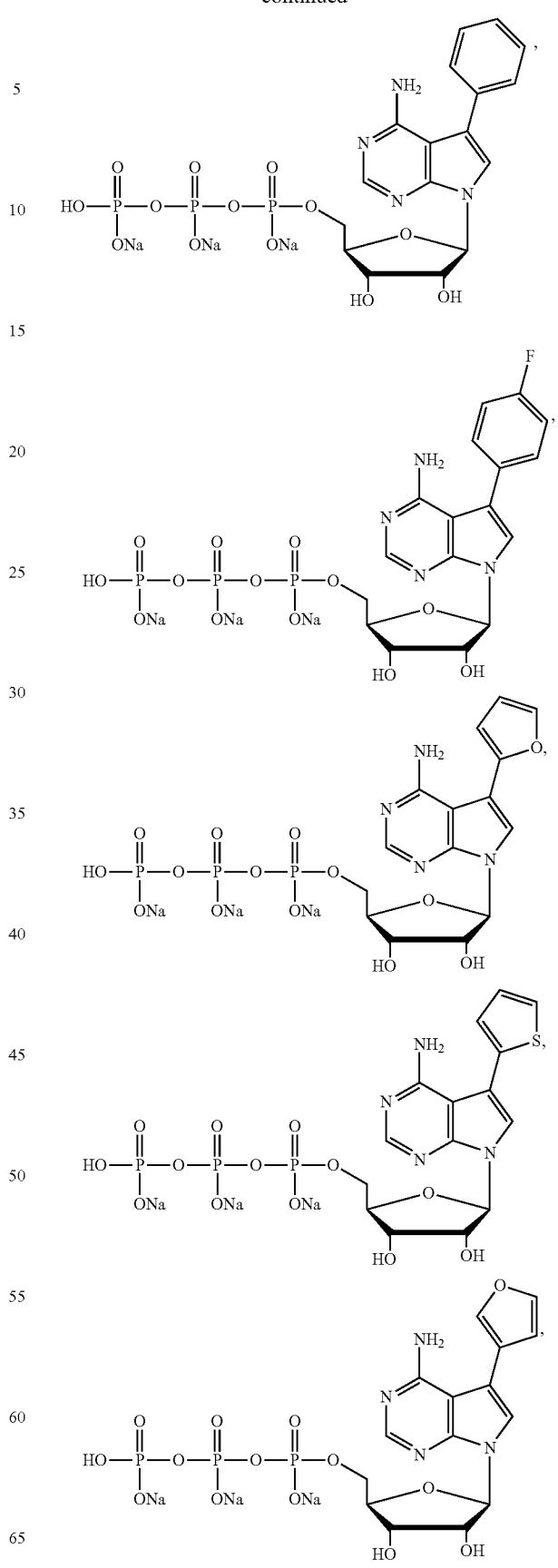

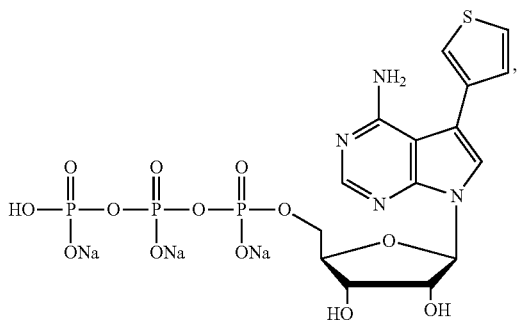

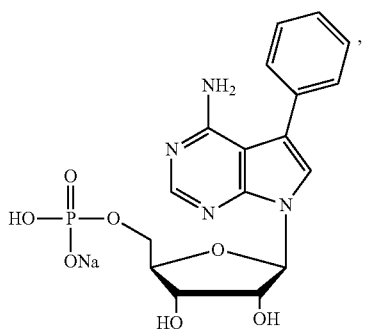

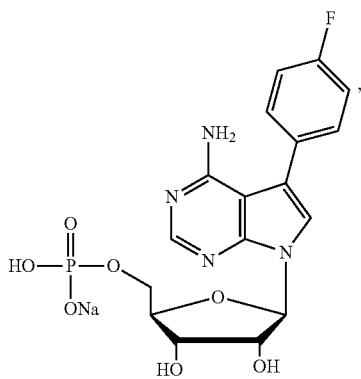

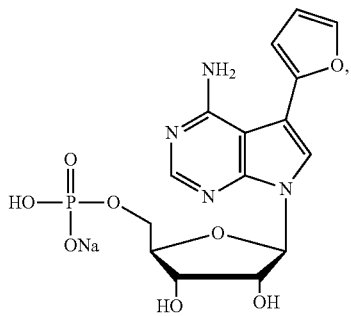

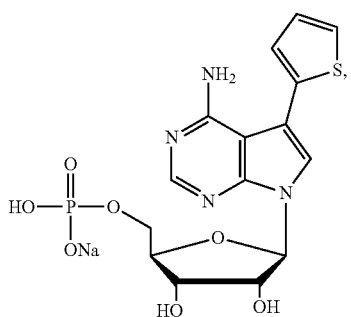

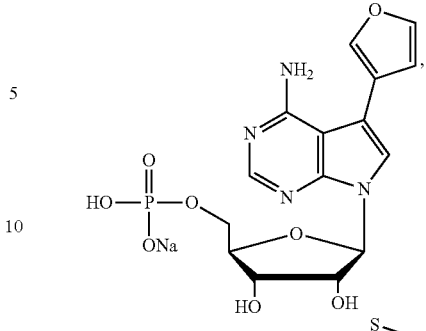

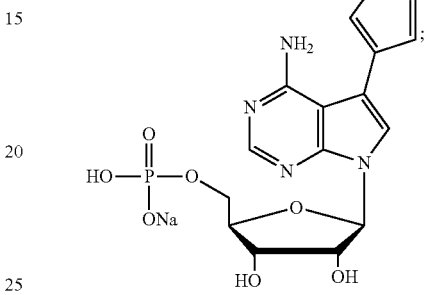

or a pharmaceutically acceptable salt thereof; or an optical isomer thereof; or a mixture of optical isomers.

The present invention provides for compounds of formula (I), pharmaceutical compositions employing such compounds comprising a pharmaceutically acceptable salts thereof, or a pharmaceutically acceptable carrier/excipient thereof, and for methods of using such compounds.

Any asymmetric carbon atom on the compounds of the present invention can be present in the (R)-, (S)- or (R,S)-configuration, preferably in the (R)- or (S)-configuration.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the hydroxamide or sulfonamide moiety may thus be employed to resolve the compounds of the present invention into their optical antipodes, e.g., by fractional crystallization of a metal (e.g., $Zn^{2+}$) complex formed with an optically active co-ligand, e.g., L-or D-histidine. Racemic products can also be resolved by chiral chromatography, e.g., high pressure liquid chromatography (HPLC) using a chiral adsorbent.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

The compounds of the present invention are useful in inhibiting tumor/cancer cell growth or cell proliferation of tumor/cancer cells, slowing down cell cycle progression in tumor/cancer cells. In addition, the compounds of the present invention are shown to induce apoptosis. Induction of apoptosis has been used as an important chemotherapy approach in treating cancer/tumor. Accordingly, the compounds of the present invention have valuable pharmaceutical properties, they can be useful as anti-proliferation and anti-tumor/anti-cancer agents.

Therefore, in one aspect, the compounds of the present invention can be used for inhibiting cell proliferation both in vitro and in vivo. In one embodiment, the compounds of the present invention can be used to inhibit cell proliferation in a tumor/cancer cell by contacting the tumor/cancer cell with an effective amount of said compounds. In one embodiment, the compounds of the present invention can be used to treat cellular proliferation diseases or conditions. Said diseases can include, but are not limited to, cancer, dysplasias, neoplasias, skin or mucosal warts, autoimmune diseases, fungal disorders, arthritis, graft rejection, inflammatory bowel disease, cellular proliferation induced after medical procedures, including, but not limited to, surgery, angioplasty, and the like.

In another aspect, the compounds of the present invention can be used for inhibiting tumor/cancer growth both in vitro and in vivo. In one embodiment, the compounds can be used for inhibiting tumor/cancer cell growth by contacting the tumor/cancer cell with an effective amount of said compounds. In one embodiment, the invention provides a method of using the compounds of the present invention for inhibiting tumor or cancer growth. Tumors or cancers that are treatable according to the methods include, for example, tumors or cancers located in the breast, lung, thyroid, lymph node, genitourinary system, kidney, ureter, bladder, ovary, testis, prostate, musculoskeletal system, bone, skeletal muscle, bone marrow, gastrointestinal tract, stomach, esophagus, small bowel, colon, rectum, pancreas, liver, smooth muscle, central or peripheral nervous system, brain, spinal cord, nerves, head, neck, ear, eye, nasopharynx, oropharynx, salivary gland, cardiovascular system, oral cavity, tongue, larynx, hypopharynx, soft tissues, skin, cervix, anus, retina, and/or heart of a mammal.

In one embodiment the invention provides a method of using the compounds of the present invention to treat a neoplastic disease, or a tumor/cancer. As used herein, the term "neoplastic disease" refers to any abnormal growth of cells or tissues being either benign (non-cancerous) or malignant (cancerous). Neoplastic diseases that are treatable according to the methods of the invention include, for example, neoplasms from acute myelogenous leukemia, chronic lymphocytic leukemia, chronic myelogenous leukemia, cutaneous T-cell lymphoma, hairy-cell leukemia and non-Hodgkin's lymphoma.

Additionally, the present invention provides:

a compound of the present invention for use as a medicament;

use of a compound of the present invention for the preparation of a medicament for inhibiting cell proliferation in tumor/cancer cells, or slowing down cell cycle progression in tumor/cancer cells;

use of a compound of the present invention for the preparation of a medicament for treating cellular proliferation diseases or conditions;

use of a compound of the present invention for the preparation of a medicament for inhibiting tumor/cancer growth both in vitro and in vivo;

use of a compound of the present invention for the preparation of a medicament for treating a neoplastic disease.

use of a compound of the present invention for the preparation of a medicament for treating a tumor or cancer.

Processes for preparing compounds of formula I are provided as further embodiments of the invention and are illustrated by the following procedures in which the meanings of the generic radicals are as given above unless otherwise qualified.

A compound of formula I can be prepared as follows.

Chemistry

Suzuki-Miyaura cross-coupling reactions of 7-iodotubericidine 1 (Scheme 1, Table 1) {for preparation, see Seela, F.; Ming, X. *Tetrahedron* 2007, 63, 9850-9861} with corresponding aryl and hetaryl boronic acids performed under Shaughnessy aqueous conditions provided desired 7-substituted-7-deazaadenosines 2a-n.

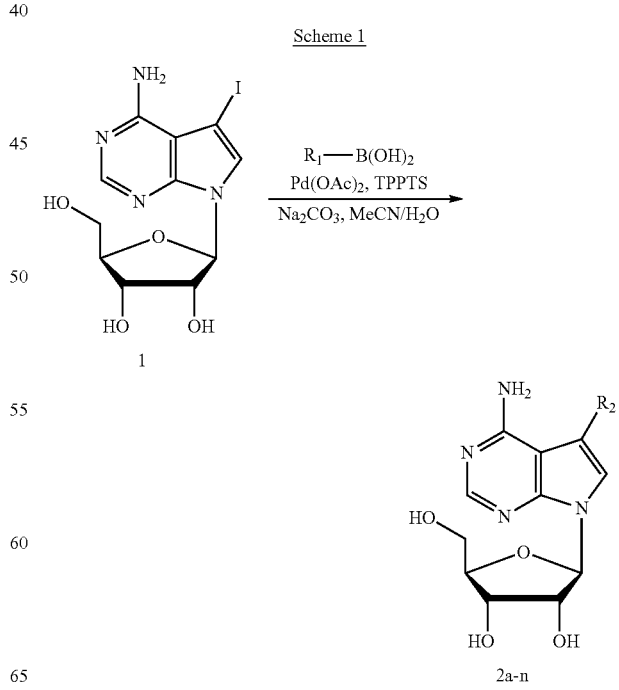

TABLE 1
Suzuki cross-coupling reactions
| Entry | R₂ | R₁B(OH)₂ | Product (yield) |
|---|---|---|---|
| 1 | 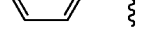 | 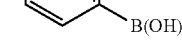 | 2a (54%) |
| 2 | 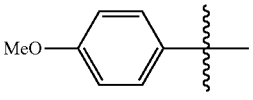 | 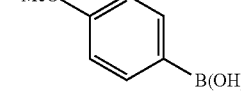 | 2b (36%) |
| 3 | 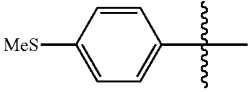 | 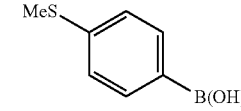 | 2c (48%) |
| 4 | 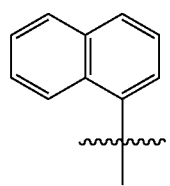 [SMILES: *c1cccc2ccccc12] | 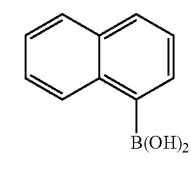 [SMILES: OB(O)c1cccc2ccccc12] | 2d (47%) |
| 5 | 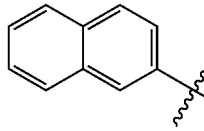 | 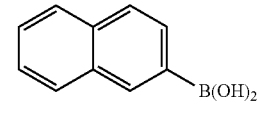 | 2e (18%) |
| 6 | 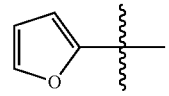 [SMILES: *c1ccco1] | 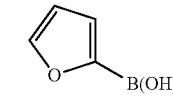 | 2f (35%) |
| 7 | 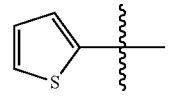 [SMILES: *c1cccs1] | 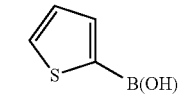 | 2g (32%) |
| 8 | 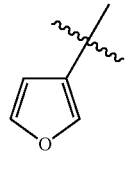 [SMILES: *c1ccoc1] | 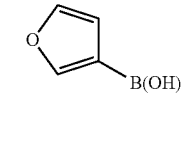 | 2h (28%) |
| 9 | 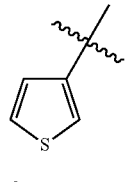 | 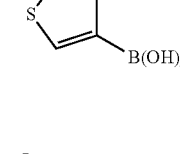 | 2i (56%) |
| 10 | 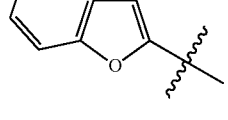 | 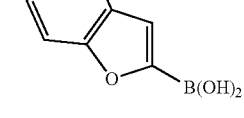 | 2j (27%) |
| 11 | 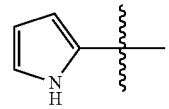 | 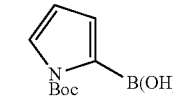 | 2k (77%) |

TABLE 1-continued

Suzuki cross-coupling reactions

| Entry | R$_2$ | R$_1$B(OH)$_2$ | Product (yield) |
|---|---|---|---|
| 12 | 3-pyrrolyl | N-triisopropylsilyl-3-pyrrolyl B(OH)$_2$ | 2l (63%) |
| 13 | 4-pyrazolyl | 4-pyrazolyl B(OH)$_2$ | 2m (9%) |
| 14 | 3-pyrazolyl | 5-pyrazolyl B(OH)$_2$ | 2n (82%) |

It should be noted that N-protecting group in both starting pyrrolyl boronic acids were removed under the conditions of coupling (entry 11, 12). Due to poor yield of Suzuki reaction (entry 13), 4-pyrazolyl derivative 2m was alternatively prepared by Stille reaction of 1 with 1-dimethylsulfamoyl-4-tributylstannylpyrazole {for preparation, see US 2004/0157892 A1} and subsequent removal of dimethylsulfamoyl group under acidic conditions (1M aq HCl) in 68% overall yield after crystallization.

Ethynyl derivative 2o was prepared by Sonogashira reaction of 1 (Scheme 2) with trimethylsilylacetylene and pro-todesilylation of TMS-ethynyl derivative 3 under basic conditions. Triazolyl derivative 2p was prepared by copper-mediated [3+2] cycloaddition of this ethynyl derivative 2o with trimethylsilyl azide {Jin, T.; Kamijo, S.; Yamamoto, Y. *Eur. J. Org. Chem.* 2004, 3789-3791}.

Scheme 2

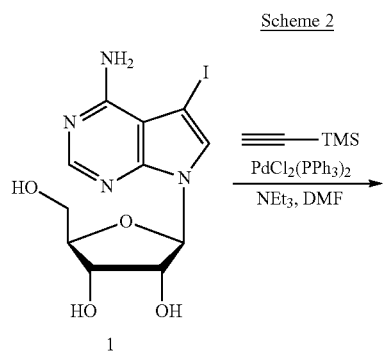

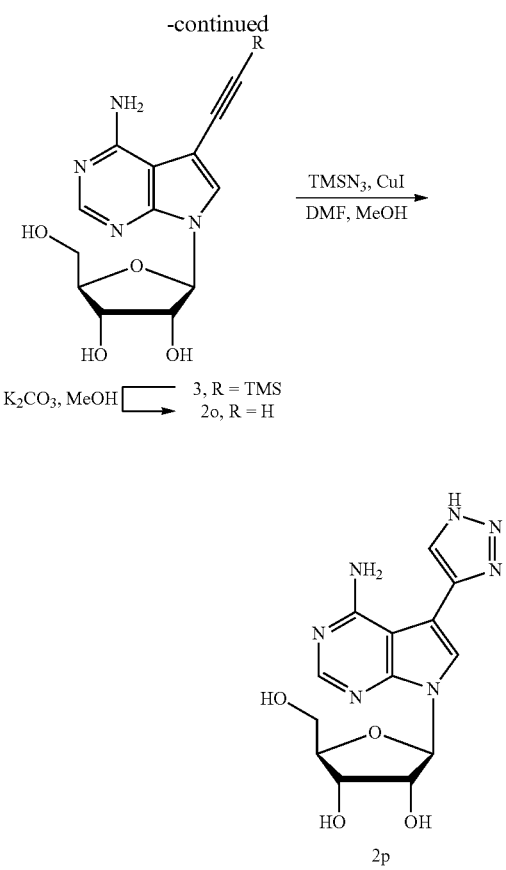

Imidazolyl and thiazolyl derivatives 2q-s were prepared by Negishi or Stille cross-coupling reactions of per-O-silylated 7-iodotubericidine 4 (Scheme 3, Table 2) with corresponding protected organometallic reagents and subsequent acidic deprotection. reactions Scheme 3

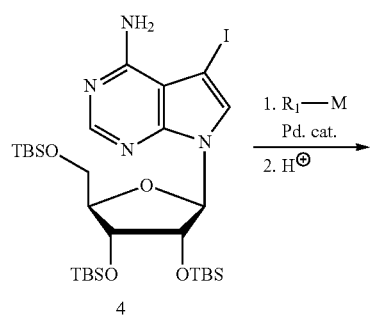

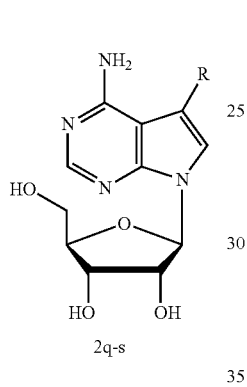

Scheme 4

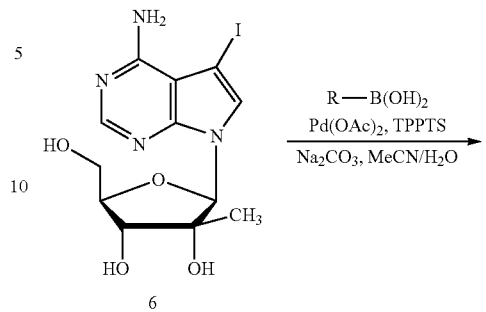

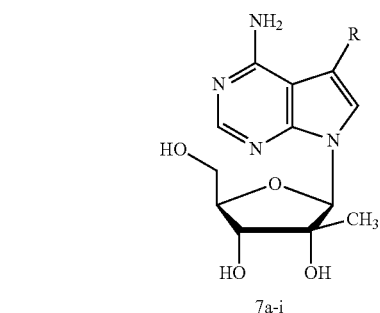

TABLE 2

Cross couplings and deprotection

| Entry | R | R₁-M | Product (Yield) |
|---|---|---|---|
| 1 | thiazol-2-yl | thiazol-2-yl-SnBu₃ | 2q (76%) |
| 2 | 1H-imidazol-4-yl | Tr-imidazol-4-yl-ZnCl | 2r (77%) |
| 3 | 1H-imidazol-2-yl | N,N-dimethylsulfamoyl-imidazol-2-yl-ZnCl | 2s (13%) |

Analogous 2'-C-methyl-7-substituted-7-deazapurine ribosides were prepared by aqueous Suzuki cross-coupling reactions of 2'-C-methyl-7-iodo-7-deazaadenosine 6 (Scheme 4) with boronic acids affording products 7a-i.

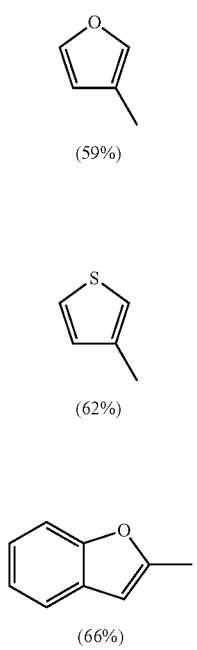

7g (59%)

7h (62%)

7i (66%)

The synthesis of required starting 2'-C-methyl riboside 6 started with acid promoted glycosylation of 6-chloro-7-iodo-7-deazapurine 8 (Scheme 5) by per-O-benzoyl-2-C-methyl-β-D-ribofuranose 9 affording protected 2'-C-methyl riboside 10 in 48% yield. Heating of compound 10 with ammonia provided desired free nucleoside 6 in 69% yield.

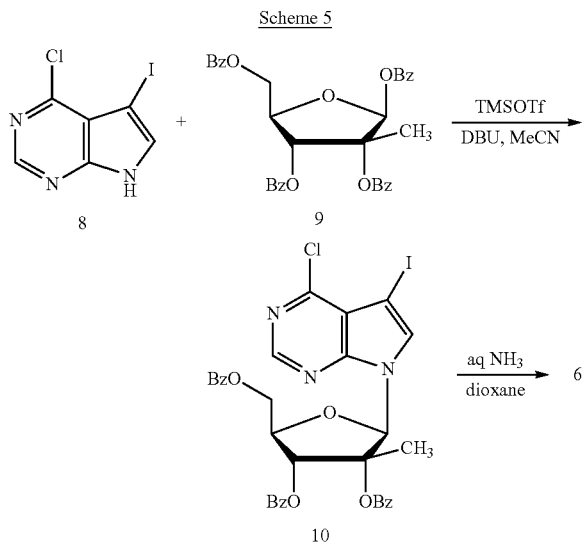

Scheme 5

For the synthesis of 7-substituted-7-deazaadenosine 5'-O-triphosphates and 5'-O-monophosphates Suzuki reactions of 7-iodo-7-deazaadenosine 5'-O-triphosphate 11 (Scheme 6, Table 3) and 5'-O-monophosphate 12 with boronic acids were carried out affording triphosphates 13a-f and monophosphates 14a-f Required starting iodo tri- and monophospahtes 11 and 12 were prepared by convenient phosphorylation of 7-iodotubericidine 1.

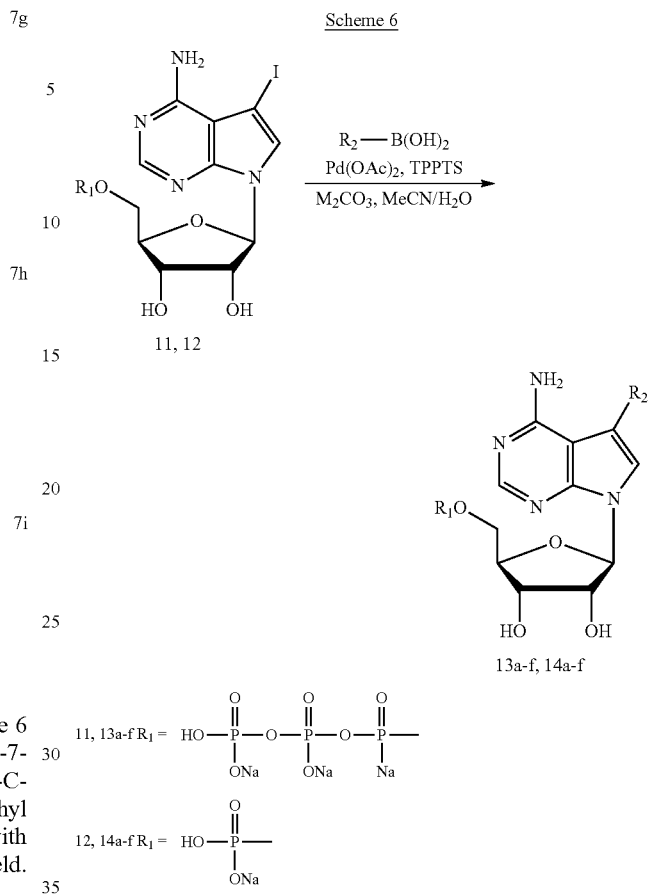

Scheme 6

TABLE 3

| | Cross-coupling reactions of 11, 12 | | |
|---|---|---|---|
| Entry | $R_2$ | Product from 11 (yield) | Product from 12 (yield) |
| 1 | phenyl | 13a (46%) | 14a (94%) |
| 2 | 4-fluorophenyl | 13b (25%) | 14b (47%) |
| 3 | 2-furyl | 13c (27%) | 14c (34%) |
| 4 | 2-thienyl | 13d (53%) | 14d (51%) |
| 5 | 3-furyl | 13e (37%) | 14e (45%) |
| 6 | 3-thienyl | 13f (67%) | 14f (47%) |

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired. Some salts may be useful as intermediates for purifying compounds of formula I or for preparing other salts.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefore and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of cancerous infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefore.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses) or against an active cancerous infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Active ingredients of the invention are also used in combination with other active ingredients. Such combinations are selected based on the condition to be treated, cross-reactivities of ingredients and pharmaco-properties of the combination. For example, when treating cancer, the compositions of the invention can be combined with other chemotherapeutic agents. The second chemotherapeutic agent can be any suitable compound that has biological activity against one or more forms of cancer.

It is also possible to combine any compound of the invention with one or more other active ingredients in a unitary dosage form for simultaneous or sequential administration to an cancer patient. The combination therapy may be administered as a simultaneous or sequential regimen. When administered sequentially, the combination may be administered in two or more administrations. Second and third active ingredients in the combination may have chemotherapeutic activity and include any of the additional chemotherapeutic agents described herein. Exemplary active ingredients to be administered in combination with compounds of the invention are described below.

Suitable additional chemotherapeutic agents include, e.g., antracyclines (e.g., doxorubicin, daunorubicin, epirubicin, idarubicin, and mitoxantrone); (b) other DNA intercalators (e.g., actinomycins C, D, B, etc.; podophyllotoxins, and epipodophyllatoxins (etoposide, teniposide, ctoposide)); (c) alkylating agents (e.g., mechlorethamine, melphalan, cyclophosphamide, chlorambucil, ifosfamide, carmustine, lomustine, busulfan, dacarbazine, cisplatin, carboplatin, oxaliplatin, iproplatin, and tetraplatin); (d) hormonal agents (e.g., antiestrogens/estrogen antagonists (tamoxifen and other SERMs); LHRH agonists and antagonists (leuprolide acetate, goserelin, abarelix); aromatase inhibitors; and antiandrogens; (e) chemoprevention agents (e.g., NSAIDs and cis-retinoids); and (f) cell-cycle chemopreventative agents.

Alternatively, the additional chemotherapeutic agent can include, e.g., antineoplasts. Representative antineoplasts include, e.g., adjuncts (e.g., levamisole, gallium nitrate, granisetron, sargramostim strontium-89 chloride, filgrastim, pilocarpine, dexrazoxane, and ondansetron); androgen inhibitors (e.g., flutamide and leuprolide acetate); antibiotic derivatives (e.g., doxorubicin, bleomycin sulfate, daunorubicin, dactinomycin, and idarubicin); antiestrogens (e.g., tamoxifen citrate, analogs thereof, and nonsteroidal antiestrogens such as toremifene, droloxifene and roloxifene); antimetabolites (e.g., fludarabine phosphate, interferon alfa-2b recombinant, methotrexate sodium, plicamycin, mercaptopurine, and thioguanine); cytotoxic agents (e.g., doxorubicin, carmustine [BCNU], lomustine [CCNU], cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozocin); hormones (e.g., medroxyprogesterone acetate, estradiol, megestrol acetate, octreotide acetate, diethylstilbestrol diphosphate, testolactone, and goserelin acetate); immunomodulators (e.g., aldesleukin); nitrogen mustard derivatives (e.g., melphalan, chlorambucil, mechlorethamine, and thiotepa) and steroids (betamethasone sodium phosphate and betamethasone acetate).

Suitable additional chemotherapeutic agents include, e.g., alkylating agents, antimitotic agents, plant alkaloids, biologicals, topoisomerase I inhibitors, topoisomerase II inhibitors, and synthetics.

Representative alkylating agents include, e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864.

Representative antimitotic agents include, e.g., allocolchicine, Halichondrin B, colchicine, colchicine derivatives, dolastatin 10, maytansine, rhizoxin, paclitaxel derivatives, paclitaxel, thiocolchicine, trityl cysteine, vinblastine sulfate, and vincristine sulfate.

Representative plant alkaloids include, e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere.

Representative biologicals include, e.g., alpha interferon, BCG, G-CSF, GM-CSF, and interleukin-2.

Representative topoisomerase I inhibitors include, e.g., camptothecin, camptothecin derivatives, and morpholinodoxorubicin.

Representative topoisomerase II inhibitors include, e.g., mitoxantron, amonafide, m-AMSA, anthrapyrazole derivatives, pyrazoloacridine, bisantrene HCL, daunorubicin, deoxydoxorubicin, menogaril, N, N-dibenzyl daunomycin, oxanthrazole, rubidazone, VM-26 and VP-16.

Representative synthetics include, e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium.

Alternatively, the additional chemotherapeutic agent can include tubulin-binding drugs and drugs that affect tubulin dynamics and function. This includes a variety of drugs that are chemically unrelated to vinca alkaloids and taxanes (e.g. CP-248 [a derivative of exisulind] and ILX-651). These drugs have distinctive effects on cells at G2M-phase and may have functionally independent effects on cells in G1 and/or S phase.

Alternatively, the additional chemotherapeutic agent can include selective apoptotic anti-cancer drugs (SAANDs), which include sulindac, aptosyn, CP-461, CP-248 and related sulindac derived compounds that inhibit one or more of the following isozymes of cyclic GMP phosphodiesterase (cGMP PDE): 1, 2, 5.

Alternatively, the additional chemotherapeutic agent can include drugs that inhibit proteosomes (bortezomib or Velcade). Proteosomes degrade many ubiquitinated proteins that have been marked for active destruction. Ubiquitinated proteins include many critical cell cycle regulatory molecules and molecules that regulate apoptosis at specific stages of the cell cycle. While proteosomes may degrade proteins throughout the cell cycle, the proteins that are degraded by proteosomes include some of the most critical cell cycle regulatory proteins. The so-called "cell cycle active rationale" may be applied to the treatment of diseases in various categories, including cancer, inflammatory/autoimmune diseases, and neurological diseases that involve disorderly cell cycle and/or apoptosis.

Alternatively, the additional chemotherapeutic agent can include drugs that inhibit heat shock protein 90 (HSP90), a 'chaperonin' that participates in the degradation of 'client' proteins in the ubiquitin mediated proteosome pathway. Several drugs seem to exert their antitumour effect by inhibiting the intrinsic ATPase activity of HSP90, resulting in degradation of HSP90 "client proteins" via the ubiquitin proteosome pathway. Examples include: geldanamycin, 17-allylamino geldanamycin, 17-demethoxygeldanamycin and radicicol.

Suitable cell-cycle dependent biological agents or schedule-dependent biological agents include drugs, proteins or other molecules that block, impede, or otherwise interfere with, cell cycle progression at the G1-phase, G1/S interface, S-phase, G2/M interface, or M-phase of the cell cycle. These drugs are cell cycle-dependent or schedule-dependent.

Specifically, suitable cell-cycle dependent biological agents or schedule-dependent biological agents include:

(1) Analogues of uridine nucleosides, analogues of thymidine nucleosides, and analogues of uridine and thymidine nucleosides. These compounds act at the S-phase in tumor cells, and possibly neovascular endothelial cells. These compounds include, e.g., 5-fluorodeoxyuridine (floxuridine, FUDR); 5-fluorouracil (5-FU); prodrugs of 5-FU (e.g. capecitabine, 5'-deoxy-5-fluorouridine, ftorafur, flucytosine); bromodeoxyuridine; and iododeoxyuridine.

(2) Modulators of fluoropyrimidines. These compounds act at the S-phase in tumor cells, and possibly neovascular endothelial cells. These compounds include, e.g., leurovorin, methotrexate and other folates; levamisole; acivicin; phosphonacetyl-L-aspartic acid (PALA); brequinar; 5-ethynyluracil; and uracil.

(3) Cytidine analogues and cytidine nucleoside analogues. These compounds act at the S-phase in tumor cells, and possibly neovascular endothelial cells. These compounds include, e.g., cytarabine (Ara-C, cytosine arabinoside); gemcitabine (2',2'-difluorodeoxycytidine); and 5-azacytidine.

(4) Purine analogues and purine nucleoside analogues. These compounds act at the S-phase in tumor cells, and possibly neovascular endothelial cells. These compounds include, e.g., 6-thioguanine; 6-mercaptopurine; azathioprine; adenosine arabinoside (Ara-A); 2',2'-difluorodeoxyguanosine; deoxycoformycin (pentostatin); cladribine (2-chlorodeoxyadenosine); and inhibitors of adenosine deaminase.

(5) Antifolates. These compounds act at the S-phase in tumor cells, and possibly neovascular endothelial cells. These compounds include, e.g., methotrexate; aminopterin; trimetrexate; edatrexate; N10-propargyl-5,8-dideazafolic acid (CB3717); ZD1694, 5,8-dideazaisofolic acid (IAHQ); 5,10-dideazatetrahydrofolic acid (DDATHF); 5-deazafolic acid (efficient substrate for FPGS); PT523 (N alpha-(4-amino-4-deoxypteroyl)-N delta-hemiphthaloyl-L-ornithine); 10-ethyl-10-deazaaminopterin (DDATHF, lomatrexol); piritrexim; 10-EDAM; ZD1694; GW1843; PDX (10-propargyl-10-deazaaminopterin); multi-targeted folate (i.e. LY231514, permetrexed); any folate-based inhibitor of thymidylate synthase (TS); any folate-based inhibitor of dihydrofolate reductase (DHFR); any folate-based inhibitor of glycinamide ribonucleotide transformylase (GARTF); any inhibitor of folylpolyglutamate synthetase (FPGS); and any folate-based inhibitor of GAR formyl transferase (AICAR transformylase).

(6) Other antimetabolites. These compounds act at the S-phase in tumor cells, and possibly neovascular endothelial cells. These compounds include, e.g., hydroxyurea and polyamines.

(7) S-phase specific radiotoxins (deoxythymidine analogues). These compounds act at the S-phase in all cells undergoing DNA synthesis. The compounds are incorporated into chromosomal DNA during S-phase. These compounds include, e.g., [125I]-iododeoxyuridine; [123I]-iododeoxyuridine; [124I]-iododeoxyuridine; [80mBr]-iododeoxyuridine; [131I]-iododeoxyuridine; and [211At]-astatine-deoxyuridine.

(8) Inhibitors of enzymes involved in deoxynucleoside/deoxynucleotide metabolism. These compounds act at the S-phase in tumor cells, and possibly neovascular endothelial cells. These compounds include, e.g., inhibitors of thymidylate synthase (TS); inhibitors of dihydrofolate reductase (DHFR); inhibitors of glycinamide ribonucleotide transformylase (GARTF); inhibitors of folylpolyglutamate synthetase (FPGS); inhibitors of GAR formyl transferase (AICAR transformylase); inhibitors of DNA polymerases (DNA Pol; e.g. aphidocolin); inhibitors of ribonucleotide reductase (RNR); inhibitors of thymidine kinase (TK); and inhibitors of topoisomerase I enzymes (e.g. camptothecins, irinotecan [CPT-11, camptosar], topotecan, NX-211 [lurtotecan], rubitecan, etc.).

(9) DNA chain-terminating nucleoside analogues. These compounds act specifically on S-phase cells and are incorporated into chromosomal DNA during S-phase; terminate growing DNA strand. These compounds include, e.g., acyclovir; abacavir; valacyclovir; zidovudine (AZT); didanosine (ddI, dideoxycytidine); zalcitabine (ddC); stavudine (D4T); lamivudine (3TC); Any 2' 3'-dideoxy nucleoside analogue; and any 2' 3'-dideoxy nucleoside analogue that terminates DNA synthesis. These compounds include, e.g., inhibitors of growth factor receptor tyrosine kinases that regulate progression through the G1-phase, G1/S interface, or S-phase of the cell cycle (e.g. EGF receptors, HER-2 neu/c-erbB2 receptor, PDGF receptors, etc; [e.g. trastusumab, iressa, erbitux, tarceva]); inhibitors of non-receptor tyrosine kinases (e.g. c-src family of tyrosine kinases; [e.g. Gleevec]); inhibitors of serine-threonine kinases that regulate progression through the G1-phase, G1/S interface or S-phase of the cell cycle (e.g. G1 cyclin-dependent kinases, G1/S cyclin-dependent kinases, and S cyclin-dependent kinases [e.g. CDK2, CDK4, CDK5, CDK6]; mitogen-activated kinases; MAP kinase signaling pathway); inhibitors of G1-phase, G1/S interface or S-phase cyclins [e.g. cyclins D1, D2, D3, E, and A]); inhibitors of G-proteins and cGMP phosphodiesterases that positively regulate cell cycle progression at the G1-phase, G1/S interface or S-phase of the cell cycle; drugs that inhibit the induction of immediate early response transcription factors (e.g. N-terminal c-jun kinase, c-myc); and drugs that inhibit proteosomes that degrade 'negative' cell cycle regulatory molecules (e.g. p53, p27/Kip1; [e.g. bortezomib]).

(10) Cytokines, growth factors, anti-angiogenic factors and other proteins that inhibit cell cycle progression at the G1-phase or G1/S interface of the cell cycle. These compounds act at G1, G1/S or S-phase of the cell cycle in tumor cells, and in some cases, neovascular endothelial cells. These compounds include, e.g., interferons; interleukins; somatostatin and somatostatin analogues (octreotide, sandostatin LAR); and many anti-angiogenic factors inhibit cell proliferation of endothelial cells at the G1 or G1/S phases of the cell cycle.

(11) Drugs and compounds that inhibit cell cycle progression at the G2/M interface, or M-phase of the cell cycle. These compounds act at G2/M interface or M-phase of the cell cycle in tumor cells, and in some cases, neovascular endothelial cells. These compounds include, e.g., (a) microtubule-targeting drugs—taxanes (e.g., taxol, taxotere, epothilones, and other taxanes and derivatives); (b) microtubule-targeting drugs—vinca alkaloids (e.g., vinblastine, vincristine, vindesine; vinflunine, vinorelbine, vinzolidine, nocadazole, and colchicines); (c) microtubule-targeting drugs—others (e.g., estramustine, CP-248 and CP-461); (d) inhibitors of serine-threonine kinases that regulate progression through the G2/M interface or M-phase of the cell cycle (e.g., inhibitors of G2/M cyclin-dependent kinases (e.g. CDC2); inhibitors of M-phase cyclins (e.g. cyclin B) and any drug that blocks, impedes, or otherwise interferes with, cell cycle progression at the G2/M interface, or M-phase of the cell cycle).

(12) Radiopharmaceuticals useful in radiation therapy and/or diagnosis. A suitable class of radioisotopes decay by a nuclear disintegration process known as the "Auger Process" or "Auger Cascade". Auger emitting isotopes generate short acting electrons that efficiently cleave duplex DNA. Suitable Auger-emitting radionuclides include, e.g., 125-Iodine, 123-Iodine and 80m-Bromine. Suitable corresponding halogenated pryimidine and purine nucleosides include, e.g., 5-125Iodo-2'-deoxyuridine, 5-123Iodo-2'-deoxyuridine, 5-80mBromo-2'-deoxyuridine and 8-80mBromo-2'-guanidine.

Growth Factors

Many growth factors and cytokines have the capacity to stimulate malignant cells to traverse specific points in the cell cycle. For example, G-CSF or GM-CSF can stimulate leukemic blasts in acute myeloid leukemia to traverse the G1/S interface. This increases the cells' susceptibility to cell-cycle specific drugs, such as cytarabine. Similar strategies have been tested using EGF and cytotoxic drugs for solid tumors. In order to respond the growth factor, cells must be at a specific stage of the cell cycle, e.g., at the G1/S interface. The continuous presence of a growth factor could be beneficial, because at any given time, only a subset of the blasts are at G1/S. Thus, the growth factors act in a cell cycle specific fashion. Similar logic can be applied to the use of hematopoietic growth factors used to treat neutropenia, anemia and thrombocytopenia.

As such, peptide/protein growth factors can be employed in the present invention to promote survival of normal non-malignant cell lineages. One benefit in using such substances is the ability to protect proliferating cells in bone marrow, skin, oral and gastrointestinal mucosa, and hair follicles.

Examples of substances within this category include, e.g., hematopoietic growth factors: G-CSF, GM-CSF, erythropoietin, thrombopoietin and biologically active derivatives of these peptides; keratinocyte growth factor (KGF) for mucositis; B-lymphocyte stimulating pepdie (BLys); platelet derived growth factor (PDGF), epithelial growth factor (EGF), TGF-alpha and related growth factors; interleukins (e.g. IL-2, IL-6); other cytokines, growth factors and peptides that stimulate proliferation of non-malignant cells that need to be protected.

Therapeutic Growth Factors/Cytokines

Some therapeutic growth factors/cytokines can inhibit cell proliferation of cancer cells and/or neovascular cells at specific stages of the cell cycle. For example, interferons, somatostatin, octreotide and analogues thereof, thrombospondin and troponin-I inhibit neovascular endothelial cell proliferation by reducing the rate at which the cells enter S-phase. As such, any one or more of these substances can be employed in the present invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Metabolites of the Compounds of the Invention

Also falling within the scope of this invention are the in vivo metabolic products of the compounds described herein. Such products may result for example from the oxidation, reduction, hydrolysis, amidation, esterification, phosphorylation and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it to cells culturing in vitro or parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-cancer activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

The anti-cancer activity of a compound may be determined using pharmacological models which are well known to the art, for example using Test A or B described below.

Test A: Cytostatic Cell Culture Assay ($CC_{50}$) for Solid Tumor Cell Lines

This assay is based on quantification of cell mass determination by a colorimetric detection of the cell associated proteins. The assay relies on the ability of sulforhodamine B (SRB) to bind to protein components of cells that have been fixed to tissue-culture plates by trichloroacetic acid (TCA). SRB is a bright-pink aminoxanthene dye with two sulfonic groups that bind to basic amino-acid residues under mild acidic conditions, and dissociate under basic conditions. As the binding of SRB is stochiometric, the amount of dye extracted from stained cells is directly proportional to the cell mass.

Cell lines: All cell lines are obtained from ATCC (Manassas, Va.). Cultivation media containing Glutamax, and trypsin are purchased from Invitrogen (Carlsbad, Calif.). Doxorubicin, Tubercidin, Clofarabine, TCA and SRB are from Sigma-Aldrich (St. Louis, Mo.). Gemcitabine is obtained from Moravek Biochemicals (Brea, Calif.)

Assay Protocol:
1. Maintain cell lines in the media listed in Table 1. Trypsinize the sub-confluent cells, count them, and adjust the cell concentrations according to the cell counts listed in Table 1.
2. Distribute the cells into the 96-well plates in 150 μL of media. Incubate the plates overnight in humidified $CO_2$ incubator at 37° C.
3. Fix one plate of each cell line with TCA. Discard the cultivation media from the plates by flicking them gently and add 100 μL cold 10% (vol/vol) TCA to each well.

Incubate the plates at 4 degree refrigerator for 1 hour. Discard TCA from the plates by flicking them gently. Rinse plates four times in a washing basin containing tap water. Store the plates at room temperature. These plates represent cell counts on day zero.
4. Prepare a set of medium solutions containing various concentrations of tested compounds by making 5-fold serial dilutions in 96-well plate. Add 50 μL of the diluted compounds per well. Include controls with untreated cells and cells treated with doxorubicin, tubercidin, clofarabine and/or gemcitabine.
5. Incubate the plates for 5 days at 37° C.
6. Fix the plates with TCA. Discard the cultivation media from the plates by flicking them gently and add 100 μL cold 10% (vol/vol) TCA to each well. Incubate the plates at 4 degree refrigerator for 1 hour. Discard TCA from the plates by flicking them gently. Rinse plates four times in a washing basin containing tap water.
7. Remove excess water by tapping the plates face down, gently on a paper towel. Allow the plates to air-dry at room temperature.
8. Add 100 μL of 0.057% SRB solution in 1% (vol/vol) acetic acid to each well of the plates fixed with TCA on day zero and five. Leave at room temperature for 30 minutes.
9. Flick the plates gently to discard SRB. Rinse the plates four times with 1% (vol/vol) Acetic Acid.
10. Store the plates at 37° incubator to facilitate faster drying.
11. Once the plates are completely dry, add 200 μL of 10 mM Tris base solution (pH 10.5) to each well. Leave at room temperature for 30 minutes for SRB to solubilize.
12. Measure the OD at 500 nm in a microplate reader.
13. Calculate the percentage of cell-growth inhibition using the next formula:

% of control cell growth=100×($OD_{sample}$−mean $OD_{day0}$)/($OD_{neg\ control}$−mean $OD_{day0}$).

For $CC_{50}$ determination, plot a dose-response curves between the compound concentration and percent of growth inhibition. $CC_{50}$ values can be derived by fitting dose-response curves using sigmoidal dose response equation.

TABLE 4

Cultivation conditions for solid tumor cell lines

| CELL LINE | Medium | Seeding Density | Dissociation Agent |
|---|---|---|---|
| HCT 116-Colon | RPMI, 10% FBS, 1X Pen/Strep | 800 cells/well | Trypsin |

TABLE 4-continued

Cultivation conditions for solid tumor cell lines

| CELL LINE | Medium | Seeding Density | Dissociation Agent |
|---|---|---|---|
| HCT 15-Colon | RPMI, 10% FBS, 1X Pen/Strep | 1600 cells/well | Trypsin |
| BT549 | RPMI, 10% FBS, 1X Pen/Strep | 4000 cells/well | Tryple Express (Invitrogen) |
| HS 578-Breast | RPMI, 10% FBS, 1X Pen/Strep | 4000 cells/well | Tryple Express (Invitrogen) |
| PC3-Prostate | F12K, 10% FBS, 1X Pen/Strep | 2500 cells/well | Trypsin |
| DU145-Prostate | MEM, 10% FBS, 1X Pen/Strep | 800 cells/well | Trypsin |
| H23-Lung | RPMI, 10% FBS, 1X Pen/Strep | 6000 cells/well | Trypsin |
| A549-Lung | RPMI, 10% FBS, 1X Pen/Strep | 1500 cells/well | Trypsin |

Test B: Cytostatic Cell Culture Assay ($CC_{50}$) for Lymphoid Tumor Cell Lines

This test is typically performed with cell lines that are derived from hematological tumors and grow in suspension. An example of such cell line is human MT-4 T-lymphoid cell line used for the determination of cytostatic activity of tested compounds. MT-4 cells were obtained from the NIH AIDS Research and Reference Reagents Program and were maintained in RPMI-1640 medium supplemented with 10% FBS and antibiotics. Cells were passaged in suspension twice a week and maintained at densities below 500,000 cells/mL. For $CC_{50}$ determination, cells were seeded into 384-well plates at 2,000 cells/well in 20 μL of culture medium. Compounds were serially diluted in culture medium and added in triplicate to a final assay volume of 40 μL/well. Plates were incubated for 5 days with tested compounds. At the end of incubation, cell viability was determined by addition of 40 μL of CellTiter Glo reagent followed by a luminescence read-out.

$CC_{50}$ values were determined as a concentration of each tested compound resulting in 50% reduction in cell viability signal. Data analysis and $CC_{50}$ value calculations were done using GraphPad Prism software (GraphPad Software, San Diego, Calif.) by applying nonlinear regression.

Representative compounds of the invention typically have activity against one or more of the above cell lines with a $CC_{50}$ of less than about 20 μM. Some representative compounds of the invention have activity against one or more of the above cell lines with a $CC_{50}$ of less than about 1 μM. Still other representative compounds of the invention have activity against one or more of the above cell lines with a $CC_{50}$ of less than about 0.1 μM.

Data for representative compounds of the invention from Tests A and B are shown in the following Table 5.

TABLE 5

| | CC50 (uM) against human tumor cell lines | | | | | | | | | |
|---|---|---|---|---|---|---|---|---|---|---|
| | Lung | | Prostate | | Colon | | Breast | | T-lymphoid | Geometric mean |
| Compound | A549 | NCI H23 | Du145 | PC3 | HCT116 | HCT15 | HS578 | BT549 | MT-4 | all |
| 4-Amino-5-(1H-imidazol-2-yl)-7-(β-D-ribofuranosyl)-7H-pyrrolo[2,3-d]pyrimidine (2s) | | 0.006 | | 0.001 | 0.002 | | 0.001 | | 0.049 | 0.0038 |

TABLE 5-continued

| | CC50 (uM) against human tumor cell lines | | | | | | | | | |
|---|---|---|---|---|---|---|---|---|---|---|
| | Lung | | Prostate | | Colon | | Breast | | T-lymphoid | Geometric mean |
| Compound | A549 | NCI H23 | Du145 | PC3 | HCT116 | HCT15 | HS578 | BT549 | MT-4 | all |
| 4-Amino-7-(β-D-ribofuranosyl)-5-(thiazol-2-yl)-7H-pyrrolo[2,3-d]pyrimidine (2q) | | 0.005 | | 0.042 | 0.093 | | 0.015 | | 0.042 | 0.0256 |
| 4-Amino-5-(1H-imidazol-4-yl)-7-(β-D-ribofuranosyl)-7H-pyrrolo[2,3-d]pyrimidine (2r) | | 0.002 | | 0.002 | 0.003 | | 0.002 | | 0.028 | 0.0038 |
| 4-Amino-5-(1H-pyrazol-3-yl)-7-beta-D-ribofuranosyl)-7H-pyrrolo[2,3-d]pyrimidine (2n) | | 0.035 | | 0.015 | 0.018 | | 0.008 | | 0.018 | 0.0171 |
| 4-Amino-7-(β-D-ribofuranosyl)-5-(1H-1,2,3-triazol-4-yl)-7H-pyrrolo[2,3-d]pyrimidine (2p) | | 0.004 | | 0.005 | 0.004 | | 0.003 | | 0.018 | 0.0052 |
| 4-Amino-5-ethynyl-7-(β-D-ribofuranosyl)-7H-pyrrolo[2,3-d]pyrimidine (2o) | | 0.001 | | 0.011 | 0.002 | | 0.001 | | 0.001 | 0.0019 |
| 4-Amino-5-(1H-pyrrol-2-yl)-7-(β-D-ribofuranosyl)-7H-pyrrolo[2,3-d]pyrimidine (2k) | 0.1604 | 0.333 | | 0.0878 | 0.0652 | | 0.1129 | 0.1292 | | 0.1283 |
| 4-Amino-5-(1H-pyrrol-3-yl)-7-(β-D-ribofuranosyl)-7H-pyrrolo[2,3-d]pyrimidine (2l) | 0.0053 | 0.033 | | 0.0290 | 0.0059 | | 0.0044 | 0.0080 | 0.024 | 0.0114 |
| 4-Amino-5-(benzofuran-2-yl)-7-(beta-D-ribofuranosyl)-7H-pyrrolo[2,3-d]pyrimidine (2j) | 7.02 | 5.40 | | 6.29 | 3.74 | | 6.73 | >10 | 4.8 | 5.5385 |
| 4-Amino-5-(1H-pyrazol-4-yl)-7-(beta-D-ribofuranosyl)-7H-pyrrolo[2,3-d]pyrimidine (2m) | 0.192 | 0.144 | | 0.014 | 0.970 | | 0.012 | 0.050 | 0.110 | 0.0819 |

TABLE 5-continued

| | CC50 (uM) against human tumor cell lines | | | | | | | | | |
|---|---|---|---|---|---|---|---|---|---|---|
| | Lung | | Prostate | | Colon | | Breast | | T-lymphoid | Geometric mean |
| Compound | A549 | NCI H23 | Du145 | PC3 | HCT116 | HCT15 | HS578 | BT549 | MT-4 | all |
| 4-Amino-7-(beta-D-ribofuranosyl)-5-(thiophen-3-yl)-7H-pyrrolo[2,3-d]pyrimidine (2i) | 0.016 | 0.073 | 0.097 | 1.323 | 0.007 | | 0.050 | 0.028 | 0.124 | 0.0607 |
| 4-Amino-5-(furan-3-yl)-7-(beta-D-ribofuranosyl)-7H-pyrrolo[2,3-d]pyrimidine (2h) | 0.034 | 0.198 | 0.330 | 0.418 | 0.015 | | 0.021 | 0.028 | 0.170 | 0.0781 |
| 4-Amino-5-(naphtalen-1-yl)-7-(beta-D-ribofuranosyl)-7H-pyrrolo[2,3-d]pyrimidine (2d) | | >10 | >10 | | >10 | | >10 | | >10 | |
| 4-Amino-5-(naphtalen-2-yl)-7-(beta-D-ribofuranosyl)-7H-pyrrolo[2,3-d]pyrimidine (2e) | | 5.35 | 1.05 | | 5.67 | | 2.16 | | | 2.8806 |
| 4-Amino-5-[4-(methylthio)phenyl]-7-(beta-D-ribofuranosyl)-7H-pyrrolo[2,3-d]pyrimidine (2c) | | 0.39 | 1.87 | | 1.29 | | 1.97 | | 4.4 | 1.5235 |
| 4-Amino-5-(4-methoxyphenyl)-7-(beta-D-ribofuranosyl)-7H-pyrrolo[2,3-d]pyrimidine (2b) | 0.701 | 0.856 | 0.152 | 1.106 | 0.633 | 0.544 | 0.811 | | 4.3 | 0.7683 |
| 4-Amino-7-(beta-D-ribofuranosyl)-5-(thiophen-2-yl)-7H-pyrrolo[2,3-d]pyrimidine (2g) | 0.0070 | 0.0037 | 0.133 | 1.62 | 0.0026 | 0.011 | 0.012 | | 0.035 | 0.0226 |
| 4-Amino-5-(furan-2-yl)-7-(beta-D-ribofuranosyl)-7H-pyrrolo[2,3-d]pyrimidine (2f) | 0.035 | 0.294 | 0.019 | 0.004 | 0.048 | 0.003 | 0.017 | | 0.086 | 0.0256 |
| Doxorubicine | 0.016 | 0.005 | | 0.021 | 0.011 | | 0.006 | 0.010 | | 0.0101 |
| Tubercidin | 0.001 | 0.011 | 0.018 | 0.048 | 0.001 | 0.011 | 0.098 | | 0.021 | 0.0103 |
| Clofarabine | 0.086 | 0.040 | 0.125 | 0.063 | 0.106 | 0.180 | 1.241 | | 0.051 | 0.1158 |
| Gemcitabine | 0.007 | 0.002 | 0.003 | 0.006 | 0.002 | 0.003 | 0.001 | 0.001 | 0.002 | 0.0024 |

Representative compounds of the invention are also found to inhibit adenosine kinase from *Mycobacterium*. Accordingly, in one embodiment, the invention also provides a method for inhibiting an adenosine kinase (e.g. an adenosine kinase from *Mycobacterium*) comprising contacting the adenosine kinase with a compound of formula I or a pharmaceutically acceptable salt thereof.

In another embodiment, the invention also provides a method for treating a disease associated with adenosine kinase activity in an animal comprising administering to an animal (e.g. a mammal such as a human) in need of such therapy, an effective adenosine kinase inhibiting amount of a compound of formula I or a pharmaceutically acceptable salt thereof. Diseases associated with adenosine kinase activity may include inflammation, sepsis, arthritis, rheumatoid arthritis, osteoarthritis, autoimmune diseases, burns, adult respiratory distress syndrome, inflammatory bowel syndrome, necrotizing enterocolitis, chronic obstructive pulmonary disease, psoriasis, conjunctivitis, iridocyclitis, ischemia, reperfusion injury, peripheral vascular disease, pancreatitis, atherosclerosis, meningitis, vasculitis, dermatitis, myositis, renal inflammation, sepsis, septicemia (e.g. endotoxemia), and septic shock (e.g. endotixic shock).

In another embodiment, the invention also provides a method for treating tuberculosis in an animal (e.g. a mammal such as a human) comprising administering a compound of formula I or a pharmaceutically acceptable salt thereof to the animal.

In another embodiment, the invention also provides the use of a compound of formula I or a pharmaceutically acceptable salt thereof to prepare a medicament for inhibiting an adenosine kinase in an animal (e.g. a mammal such as a human).

In another embodiment, the invention also provides the use of a compound of formula I or a pharmaceutically acceptable salt thereof to prepare a medicament for treating a disease associated with adenosine kinase activity in an animal (e.g. a mammal such as a human).

In another embodiment, the invention also provides the use of a compound of formula I or a pharmaceutically acceptable salt thereof to prepare a medicament for treating tuberculosis in an animal (e.g. a mammal such as a human).

Abbreviations
AcOEt ethylacetate
Boc tert-butoxycarbonyl
bd broad doublet
bs broad singlet
Bu butyl
Bz benzoyl
calcd calculated
cat. catalyst
d doublet
dd doublet of doublets
ddd doublet of doublet of doublets
DMF dimethylformamide
DMSO dimethylsulfoxide
dt doublet of triplets
Et ethyl
EDTA ethylenediaminetetraacetic acid
FAB fast atom bombardment
gem geminal
HPFC High performance flash chromatography
HR high resolution
i ipso
iPr isopropyl
IR infrared spectroscopy
m multiplet
m meta
Me methyl
MeCN acetonitrile
MeOH methanol
MeONa sodium methoxide
MS mass spectrometry
ν wave number
naphth naphthalenyl
NMR nuclear magnetic resonance
o ortho
p para
Ph phenyl
$PPh_3$ triphenylphosphine
Py pyridyl
pyrr pyrrolyl
q quartet
rel. relative
RT room temperature
s singlet
sat. saturated
sol. solution
t triplet
TBS tert-butyldimethylsilyl
td triplet of doublets
THF tetrahydrofuran
TFA trifluoroacetic acid
TPPTS sodium triphenylphosphine trisulfonate
Tr trityl, triphenylmethyl
vic vicinal The invention will now be illustrated by the following non-limiting Examples.

EXAMPLES

General methods. Melting points were determined on a Kofler block. Optical rotations were measured at 25° C., $[\alpha]_D^{20}$ values are given in $10^{-1}$ deg $cm^2$ $g^{-1}$. NMR spectra were measured at 400 MHz for $^1H$ and 100.6 MHz for $^{13}C$ nuclei, at 500 MHz for $^1H$ and 125.8 MHz for $^{13}C$, or at 600 MHz for $^1H$ and 151 MHz for $^{13}C$ in $CDCl_3$ (TMS was used as internal standard), MeOH-$d_4$ (referenced to the residual solvent signal), or DMSO-$d_6$ (referenced to the residual solvent signal). Chemical shifts are given in ppm (δ-scale), coupling constants (J) in Hz. Complete assignment of all NMR signals was performed using a combination of H,H-COSY, H,H-ROESY, H,C-HSQC and H,C-HMBC experiments. Mass spectra were measured using FAB (ionization by Xe, accelerating voltage 8 kV, glycerol+thioglycerol matrix) or ESI (electrospray). Chromatographies on reverse phase were performed on a Biotage SP1 apparatus, HPFC system with KP-C18-HS, 25+M, 35-70 mm, 90 Å or 40+M, as solid support.

Example 1

4-Amino-5-phenyl-7-(β-D-ribofuranosyl)-7H-pyrrolo[2,3-d]pyrimidine (2a)

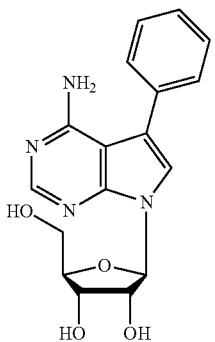

An argon purged mixture of 7-iodotubericidine 1 (200 mg, 0.51 mmol) {for preparation, see Seela, F.; Ming, X. *Tetrahedron* 2007, 63, 9850-9861}, phenylboronic acid (93 mg, 0.76 mmol), $Na_2CO_3$ (502 mg, 4.74 mmol), $Pd(OAc)_2$ (6.6 mg, 0.029 mmol) and TPPTS (42 mg, 0.07 mmol) in water/MeCN (2:1, 3.6 ml) was stirred at 80° C. for 1 h. After removal of volatiles in vacuo the residue was purified by reverse phase chromatography (0→100% MeOH in water) affording title compound 2a as white solid (94 mg, 54%). Mp 119° C. $[\alpha]^{20}_D$ −49.8 (c 0.301, MeOH). $^1H$ NMR (600 MHz, DMSO-$d_6$): 3.53 (ddd, 1H, $J_{gem}$=11.9, $J_{5'b,OH}$=6.1, $J_{5'b,4'}$=3.9, H-5'b); 3.63 (ddd, 1H, $J_{gem}$=11.9, $J_{5'a,OH}$=5.2, $J_{5'a,4'}$=3.4, H-5'a); 3.90 (ddd, 1H, $J_{4',5'}$=3.9, 3.4, $J_{4',3'}$=3.5, H-4'); 4.10 (bm, 1H, H-3'); 4.46 (bm, 1H, H-2'); 5.16 (d, 1H, $J_{OH,3'}$=3.5, OH-3'); 5.22 (dd, 1H, $J_{OH,5'}$=6.1, 5.2, OH-5'); 5.36 (d, 1H, $J_{OH,2'}$=4.8, OH-2'); 6.12 (d, 1H, $J_{1',2'}$=6.3, H-1'); 7.37 (m, 1H, H-p-Ph); 7.47 (m, 2H, H-o-Ph); 7.49 (m, 2H, H-m-Ph); 7.54 (s, 1H, H-6); 8.15 (s, 1H, H-2). $^{13}C$ NMR (151 MHz, DMSO-$d_6$): 61.93 ($CH_2$-5'); 70.89 (CH-3'); 74.05 (CH-2'); 85.38 (CH-4'); 87.27 (CH-1'); 100.73 (C-4a); 116.57 (C-5); 121.41 (C-6); 127.20 (CH-p-Ph); 128.70 (CH-o-Ph); 129.28 (CH-m-Ph); 134.71 (C-i-Ph); 151.10 (C-7a); 151.95 (CH-2); 157.57 (C-4).). IR (KBr): 3479, 3391, 1623, 1585, 1566, 1538, 1489, 1466, 1445, 1296, 1216, 1182, 1157, 1147, 1119, 1083, 1047, 1028, 1000, 798, 762, 705, 615, 503. MS (FAB) m/z 343 (M+H), 365 (M+Na). HRMS (FAB) for $C_{17}H_{19}N_4O_4$ [M+H] calcd: 343.1406; found: 343.1409. Anal. Calcd for $C_{17}H_{18}N_4O_4 \cdot 0.8H_2O$: C, 57.23; H, 5.54; N, 15.70. Found: C, 57.44; H, 5.27; N, 15.43.

Example 2

4-Amino-5-(4-methoxyphenyl)-7-(β-D-ribofuranosyl)-7H-pyrrolo[2,3-d]pyrimidine (2b)

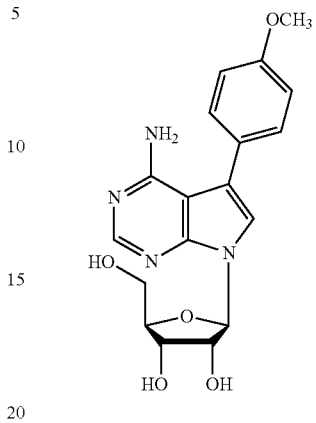

Title compound was prepared by following the procedure in Example 1. Pale yellow solid after lyophilization. Yield 36%. Mp 121° C. $[\alpha]^{20}_D$ −21.2 (c 0.304, MeOH). $^1H$ NMR (600 MHz, DMSO-$d_6$): 3.53 (ddd, 1H, $J_{gem}$=11.9, $J_{5'b,OH}$=6.3, $J_{5'b,4'}$=3.8, H-5'b); 3.62 (ddd, 1H, $J_{gem}$=11.9, $J_{5'a,OH}$=4.8, $J_{5'a,4'}$=3.8, H-5'a); 3.80 (s, 3H, $CH_3O$); 3.90 (td, 1H, $J_{4',5'}$=3.8, $J_{4',3'}$=3.1, H-4'); 4.09 (ddd, 1H, $J_{3',2'}$=5.1, $J_{3,OH}$=4.7, $J_{3',4'}$=3.1, H-3'); 4.45 (ddd, 1H, $J_{2',OH}$=6.5, $J_{2',1'}$=6.3, $J_{2',3'}$=5.1, H-2'); 5.14 (d, 1H, $J_{OH,3'}$=4.7, OH-3'); 5.22 (dd, 1H, $J_{OH,5'}$=6.3, 4.8, OH-5'); 5.33 (d, 1H, $J_{OH,2'}$=6.5, OH-2'); 6.10 (d, 1H, $J_{1',2'}$=6.3, H-1'); 7.05 (m, 2H, H-m-$C_6H_4OMe$); 7.38 (m, 2H, H-o-$C_6H_4OMe$); 7.45 (s, 1H, H-6); 8.13 (s, 1H, H-2). $^{13}C$ NMR (151 MHz, DMSO-$d_6$): 65.44 ($CH_3O$); 61.94 ($CH_2$-5'); 70.90 (CH-3'); 74.01 (CH-2'); 85.34 (CH-4'); 87.24 (CH-1'); 100.96 (C-4a); 114.70 (CH-m-$C_6H_4OMe$); 116.20 (C-5); 120.81 (CH-6); 126.85 (C-i-$C_6H_4OMe$); 129.97 (CH-o-$C_6H_4OMe$); 150.88 (C-7a); 151.86 (CH-2); 157.59 (C-4); 158.68 (C-p-$C_6H_4OMe$). IR (KBr): 3470, 3391, 2836, 1630, 1620, 1586, 1565, 1540, 1506, 1466, 1442, 1421, 1292, 1246, 1216, 1175, 1147, 1117, 1109, 1083, 1055, 1030, 838, 796, 706, 637. MS (FAB) m/z 373 (M+H), 395 (M+Na). HRMS (FAB) for $C_{18}H_{21}N_4O_5$ [M+H] calcd: 373.1512; found: 373.1498; for $C_{18}H_{20}NaN_4O_5$ [M+Na] calcd: 395.1331; found: 395.1327. Anal. Calcd for $C_{18}H_{20}N_4O_5 \cdot 0.95H_2O$: C, 55.51; H, 5.67; N, 14.38. Found: C, 55.59; H, 5.44; N, 14.04.

Example 3

4-Amino-5-[4-(methylthio)phenyl]-7-(β-D-ribofuranosyl)-7H-pyrrolo[2,3-d]pyrimidine (2c)

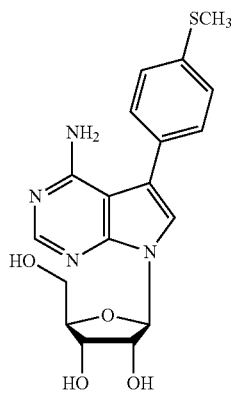

Title compound was prepared by following the procedure in Example 1. White needles after recrystallization from MeOH. Yield 48%. Mp 227-228° C. $[\alpha]^{20}{}_D$ −67.3 (c 0.237, DMSO). $^1$H NMR (500 MHz, DMSO-$d_6$): 2.52 (s, 3H, $CH_3S$); 3.53 (ddd, 1H, $J_{gem}$=12.0, $J_{5'b,OH}$=6.3, $J_{5',4'}$=3.9, H-5'b); 3.63 (ddd, 1H, $J_{gem}$=12.0, $J_{5'a,OH}$=5.1, $J_{5',4'}$=3.8, H-5'a); 3.90 (ddd, 1H, $J_{4',5'}$=3.9, 3.8, $J_{4',3'}$=3.1, H-4'); 4.10 (ddd, 1H, $J_{3',2'}$=5.1, $J_{3',OH}$=4.8, $J_{3',4'}$=3.1, H-3'); 4.45(ddd, 1H, $J_{2',OH}$=6.5, $J_{2',1'}$=6.2, $J_{2',3'}$=5.1, H-2'); 5.12 (d, 1H, $J_{OH,3'}$=4.8, OH-3'); 5.20 (dd, 1H, $J_{OH,5'}$=6.3, 5.1, OH-5'); 5.32 (d, 1H, $J_{OH,2'}$=6.5, OH-2'); 6.11 (d, 1H, $J_{1',2'}$=6.2, H-1'); 6.16 (bs, 2H, $NH_2$); 7.37 (m, 2H, H-m-$C_6H_4SMe$); 7.41 (m, 2H, H-o-$C_6H_4SMe$); 7.52 (s, 1H, H-6); 8.14 (s, 1H, H-2). $^{13}$C NMR (125.7 MHz, DMSO-$d_6$): 14.98 ($CH_3S$); 61.88 ($CH_2$-5'); 70.83 (CH-3'); 73.99 (CH-2'); 85.32 (CH-4'); 87.24 (CH-1'); 100.67 (C-4a); 116.01 (C-5); 121.25 (CH-6); 126.72 (CH-m-$C_6H_4SMe$); 129.12 (CH-o-$C_6H_4SMe$); 131.15 (C-i-$C_6H_4SMe$); 136.90 (C-p-$C_6H_4SMe$); 151.07 (C-7a); 151.90 (CH-2); 157.55 (C-4). IR (KBr): 3476, 3440, 3343, 3318, 3200, 3123, 2693, 1630, 1584, 1570, 1549, 1534, 1492, 1465, 1430, 1402, 1298, 1269, 1212, 1177, 1147, 1124, 1096, 1080, 1054, 1016, 967, 832, 796, 716, 690. MS (FAB): m/z 389 (M+H). HRMS (FAB) for $C_{18}H_{21}N_4O_4S$ [M+H] calcd: 389.1284; found: 389.1282. Anal. Calcd for $C_{18}H_{20}N_4O_4S$: C, 55.66; H, 5.19; N, 14.42. Found: C, 55.28; H, 5.25; N, 14.16.

Example 4

4-Amino-5-(naphtalen-1-yl)-7-(β-D-ribofuranosyl)-7H-pyrrolo[2,3-d]pyrimidine (2d)

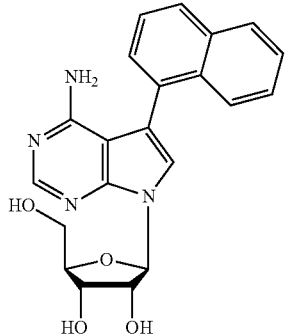

Title compound was prepared by following the procedure in Example 1. Crude product was prepurified by chromatography on silica (0→20% MeOH in $CHCl_3$) before final reverse phase chromatography. White solid after lyophilization. Yield 47%. Mp 134° C. $[\alpha]^{20}{}_D$ −56.1 (c 0.292, MeOH). $^1$H NMR (500 MHz, DMSO-$d_6$, T=353 K): 3.57 (bddd, 1H, $J_{gem}$=12.0, $J_{5'b,OH}$=5.1, $J_{5',4'}$=3.8, H-5'b); 3.67 (bdt, 1H, $J_{gem}$=12.0, $J_{5'a,OH}$=$J_{5'a,4'}$=4.0, H-5'a); 3.96 (ddd, 1H, $J_{4',5'}$=4.0, 3.8, $J_{4',3'}$=3.1, H-4'); 4.17 (bm, 1H, H-3'); 4.54 (bm, 1H, H-2'); 4.88 (bs, 1H, OH-3'); 4.95 (bdd, 1H, $J_{OH,5'}$=5.1, 4.8, OH-5'); 5.13 (bs, 1H, OH-2'); 5.43 (bs, 2H, $NH_2$); 6.19 (d, 1H, $J_{1',2'}$=5.9, H-1'); 7.49-7.53 (m, 3H, H-6 and H-2,7-naphth); 7.56 (ddd, 1H, $J_{6,5}$=8.1, $J_{6,7}$=6.9, $J_{6,8}$=1.1, H-6-naphth); 7.61 (dd, 1H, $J_{3,4}$=8.2, $J_{3,2}$=7.1, H-3-naphth); 7.81 (bd, 1H, $J_{8,7}$=8.4, H-8-naphth); 7.99 (bd, 1H, $J_{4,3}$=8.2, H-4-naphth); 8.01 (bd, 1H, $J_{5,6}$=8.1, H-5-naphth); 8.18 (s, 1H, H-2). $^{13}$C NMR (151 MHz, DMSO-$d_6$, T=353 K): 61.66 ($CH_2$-5'); 70.53 (CH-3'); 73.90 (CH-2'); 85.06 (CH-4'); 87.75 (CH-1'); 102.65 (C-4a); 113.04 (C-5); 122.03 (CH-6); 125.38 (CH-3-naphth); 125.46 (CH-8-naphth); 125.99 (CH-6-naphth); 126.38 (CH-7-naphth); 127.82 (CH-4-naphth); 128.05 (CH-2-naphth); 128.10 (CH-5-naphth); 131.55 (C-1-naphth); 132.10 (C-8a-naphth); 133.41 (C-4a-naphth); 150.43 (C-7a); 151.66 (CH-2); 157.09 (C-4). IR (KBr): 3478, 3436, 3392, 3240, 3057, 1632, 1621, 1585, 1569, 1535, 1506, 1469, 1398, 1296, 1257, 1108, 1081, 1046, 1016, 946, 849, 805, 797, 790, 779, 740. MS (FAB): m/z 393 (M+H). HRMS (FAB) for $C_{21}H_{21}N_4O_4$ [M+H] calcd: 393.1563; found: 393.1564. Anal. Calcd for $C_{21}H_{20}N_4O_4 \cdot 0.8H_2O$: C, 62.00; H, 5.35; N, 13.77. Found: C, 62.25; H, 5.21; N, 13.52.

Example 5

4-Amino-5-(naphtalen-2-yl)-7-(β-D-ribofuranosyl)-7H-pyrrolo[2,3-d]pyrimidine (2e)

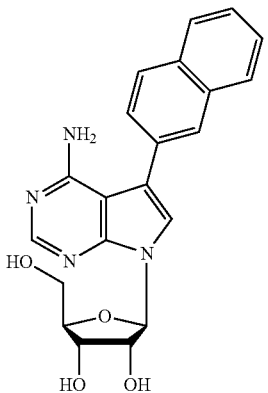

Title compound was prepared by following the procedure in Example 1. Crude product was prepurified by chromatography on silica (0→10% MeOH in $CHCl_3$) before final reverse phase chromatography. White solid after lyophilization. Yield 18%. Mp 129° C. $[\alpha]^{20}{}_D$ −59.8 (c 0.246, MeOH). $^1$H NMR (500 MHz, DMSO-$d_6$): 3.55 (ddd, 1H, $J_{gem}$=11.7, $J_{5'b,OH}$=6.2, $J_{5',4'}$=3.5, H-5'b); 3.65 (ddd, 1H, $J_{gem}$=11.7, $J_{5'a,OH}$=5.1, $J_{5'a,4'}$=3.5, H-5'a); 3.92 (q, 1H, $J_{5'a,4'}$=3.5, H-4'); 4.13 (ddd, 1H, $J_{3',2'}$=5.2, $J_{3',OH}$=4.7, $J_{3',4'}$=3.5, H-3'); 4.49 (ddd, 1H, $J_{2',OH}$=6.5, $J_{2',1'}$=6.2, $J_{2',3'}$=5.2, H-2'); 5.15 (d, 1H, $J_{OH,3'}$=4.7, OH-3'); 5.22 (dd, 1H, $J_{OH,5'}$=6.2, 5.1, OH-5'); 5.36 (d, 1H, $J_{OH,2'}$=6.5, OH-2'); 6.15 (d, 1H, $J_{1',2'}$=6.2, H-1'); 6.20 (bs, 2H, $NH_2$); 7.53 (td, 1H, $J_{6,5}$=$J_{6,7}$=8.2, $J_{6,8}$=1.4, H-6-naphth); 7.56 (td, 1H, $J_{7,6}$=$J_{7,8}$=8.2, $J_{7,6}$=1.4, H-7-naphth); 7.65 (dd, 1H, $J_{3,4}$=8.6, $J_{3,1}$=1.7, H-3-naphth); 7.66 (s, 1H, H-6); 7.97-8.00 (m, 3H, H-1,5,8-naphth); 8.03 (d, 1H, $J_{4,3}$=8.6, H-4-naphth); 8.17 (s, 1H, H-2). $^{13}$C NMR (125.7 MHz, DMSO-$d_6$): 61.86 ($CH_2$-5'); 70.77 (CH-3'); 74.00 (CH-2'); 85.29 (CH-4'); 87.32 (CH-1'); 100.83 (C-4a); 116.50 (C-5); 121.66 (CH-6); 126.06 (CH-6-naphth); 126.70 (CH-7-naphth); 126.79 (CH-1-naphth); 127.13 (CH-3-naphth); 127.79 and 127.95 (CH-5,8-naphth); 128.63 (CH-4-naphth); 132.00 and 132.10 (C-1,4a-naphth); 133.40 (C-8a-naphth); 151.20 (C-7a); 151.90 (CH-2); 157.57 (C-4). IR (KBr): 3475, 3438, 3392, 3240, 3054, 1630, 1621, 1584, 1566, 1538, 1505, 1469, 1376, 1295, 1145, 1119, 1085, 1047, 1020, 861, 824, 796, 768, 750, 624, 478. MS (FAB): m/z 393 (M+H). HRMS (FAB) for $C_{21}H_{21}N_4O_4$ [M+H] calcd: 393.1563; found: 393.1571. Anal. Calcd for $C_{21}H_{20}N_4O_4 \cdot 0.65H_2O$: C, 62.41; H, 5.31; N, 13.86. Found: C, 62.58; H, 5.18; N, 13.64.

Example 6

4-Amino-5-(furan-2-yl)-7-(β-D-ribofuranosyl)-7H-pyrrolo[2,3-d]pyrimidine (2f)

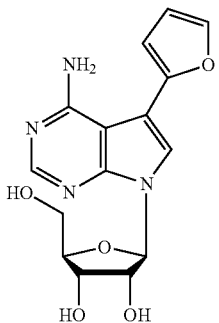

Title compound was prepared by following the procedure in Example 1. Tan solid after lyophilization. Yield 35%. Mp 118° C. $[\alpha]^{20}_D$ −52.5 (c 0.287, MeOH). $^1$H NMR (500 MHz, DMSO-$d_6$): 3.55 and 3.65 (2×dd, 2H, $J_{gem}$=11.9, $J_{5',4'}$=3.9, H-5'); 3.91 (td, 1H, $J_{4',5'}$=3.9, $J_{4',3'}$=3.4, H-4'); 4.11 (dd, 1H, $J_{3',2'}$=5.2, $J_{3',4'}$=3.4, H-3'); 4.41 (dd, 1H, $J_{2',1'}$=6.1, $J_{2',3'}$=5.2, H-2'); 5.00-5.50 (bs, 2H, OH-2',3',5'); 6.09 (d, 1H, $J_{1',2'}$=6.1, H-1'); 6.61 (dd, 1H, $J_{4,3}$=3.3, $J_{4,5}$=1.9, H-4-furyl); 6.67 (dd, 1H, $J_{3,4}$=3.3, $J_{3,5}$=0.8, H-3-furyl); 6.88 (bs, 2H, NH$_2$); 7.78 (dd, 1H, $J_{5,4}$=1.9, $J_{5,3}$=0.8, H-5-furyl); 7.83 (s, 1H, H-6); 8.13 (s, 1H, H-2). $^{13}$C NMR (125.7 MHz, DMSO-$d_6$): 61.81 (CH$_2$-5'); 70.67 (CH-3'); 74.00 (CH-2'); 85.33 (CH-4'); 87.27 (CH-1'); 99.55 (C-4a); 105.50 (CH-3-furyl); 106.34 (C-5); 112.09 (CH-4-furyl); 120.70 (CH-6); 142.16 (CH-5-furyl); 148.77 (C-2-furyl); 151.04 (C-7a); 152.26 (CH-2); 157.45 (C-4). IR (KBr): 3468, 3391, 3252, 1631, 1577, 1562, 1532, 1497, 1456, 1299, 1145, 1121, 1083, 1049, 1015, 892, 794, 550. MS (FAB): m/z 333 (M+H), 355 (M+Na). HRMS (FAB) for $C_{15}H_{17}N_4O_5$ [M+H] calcd: 333.1199; found: 333.1202. Anal. Calcd for $C_{15}H_{16}N_4O_5 \cdot 1.05H_2O$: C, 51.30; H, 5.19; N, 15.95. Found: C, 51.64; H, 5.01; N, 15.63.

Example 7

4-Amino-7-(β-D-ribofuranosyl)-5-(thiophen-2-yl)-7H-pyrrolo[2,3-d]pyrimidine (2g)

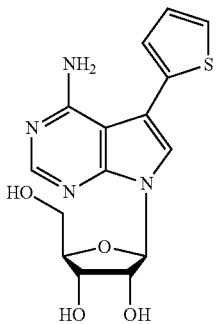

Title compound was prepared by following the procedure in Example 1. White solid after recrystallization from MeOH. Yield 32%. Mp 188° C. $[\alpha]^{20}_D$ −74.5 (c 0.235, DMSO). $^1$H NMR (500 MHz, DMSO-$d_6$): 3.54 (ddd, 1H, $J_{gem}$=12.0, $J_{5'b,OH}$=6.2, $J_{5',4'}$=3.8, H-5'b); 3.63 (ddd, 1H, $J_{gem}$=12.0, $J_{5'a,OH}$=5.0, $J_{5'a,4'}$=3.8, H-5'a); 3.91 (td, 1H, $J_{4',5'}$=3.8, $J_{4',3'}$=2.9, H-4'); 4.09 (ddd, 1H, $J_{3',2'}$=5.0, $J_{3,OH}$=4.7, $J_{3',4'}$=2.9, H-3'); 4.43 (ddd, 1H, $J_{2',OH}$=6.4, $J_{2',1'}$=6.3, $J_{2',3'}$=5.0, H-2'); 5.13 (d, 1H, $J_{OH,3'}$=4.7, OH-3'); 5.20 (dd, 1H, $J_{OH,5}$=6.2, 5.0, OH-5'); 5.34 (d, 1H, $J_{OH,2'}$=6.4, OH-2'); 6.10 (d, 1H, $J_{1',2'}$=6.3, H-1'); 6.32 (bs, 2H, NH$_2$); 7.15 (dd, 1H, $J_{3,4}$=3.5, $J_{3,5}$=1.2, H-3-thienyl); 7.18 (dd, 1H, $J_{4,5}$=5.1, $J_{4,3}$=3.5, H-4-thienyl); 7.57 (dd, 1H, $J_{5,4}$=5.1, $J_{5,3}$=1.2, H-5-thienyl); 7.62 (s, 1H, H-6); 8.15 (s, 1H, H-2). $^{13}$C NMR (125.7 MHz, DMSO-$d_6$): 61.79 (CH$_2$-5'); 70.78 (CH-3'); 74.06 (CH-2'); 85.40 (CH-4'); 87.17 (CH-1'); 100.84 (C-4a); 108.65 (C-5); 122.26 (CH-6); 126.06 (CH-5-thienyl); 126.58 (CH-3-thienyl); 128.49 (CH-4-thienyl); 135.72 (C-2-thienyl); 150.82 (C-7a); 152.22 (CH-2); 157.49 (C-4). IR (KBr): 3509, 3395, 3322, 3220, 3102, 1620, 1590, 1576, 1555, 1508, 1460, 1434, 1349, 1300, 1236, 1144, 1119, 1102, 1086, 1063, 1042, 1038, 852, 832, 793, 703, 562, 453. MS (FAB): m/z 349 (M+H). HRMS (FAB) for $C_{15}H_{17}N_4O_4S$ [M+H] calcd: 349.0971; found: 349.0965. Anal. Calcd for $C_{15}H_{16}N_4O_4S$: C, 51.71; H, 4.63; N, 16.08. Found: C, 51.33; H, 4.48; N, 15.75.

Example 8

4-Amino-5-(furan-3-yl)-7-(β-D-ribofuranosyl)-7H-pyrrolo[2,3-d]pyrimidine (2h)

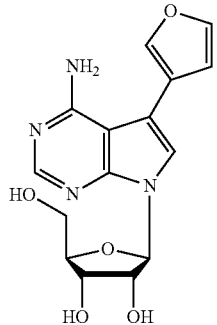

Title compound was prepared by following the procedure in Example 1. Pale yellow solid after recrystallization from MeOH. Yield 28%. Mp 190° C. $[\alpha]^{20}_D$ −56.9 (c 0.232, DMSO). $^1$H NMR (600 MHz, DMSO-$d_6$): 3.53 (ddd, 1H, $J_{gem}$=12.0, $J_{5'b,OH}$=6.2, $J_{5',4'}$=3.8, H-5'b); 3.62 (ddd, 1H, $J_{gem}$=12.0, $J_{5'a,OH}$=4.8, $J_{5'a,4'}$=3.9, H-5'a); 3.89 (ddd, 1H, $J_{4',5'}$=3.9, 3.8, $J_{4',3'}$=3.1, H-4'); 4.04 (bddd, 1H, $J_{3',OH}$=3.8, $J_{3',2'}$=3.6, $J_{3',4'}$=3.1, H-3'); 4.42 (bddd, 1H, $J_{2',1'}$=6.3, $J_{2',OH}$=5.1, $J_{2',3'}$=3.6, H-2'); 5.14 (bd, 1H, $J_{OH,3'}$=3.8, OH-3'); 5.21 (dd, 1H, $J_{2',1'}$=6.2, 4.8, OH-5'); 5.33 (bd, 1H, $J_{OH,2'}$=5.1, OH-2'); 6.08 (d, 1H, $J_{1',2'}$=6.3, H-1'); 6.27 (bs, 2H, NH$_2$); 6.70 (dd, 1H, $J_{4,5}$=1.8, $J_{4,2}$=0.9, H-4-furyl); 7.50 (s, 1H, H-6); 7.81 (dd, 1H, $J_{5,4}$=1.8, $J_{5,2}$=1.6, H-5-furyl); 7.83 (dd, 1H, $J_{2,5}$=1.6, $J_{2,4}$=0.9, H-2-furyl); 8.12 (s, 1H, H-2). $^{13}$C NMR (151 MHz, DMSO-$d_6$): 61.92 (CH$_2$-5'); 70.84 (CH-3'); 73.96 (CH-2'); 85.31 (CH-4'); 87.14 (CH-1'); 101.22 (C-4a); 106.44 (C-5); 111.75 (CH-4-furyl); 118.77 (C-3-furyl); 121.17 (CH-6); 139.86 (CH-2-furyl); 144.41 (CH-5-furyl); 150.92 (C-7a); 151.97 (CH-2); 157.70 (C-4). IR (KBr): 3512, 3394, 3296, 3252, 1623, 1582, 1561, 1504, 1457, 1364, 1306, 1286, 1245, 1152, 1121, 1109, 1067, 1038, 1021, 972, 873, 793, 777. MS (FAB): m/z 333 (M+H). HRMS (FAB) for $C_{15}H_{17}N_4O_5$ [M+H] calcd: 333.1199; found: 333.1204. Anal. Calcd for $C_{15}H_{16}N_4O_5$: C, 54.21; H, 4.85; N, 16.86. Found: C, 53.82; H, 4.85; N, 16.49.

Example 9

4-Amino-7-(β-D-ribofuranosyl)-5-(thiophen-3-yl)-7H-pyrrolo[2,3-d]pyrimidine (2i)

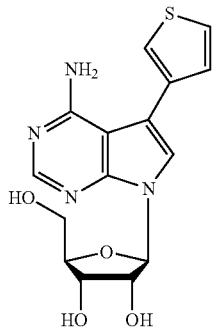

Title compound was prepared by following the procedure in Example 1. White-grey solid after recrystallization from MeOH. Yield 56%. Mp 197° C. $[α]^{20}_D$ −58.7 (c 0.237, DMSO). $^1$H NMR (600 MHz, DMSO-$d_6$): 3.53 (ddd, 1H, $J_{gem}$=12.0, $J_{5'b,OH}$=6.1, $J_{5',4'}$=3.8, H-5'b); 3.62 (ddd, 1H, $J_{gem}$=12.0, $J_{5'a,OH}$=4.9, $J_{5'a,4'}$=3.9, H-5'a); 3.90 (ddd, 1H, $J_{4,5}$=3.9, 3.8, $J_{4',3'}$=3.0, H-4'); 4.09 (bddd, 1H, $J_{3',2'}$=4.2, $J_{3,OH}$=3.2, $J_{3',4'}$=3.0, H-3'); 4.43 (bddd, 1H, $J_{2',1'}$=6.3, $J_{2',OH}$=5.1, $J_{2',3}$=4.2, H-2'); 5.14 (bd, 1H, $J_{OH,3'}$=3.2, OH-3'); 5.21 (dd, 1H, $J_{OH,5'}$=6.1, 4.9, OH-5'); 5.34 (bd, 1H, $J_{OH,2'}$=5.1, OH-2'); 6.09 (d, 1H, $J_{1',2'}$=6.3, H-1'); 6.21 (bs, 2H, NH$_2$); 7.27 (dd, 1H, $J_{4,5}$=4.9, $J_{4,2}$=1.3, H-4-thienyl); 7.52 (dd, 1H, $J_{2,5}$=2.9, $J_{2,4}$=1.3, H-2-thienyl); 7.55 (s, 1H, H-6); 7.72 (dd, 1H, $J_{5,4}$=5.1, $J_{5,2}$=2.9, H-5-thienyl); 8.13 (s, 1H, H-2). $^{13}$C NMR (151 MHz, DMSO-$d_6$): 61.90 (CH$_2$-5'); 70.84 (CH-3'); 74.00 (CH-2'); 85.32 (CH-4'); 87.17 (CH-1'); 101.00 (C-4a); 111.19 (C-5); 121.29 (CH-6); 122.24 (CH-2-thienyl); 127.62 (CH-5-thienyl); 128.71 (CH-4-thienyl); 134.94 (C-3-thienyl); 150.79 (C-7a); 151.96 (CH-2); 157.62 (C-4). IR (KBr): 3509, 3396, 3338, 3240, 3106, 1621, 1593, 1576, 1553, 1509, 1460, 1422, 1351, 1299, 1214, 1144, 1121, 1101, 1080, 1061, 1036, 856, 796, 775, 713, 562, 456. MS (FAB): m/z 349 (M+H). HRMS (FAB) for $C_{15}H_{17}N_4O_4S$ [M+H] calcd: 349.0971; found: 349.0962. Anal. Calcd for $C_{15}H_{16}N_4O_4S$: C, 51.71; H, 4.63; N, 16.08. Found: C, 51.51; H, 4.63; N, 15.76.

Example 10

4-Amino-5-(benzofuran-2-yl)-7-(β-D-ribofuranosyl)-7H-pyrrolo[2,3-d]pyrimidine (2j)

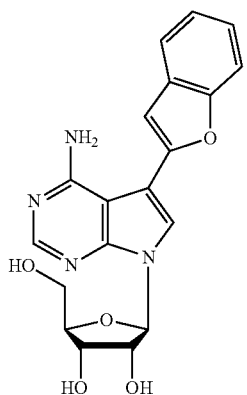

Title compound was prepared by following the procedure in Example 1. White needles after recrystallization from MeOH/water. Yield 27%. Mp 177° C. $[α]^{20}_D$ −68.8 (c 0.257, MeOH). $^1$H NMR (500 MHz, DMSO-$d_6$): 3.57 (ddd, 1H, $J_{gem}$=12.0, $J_{5'b,OH}$=6.1, $J_{5',4'}$=3.9, H-5'b); 3.67 (ddd, 1H, $J_{gem}$=12.0, $J_{5'a,OH}$=5.1, $J_{5'a,4'}$=3.9, H-5'a); 3.93 (td, 1H, $J_{4',5'}$=3.9, $J_{4,3}$=3.3, H-4'); 4.13 (ddd, 1H, $J_{3,2}$=5.1, $J_{3,OH}$=4.9, $J_{3',4'}$=3.3, H-3'); 4.46 (ddd, 1H, $J_{2',OH}$=6.3, $J_{2',1'}$=6.1, $J_{2',3}$=5.1, H-2'); 5.17 (d, 1H, $J_{OH,3}$=4.9, OH-3'); 5.23 (dd, 1H, $J_{OH,5}$=6.1, 5.1, OH-5'); 5.40 (d, 1H, $J_{OH,2}$=6.3, OH-2'); 6.14 (d, 1H, $J_{1',2'}$=6.1, H-1'); 7.00 (bs, 2H, NH$_2$); 7.13 (d, 1H, $J_{3,7}$=1.0, H-3-benzofuryl); 7.28 (td, 1H, $J_{5,4}$=$J_{5,6}$=7.3, $J_{5,7}$=1.5, H-5-benzofuryl); 7.30 (td, 1H, $J_{6,5}$=$J_{6,7}$=7.3, $J_{6,4}$=1.7, H-6-benzofuryl); 7.62-7.69 (m, 2H, H-4,7-benzofuryl); 8.11 (s, 1H, H-6); 8.18 (s, 1H, H-2). $^{13}$C NMR (125.7 MHz, DMSO-$d_6$): 61.79 (CH$_2$-5'); 70.70 (CH-3'); 74.12 (CH-2'); 85.46 (CH-4'); 87.35 (CH-1'); 99.62 (C-4a); 101.83 (CH-3-benzofuryl); 105.72 (C-5); 111.30 (CH-7-benzofuryl); 120.84 (CH-4-benzofuryl); 122.94 (CH-6); 123.69 (CH-5-benzofuryl); 124.07 (CH-6-benzofuryl); 129.02 (C-3a-benzofuryl); 151.29 (C-2-benzofuryl); 151.35 (C-7a); 152.52 (CH-2); 153.99 (C-7a-benzofuryl); 157.52 (C-4). IR (KBr): 3498, 3473, 3462, 3379, 3328, 3234, 3197, 3118, 2700, 1639, 1628, 1614, 1576, 1558, 1525, 1483, 1474, 1456, 1303, 1262, 1186, 1145, 1127, 1108, 1085, 1056, 1010, 884, 806, 792, 785, 746. MS (ESI): m/z 383 (M+H). HRMS (ESI) for $C_{19}H_{19}N_4O_5$ [M+H] calcd: 383.1350; found: 383.1348. Anal. Calcd for $C_{19}H_{18}N_4O_5 \cdot 0.6H_2O$: C, 58.04; H, 4.92; N, 14.25. Found: C, 57.78; H, 4.56; N, 14.16.

Example 11

4-Amino-5-(1H-pyrrol-2-yl)-7-(β-D-ribofuranosyl)-7H-pyrrolo[2,3-d]pyrimidine (2k)

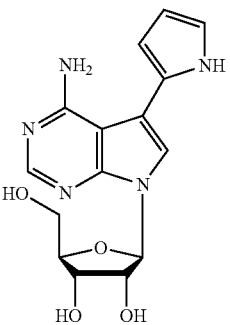

An argon purged mixture of 7-iodotubericidine 1 (196 mg, 0.50 mmol), 1-N-(Boc)-pyrrole-2-boronic acid (126 mg, 0.60 mmol), Na$_2$CO$_3$ (160 mg, 1.5 mmol), Pd(OAc)$_2$ (5.6 mg, 0.025 mmol) and TPPTS (36 mg, 0.06 mmol) in water/MeCN (2:1, 3 ml) was stirred at 100° C. for 3 h. After cooling the mixture was neutralized by the addition of aq HCl (1M), volatiles were removed in vacuo and the residue was purified by reverse phase chromatography (0→100% MeOH in water) affording title compound 2k as greenish solid (127 mg, 77%). Compound was recrystallized from MeOH as white solid, after decolorization with active carbon. Mp 205-207° C. $[α]_D$ −80.5 (c 0.205, DMSO). $^1$H NMR (500.0 MHz, DMSO-$d_6$): 3.54 (ddd, 1H, $J_{gem}$=11.9, $J_{5'b,OH}$=6.2, $J_{5'b,4'}$=3.9, H-5'b); 3.62 (dd, 1H, $J_{gem}$=11.9, $J_{5'a,OH}$=5.0, $J_{5'a,4'}$=3.9, H-5'a); 3.90 (td, 1H, $J_{4',5'}$=3.9, $J_{4',3'}$=3.1, H-4'); 4.09 (ddd, 1H, $J_{3,2}$=5.1, $J_{3',OH}$=4.8, $J_{3',4'}$=3.1, H-3'); 4.41 (ddd, 1H, $J_{2',OH}$=6.5, $J_{2',1'}$=6.3, $J_{2',3'}$=5.1, H-2'); 5.17 (d, 1H, $J_{OH,3'}$=4.8, OH-3'); 5.20 (dd, 1H, $J_{OH,5'}$=6.2, 5.0, OH-5'); 5.33 (d, 1H, $J_{OH,2'}$=6.5, OH-5'); 6.09 (d, 1H, $J_{1',2'}$=6.3, H-1'); 6.13 (ddd, 1H, $J_{3,4}$=3.3, $J_{3,NH}$=2.4, $J_{3,5}$=1.5, H-3-pyrr); 6.16 (ddd, 1H, $J_{4,3}$=3.3, $J_{4,5}$=2.7, $J_{4,NH}$=2.4, H-4-pyrr); 6.32 (bs, 2H, NH$_2$); 6.85 (td, 1H, $J_{5,4}$=$J_{5,NH}$=2.7, $J_{5,3}$=1.5, H-5-pyrr); 7.43 (s, 1H, H-6); 8.12 (s, 1H, H-2); 11.14 (bs, 1H, NH-pyrr). $^{13}$C NMR (125.7 MHz, DMSO-d$_6$): 62.00 (CH$_2$-5'); 70.92 (CH-3'); 74.11 (CH-2'); 85.30 (CH-4'); 87.20 (CH-1'); 101.09 (C-4a); 107.34 (CH-3-pyrr); 108.68 (C-5); 109.06 (CH-4-pyrr); 118.77 (CH-5-pyrr); 120.55 (CH-6); 124.69 (C-2-pyrr); 150.35 (C-7a); 151.98 (CH-2); 157.62 (C-4). MS (ESI) m/z 332 (M+H), 354 (M+Na). HRMS (ESI) for C$_{15}$H$_{18}$N$_5$O$_4$ [M+H] calcd: 332.1353; found: 332.1354. Anal. Calcd for C$_{15}$H$_{17}$N$_5$O$_4$·⅓H$_2$O: C, 53.41; H, 5.28; N, 20.76. Found: C, 53.32; H, 5.16; N, 20.57.

Example 12

4-Amino-5-(1H-pyrrol-3-yl)-7-(β-D-ribofuranosyl)-7H-pyrrolo[2,3-d]pyrimidine (2l)

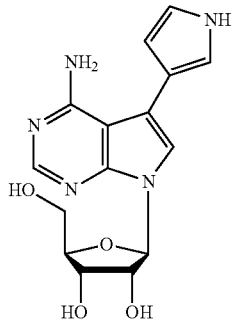

An argon purged mixture of 7-iodotubericidine 1 (893 mg, 2.28 mmol), 1-(triisopropylsilyl)-1H-pyrrole-3-boronic acid (822 mg, 3.08 mmol), Na$_2$CO$_3$ (724 mg, 6.83 mmol), Pd(OAc)$_2$ (26 mg, 0.12 mmol) and TPPTS (162 mg, 0.28 mmol) in water/MeCN (2:1, 18 ml) was stirred at 100° C. for 18 h. After cooling the mixture was neutralized by the addition of aq HCl (1M) and desalted by reverse phase chromatography (0→100% MeOH in water) affording crude product contaminated by starting iodide. Re-purification by column chromatography on silica (6% MeOH in CHCl$_3$) afforded title compound 2l as white solid (480 mg, 63%). Compound was recrystallized from EtOH. Mp 188-190° C. [α]$_D$ −59.8 (c 0.276, DMSO). $^1$H NMR (500.0 MHz, DMSO-d$_6$): 3.52 (ddd, 1H, $J_{gem}$=12.0, $J_{5'b,OH}$=6.3, $J_{5'b,4'}$=3.8, H-5'b); 3.61 (dd, 1H, $J_{gem}$=12.0, $J_{5'a,OH}$=4.9, $J_{5'a,4'}$=3.8, H-5'a); 3.88 (td, 1H, $J_{4,5}$=3.8, $J_{4',3'}$=3.0, H-4'); 4.08 (ddd, 1H, $J_{3',2'}$=5.1, $J_{3',OH}$=4.7, $J_{3',4'}$=3.0, H-3'); 4.43 (ddd, 1H, $J_{2',OH}$=6.5, $J_{2',1'}$=6.4, $J_{2',3'}$=5.1, H-2'); 5.11 (d, 1H, $J_{OH,3'}$=4.7, OH-3'); 5.24 (dd, 1H, $J_{OH,5'}$=6.3, 4.9, OH-5'); 5.30 (d, 1H, $J_{OH,2'}$=6.5, OH-5'); 6.06 (d, 1H, $J_{1',2'}$=6.4, H-1'); 6.18 (td, 1H, $J_{4,5}$=$J_{4,NH}$=2.6, $J_{4,2}$=1.6, H-4-pyrr); 6.26 (bs, 2H, NH$_2$); 6.88 (dt, 1H, $J_{2,NH}$=2.6, $J_{2,4}$=$J_{2,5}$=1.6, H-2-pyrr); 6.90 (td, 1H, $J_{5,4}$=$J_{5,NH}$=2.6, $J_{5,2}$=1.6, H-5-pyrr); 7.27 (s, 1H, H-6); 8.08 (s, 1H, H-2); 11.03 (bs, 1H, NH-pyrr). $^{13}$C NMR (125.7 MHz, DMSO-d$_6$): 62.00 (CH$_2$-5'); 70.94 (CH-3'); 73.89 (CH-2'); 85.23 (CH-4'); 87.12 (CH-1'); 101.65 (C-4a); 108.29 (CH-4-pyrr); 111.17 (C-5); 115.87 (C-3-pyrr); 116.44 (CH-2-pyrr); 119.33 (CH-2-pyrr); 119.65 (CH-6); 150.42 (C-7a); 151.62 (CH-2); 157.77 (C-4). MS (ESI) m/z 332 (M+H), 354 (M+Na). HRMS (ESI) for C$_{15}$H$_{18}$N$_5$O$_4$ [M+H] calcd: 332.1353; found: 332.1354. Anal. Calcd for C$_{15}$H$_{17}$N$_5$O$_4$·0.8H$_2$O: C, 52.11; H, 5.42; N, 20.26. Found: C, 52.32; H, 5.32; N, 20.03.

Example 13

4-Amino-5-(1H-pyrazol-4-yl)-7-(β-D-ribofuranosyl)-7H-pyrrolo[2,3-d]pyrimidine (2m)

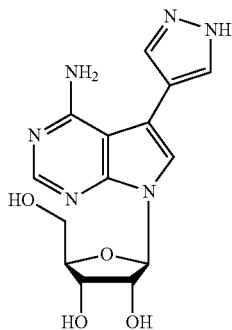

Method A. Title compound was prepared by following the procedure in Example 1. White solid. Yield 9%. Mp 156° C. $^1$H NMR (500 MHz, DMSO-d$_6$+DCl): 3.53 and 3.61 (2×dd, 2×1H, $J_{gem}$=11.9, $J_{5',4'}$=3.8, H-5'); 3.93 (td, 1H, $J_{4,5}$=3.8, $J_{4',3'}$=3.3, H-4'); 4.10 (dd, 1H, $J_{3,2}$=4.9, $J_{3',4'}$=3.3, H-3'); 4.35 (dd, 1H, $J_{2',1'}$=6.1, $J_{2',3'}$=4.9, H-2'); 6.15 (d, 1H, $J_{1',2'}$=6.1, H-1'); 7.85 (s, 1H, H-6); 8.09 (s, 2H, H-3,5-pyrazole); 8.52 (s, 1H, H-2). $^{13}$C NMR (125.7 MHz, DMSO-d$_6$+DCl): 61.52 (CH$_2$-5'); 70.72 (CH-3'); 74.83 (CH-2'); 85.97 (CH-4'); 87.14 (CH-1'); 99.99 (C-4a); 109.14 (C-4-pyrazole); 112.19 (C-5); 124.02 (CH-6); 133.06 (CH-3,5-pyrazole); 142.88 (CH-2); 148.10 (C-7a); 151.41 (C-4). IR (KBr): 3468, 3338, 3239, 3200, 3115, 1740, 1629, 1583, 1559, 1523, 1469, 1306, 1123, 1076, 1044, 1024, 796. MS (ESI): m/z 333 (M+H), 355 (M+Na). HRMS (ESI) for C$_{14}$H$_{17}$N$_6$O$_4$ [M+H] calcd: 333.1306; found: 333.1304.

Method B. An argon purged mixture of 7-iodotubericidine 1 (1.649 g, 4.2 mmol), 1-dimethylsulfamoyl-4-tributylstannylpyrazole {for preparation, see US 2004/0157892 A1} (2.97 g, 6.4 mmol), PdCl$_2$(PPh$_3$)$_2$ (148 mg, 0.21 mmol) in DMF (15 ml) was stirred at 100° C. for 3 h. Volatiles were removed under reduced pressure, the residue was several times co-evaporated with toluene/MeOH and finally with silica. Collumn chromatography on silica (0→8% MeOH in CHCl$_3$) afforded product protected on pyrazole nitrogen by dimethylsulfamoyl group (1.459 g, 79%). This material was directly deprotected by addition of aq HCl (1M, 20 ml) and stirring at 100° C. for 3 h. Volatiles were removed in vacuo, and the residue was co-evaporated with water (10-15×), once with aq ammonia (25% w/w) and again with water (6×). Re-crystallization from water afforded title compound 2m as white needles (707 mg, 64% yield of deprotection step). Mother liquors were purified by reverse phase chromatography (0→100% MeOH in water) affording after crystallization from MeOH/water additional portion of title compound (243 mg, 22% yield of deprotection step). Overall yield (coupling+deprotection) is 68%.

Example 14

4-Amino-5-(1H-pyrazol-3-yl)-7-(β-D-ribofuranosyl)-7H-pyrrolo[2,3-d]pyrimidine (2n)

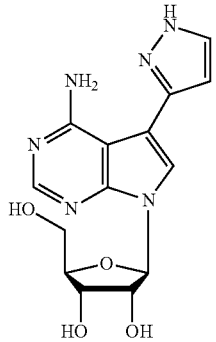

An argon purged mixture of 7-iodotubericidine 1 (392 mg, 1 mmol), pyrazole-5-boronic acid (224 mg, 2 mmol), $Na_2CO_3$ (318 mg, 3 mmol), Pd(OAc)$_2$ (11 mg, 0.05 mmol) and TPPTS (71 mg, 0.125 mmol) in water/MeCN (2:1, 5 ml) was stirred at 100° C. for 18 h. After cooling the mixture was neutralized by the addition of aq HCl (1M) and desalted by reverse phase chromatography (0→100% MeOH in water) and re-purified by column chromatography on silica (8% MeOH in CHCl$_3$) affording title compound 2n as white glassy solid (273 mg, 82%). White solid after recrystallization from boiling water. Mp 135° C. $^1$H NMR (500 MHz, DMSO-d$_6$): 3.55 (ddd, 1H, $J_{gem}$=12.1, $J_{5'b,OH}$=6.4, $J_{5'b,4'}$=4.1, H-5'b); 3.66 (ddd, 1H, $J_{gem}$=12.1, $J_{5'a,OH}$=5.0, $J_{5'a,4'}$=3.9, H-5'a); 3.90 (ddd, 1H, $J_{4',5'}$=4.1, 3.9, $J_{4',3'}$=3.2, H-4'); 4.11 (ddd, 1H, $J_{3',2'}$=5.2, $J_{3',2'}$=4.8, $J_{3',4'}$=3.2, H-3'); 4.44 (ddd, 1H, $J_{2',OH}$=6.4, $J_{2',1'}$=6.3, $J_{2',3'}$=5.2, H-2'); 6.04 (d, 1H, $J_{1',2'}$=6.1, H-1'); 6.66 (dd, 1H, $J_{4,5}$=2.4, $J_{4,NH}$=1.9, H-4-pyrazole); 7.25 (bs, 1H, NH$_a$H$_b$); 7.81 (dd, 1H, $J_{5,4}$=2.4, $J_{5,NH}$=1.5, H-5-pyrazole); 7.86 (s, 1H, H-6); 8.04 (s, 1H, H-2); 9.24 (bs, 1H, NH$_a$H$_b$); 12.88 (bs, 1H, NH). $^{13}$C NMR (125.7 MHz, DMSO-d$_6$): 61.98 (CH$_2$-5'); 70.76 (CH-3'); 73.75 (CH-2'); 85.27 (CH-4'); 87.32 (CH-1'); 100.36 (C-4a); 101.91 (CH-4-pyrazole); 109.76 (C-5); 120.64 (CH-6); 130.20 (CH-5-pyrazole); 146.26 (C-3-pyrazole); 151.02 (C-7a); 152.44 (CH-2); 158.47 (C-4). IR (KBr): 3411, 3290, 3136, 2665, 1633, 1597, 1576, 1550, 1474, 1301, 1138, 1109, 1082, 1050, 1019, 934, 798, 765, 651. MS (ESI): m/z 333 (M+H), 355 (M+Na). HRMS (ESI) for $C_{14}H_{17}N_6O_4$ [M+H] calcd: 333.1306; found: 333.1306. Anal. Calcd for $C_{14}H_{16}N_6O_4 \cdot 1.85H_2O$: C, 45.99; H, 5.43; N, 22.98. Found: C, 46.22; H, 5.44; N, 22.68.

Example 15

4-Amino-5-ethynyl-7-(β-D-ribofuranosyl)-7H-pyrrolo[2,3-d]pyrimidine (2o)

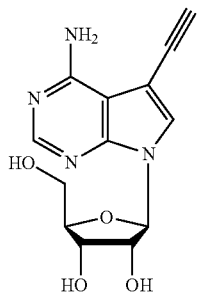

Step 1. 4-Amino-7-(β-D-ribofuranosyl)-5-[(trimethylsilyl)ethynyl]-7H-pyrrolo[2,3-d]pyrimidine (3)

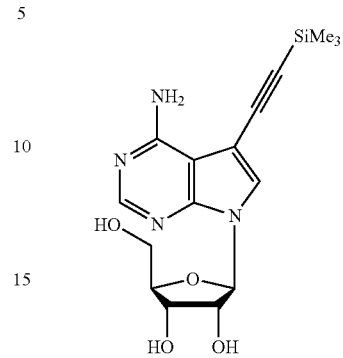

An argon purged mixture of 7-iodotubericidine 1 (1010 mg, 2.57 mmol), PdCl$_2$(PPh$_3$)$_2$ (90 mg, 0.13 mmol), CuI (49 mg, 0.26 mmol), trimethylsilylacetylene (3.6 ml, 25.7 mmol) and triethylamine (1 ml) was stirred in DMF (4 ml) at RT for 16 h. Volatiles were removed in vacuo and the rest was twice co-evaporated with EtOH and loaded on silica by co-evaporation from EtOH. Column chromatography on silica (0→3% MeOH in CHCl$_3$) afforded product 3 as off-white crystalline solid (962 mg, quantitative). Product was recrystallized from CHCl$_3$/MeOH. Mp 167-169° C. $[\alpha]_D$ −77.6 (c 0.313, DMSO). $^1$H NMR (400.0 MHz, DMSO-d$_6$): 0.24 (s, 9H, CH$_3$-TMS); 3.54 (ddd, 1H, $J_{gem}$=12.0, $J_{5'b,OH}$=6.2, $J_{5'b,4'}$=3.8, H-5'b); 3.63 (dd, 1H, $J_{gem}$=12.0, $J_{5'a,OH}$=5.0, $J_{5'a,4'}$=3.8, H-5'a); 3.90 (td, 1H, $J_{4,5}$=3.8, $J_{4',3'}$=3.2, H-4'); 4.08 (ddd, 1H, $J_{3',2'}$=5.0, $J_{3',OH}$=4.8, $J_{3',4'}$=3.2, H-3'); 4.36 (ddd, 1H, $J_{2',OH}$=6.3, $J_{2',1'}$=6.0, $J_{2',3'}$=5.0, H-2'); 5.15 (d, 1H, $J_{OH,3}$=4.7, OH-3'); 5.20 (dd, 1H, $J_{OH,5}$=6.2, 5.0, OH-5'); 5.35 (d, 1H, $J_{OH,2}$=6.3, OH-5'); 6.02 (d, 1H, $J_{1',2'}$=6.0, H-1'); 6.64 (bs, 2H, NH$_2$); 7.84 (s, 1H, H-6); 8.13 (s, 1H, H-2). $^{13}$C NMR (100.6 MHz, DMSO-d$_6$): −0.19 (CH$_3$-TMS); 61.47 (CH$_2$-5'); 70.45 (CH-3'); 74.06 (CH-2'); 85.26 (CH-4'); 87.23 (CH-1'); 94.60 (C-5); 96.78 (—C≡CTMS); 99.14 (—C≡CTMS); 102.41 (C-4a); 127.38 (CH-6); 149.48 (C-7a); 152.82 (CH-2); 157.58 (C-4). MS (ESI) m/z 363 (M+H), 385 (M+Na). HRMS (ESI) for $C_{16}H_{23}N_4O_4Si$ [M+H] calcd: 363.1483; found: 363.1484. Anal. Calcd for $C_{16}H_{22}N_4O_4Si$: C, 53.02; H, 6.12; N, 15.46. Found: C, 52.91; H, 6.11; N, 15.30.

Step 2. 4-Amino-5-ethynyl-7-(β-D-ribofuranosyl)-7H-pyrrolo[2,3-d]pyrimidine (2o)

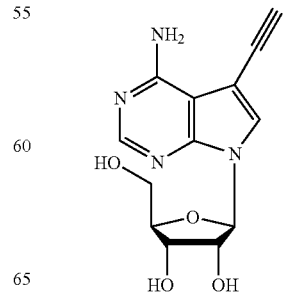

A mixture of the compound 3 from Step 1 (686 mg, 1.89 mmol) and K$_2$CO$_3$ (130 mg, 0.94 mmol) in MeOH (15 ml) was stirred at RT for 1 h, followed by the co-evaporation with silica. Column chromatography on silica (5% MeOH in CHCl$_3$) provided title compound 2o as white crystalline solid (528 mg, 96%). Compound was recrystallized from MeOH/water as long ochry needles. Mp 215-217° C. [α]$_D$ −88.3 (c 0.524, DMSO). $^1$H NMR (500.0 MHz, DMSO-d$_6$): 3.53 (ddd, 1H, J$_{gem}$=12.0, J$_{5'b,OH}$=6.2, J$_{5'b,4'}$=3.8, H-5'b); 3.63 (dd, 1H, J$_{gem}$=12.0, J$_{5'a,OH}$=5.0, J$_{5'a,4'}$=3.8, H-5'a); 3.89 (td, 1H, J$_{4',5}$=3.8, J$_{4',3}$=3.2, H-4'); 4.07 (ddd, 1H, J$_{3',2'}$=5.0, J$_{3',OH}$=4.8, J$_{3',4'}$=3.2, H-3'); 4.29 (s, 1H, HC≡C—); 4.37 (ddd, 1H, J$_{2',OH}$=6.3, J$_{2',1'}$=6.1, J$_{2',3'}$=5.0, H-2'); 5.16 (d, 1H, J$_{OH,3'}$=4.8, OH-3'); 5.23 (dd, 1H, J$_{OH,5'}$=6.2, 5.0, OH-5'); 5.38 (d, 1H, J$_{OH,2'}$=6.3, OH-5'); 6.01 (d, 1H, J$_{1',2'}$=6.1, H-1'); 6.70 (bs, 2H, NH$_2$); 7.83 (s, 1H, H-6); 8.12 (s, 1H, H-2). $^{13}$C NMR (125.7 MHz, DMSO-d$_6$): 61.73 (CH$_2$-5'); 70.74 (CH-3'); 74.21 (CH-2'); 77.52 (—C≡CH); 83.37 (—C≡CH); 85.51 (CH-4'); 87.42 (CH-1'); 94.17 (C-5); 102.65 (C-4a); 127.74 (CH-6); 149.73 (C-7a); 153.04 (CH-2); 157.78 (C-4). MS (ESI) m/z 291 (M+H), 313 (M+Na). HRMS (ESI) for C$_{13}$H$_{15}$N$_4$O$_4$ [M+H] calcd: 291.1088; found: 291.1088. Anal. Calcd for C$_{13}$H$_{14}$N$_4$O$_4$: C, 53.79; H, 4.86; N, 18.91. Found: C, 53.34; H, 4.95; N, 18.97.

Example 16

4-Amino-7-(β-D-ribofuranosyl)-5-(1H-1,2,3-triazol-4-yl)-7H-pyrrolo[2,3-d]pyrimidine (2p)

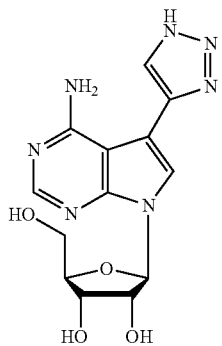

An argon purged mixture of 7-ethynyltubericidine 2o {compound from example 15} (200 mg, 0.69 mmol), CuI (6.5 mg, 0.03 mmol) and TMSN$_3$ (150 μl, 1.15 mmol) in MeOH (0.2 ml)/DMF (1.8 ml) was stirred 100° C. for 24 h. Volatiles were evaporated under reduced pressure, the residue was twice co-evaporated with MeOH and rest was suspended in MeOH and filtered through celite. Filtrate was co-evaporated with silica and column chromatography on silica afforded title compound 2p as yellowish solid (55 mg, 24%). Compound was recrystallized from water. Mp 286-288° C. [α]$_D$ −70 (c 0.217, DMSO). $^1$H NMR (499.8 MHz, DMSO-d$_6$, t=60° C.): 3.58 (dd, 1H, J$_{gem}$=11.9, J$_{5'b,4'}$=4.2, H-5'b); 3.68 (dd, 1H, J$_{gem}$=11.9, J$_{5'a,4'}$=3.9, H-5'a); 3.93 (ddd, 1H, J$_{4',5}$=4.2, 3.9, J$_{4',3}$=3.6, H-4'); 4.15 (dd, 1H, J$_{3',2'}$=5.3, J$_{3',4'}$=3.6, H-3'); 4.45 (dd, 1H, J$_{2',1'}$=6.0, J$_{2',3'}$=5.3, H-2'); 4.93, 5.04 and 5.17 (3×bs, 3×1H, OH-2',3',5'); 6.08 (d, 1H, J$_{1',2'}$=6.0, H-1'); 7.85 (bs, 2H, NH$_2$); 7.91 (s, 1H, H-6); 8.09 (s, 1H, H-2); 8.23 (s, 1H, H-5-triazole). $^{13}$C NMR (125.7 MHz, DMSO-d$_6$, t=60° C.): 61.83 (CH$_2$-5'); 70.54 (CH-3'); 73.72 (CH-2'); 85.15 (CH-4'); 87.41 (CH-1'); 100.16 (C-4a); 105.83 (C-5); 120.80 (CH-6); 126.16 (CH-5-triazole); 141.51 (C-4-triazole); 151.04 (C-7a); 152.35 (CH-2); 158.04 (C-4). MS (ESI) m/z 334 (M+H), 356 (M+Na). HRMS (ESI) for C$_{13}$H$_{16}$N$_7$O$_4$[M+H] calcd: 334.1258; found: 334.1258. Anal. Calcd for C$_{13}$H$_{15}$N$_7$O$_4$: C, 46.85; H, 4.54; N, 29.42. Found: C, 47.12; H, 4.82; N, 27.96.

Example 17

4-Amino-7-(β-D-ribofuranosyl)-5-(thiazol-2-yl)-7H-pyrrolo[2,3-d]pyrimidine (2q)

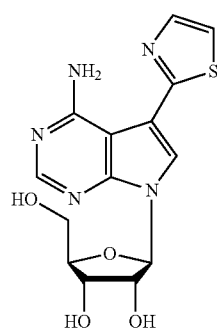

Step 1. 4-Amino-5-iodo-7-[2,3,5-tris-O-(tert-butyldimethylsilyl)-β-D-ribofuranosyl]-7H-pyrrolo[2,3-d]pyrimidine (4)

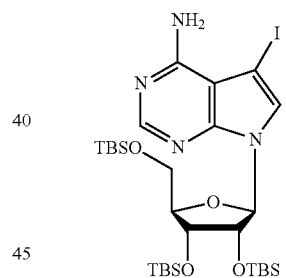

tert-Butyldimethylsilyl chloride (6.78 g, 45 mmol) was added to a solution of 7-iodotubericidine 1 (3.92 g, 10 mmol) and imidazole (6.12 g, 90 mmol) in DMF (20 ml) and the mixture was stirred overnight at RT. The mixture was diluted with hexane (100 ml) and washed with aq NaCl (5%, 100 ml). Aqueous layer was re-extracted with hexane (2×25 ml). Organic phase was washed with aq NaCl (5% w/w, 4×50 ml). Collected organic extracts were dried over MgSO$_4$, evaporated and chromatographed on silica (hexanes/AcOEt, 50:1→5:1) affording title compound 4 as colorless foam (3.05 g, 41%) and faster moving byproduct resulting from 6-amino group N-silylation. This oversilylation byproduct was converted to title compound 4 by standing of its methanolic solution at RT for several days (2.96 g, 40%). Total yield of title compound 4 is 81%. $^1$H NMR (500.0 MHz, CDCl$_3$): −0.28, −0.08, 0.096, 0.098, 0.17 and 0.18 (6×s, 6×3H, CH$_3$Si); 0.77, 0.93 and 0.99 (3×s, 3×9H, (CH$_3$)C); 3.77 (dd, 1H, J$_{gem}$=11.4, J$_{5'b,4'}$=2.3, H-5'b); 3.95 (dd, 1H, J$_{gem}$=11.4, J$_{5'a,4'}$=3.0, H-5'a); 4.08 (td, 1H, J$_{4',5}$=3.0, 2.3, J$_{4',3}$=3.0, H-4'); 4.22 (dd, 1H, J$_{3',2'}$=4.5, $J_{3',4'}$=3.0, H-3'); 4.39 (dd, 1H, $J_{2',1'}$=5.6, $J_{2',3'}$=4.5, H-2'); 5.70 (bs, 2H, NH$_2$); 6.26 (d, 1H, $J_{1',2'}$=5.6, H-1'); 7.52 (s, 1H, H-6); 8.26 (s, 1H, H-2). $^{13}$C NMR (125.7 MHz, CDCl$_3$): −5.33, −5.31, −5.26, −4.76, −4.75 and −4.41 (CH$_3$Si); 17.84, 18.10 and 18.60 (C(CH$_3$)$_3$); 25.65, 25.84 and 26.17 ((CH$_3$)$_3$C); 50.20 (C-5); 62.94 (CH$_2$-5'); 72.43 (CH-3'); 76.78 (CH-2'); 85.46 (CH-4'); 87.48 (CH-1'); 104.26 (C-4a); 126.62 (CH-6); 150.66 (C-7a); 152.19 (CH-2); 156.74 (C-4). MS (ESI) m/z 735 (M+H), 757 (M+Na).

Step 2. 4-Amino-5-(thiazol-2-yl)-7-[2,3,5-tris-O-(tert-butyldimethylsilyl)-β-D-ribofuranosyl]-7H-pyrrolo[2,3-d]pyrimidine (5)

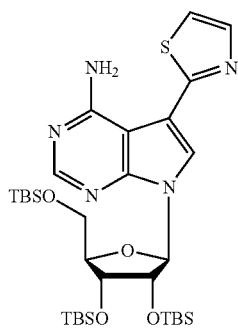

An argon purged mixture of the compound 4 from Step 1 (544 mg, 0.74 mmol), 2-(tributylstannyl)thiazole (554 mg, 1.48 mmol) and PdCl$_2$(PPh$_3$)$_2$ (22 mg, 0.03 mmol) in DMF (3 ml) was stirred at 100° C. for 48 h. Volatiles were evaporated under deminished pressure, the residue was co-evaporated with water (3×), twice with MeOH, twice with hexane and then co-evaporated with silica from hexane. Column chromatography on silica (hexanes then hexanes/AcOEt, 10:1→6:1) afforded title compound 5 as foam (454 mg, 89%). $^1$H NMR (500.0 MHz, CDCl$_3$): −0.36, −0.10, 0.11, 0.13, 0.17 and 0.18 (6×s, 6×3H, CH$_3$Si); 0.74, 0.95 and 0.99 (3×s, 3×9H, (CH$_3$)C); 3.79 (dd, 1H, $J_{gem}$=11.4, $J_{5'b,4'}$=2.7, H-5'b); 3.96 (dd, 1H, $J_{gem}$=11.4, $J_{5'a,4'}$=3.2, H-5'a); 4.11 (ddd, 1H, $J_{4',5'}$=3.9, 2.7, $J_{4',3'}$=1.8, H-4'); 4.23 (dd, 1H, $J_{3',2'}$=4.7, $J_{3',4'}$=1.8, H-3'); 4.55 (dd, 1H, $J_{2',1'}$=6.9, $J_{2',3'}$=4.7, H-2'); 5.96 (bs, 1H, NH$_a$H$_b$); 6.31 (d, 1H, $J_{1',2'}$=6.9, H-1'); 7.21 (d, 1H, $J_{5,4}$=3.4, H-5-thiazolyl); 7.72 (d, 1H, $J_{4,5}$=3.4, H-4-thiazolyl); 7.74 (s, 1H, H-6); 8.26 (s, 1H, H-2); 9.79 (bs, 1H, NH$_a$H$_b$). $^{13}$C NMR (125.7 MHz, CDCl$_3$): −5.35, −5.33, −5.19, −4.65, −4.61 and −4.47 (CH$_3$Si); 17.82, 18.13 and 18.57 (C(CH$_3$)$_3$); 25.61, 25.86 and 26.15 ((CH$_3$)$_3$C); 63.37 (CH$_2$-5'); 73.03 (CH-3'); 76.26 (CH-2'); 86.28 (CH-4'); 87.01 (CH-1'); 100.52 (C-4a); 112.19 (C-5); 116.76 (CH-5-thiazolyl); 122.24 (CH-6); 141.71 (CH-4-thiazolyl); 151.57 (C-7a); 151.94 (CH-2); 157.52 (C-4); 163.53 (C-2-thiazolyl). MS (ESI) m/z 692 (M+H), 714 (M+Na). HRMS (ESI) for C$_{32}$H$_{58}$N$_5$O$_4$SSi$_3$ [M+H] calcd: 692.3512; found: 692.3512.

Step 3. 4-Amino-7-(β-D-ribofuranosyl)-5-(thiazol-2-yl)-7H-pyrrolo[2,3-d]pyrimidine (2q)

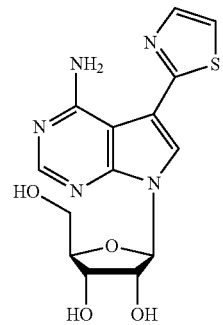

Compound 5 from Step 2 (448 mg, 0.65 mmol) was treated with aq HCl (1M, 1 ml) in MeOH (1 ml) at RT for 2 h. Volatiles were removed in vacuo and solid residue was co-evaporated with water (6×). Crude product was recrystallized from MeOH/water affording title compound 2q as white long needles (132 mg, 58%). Mother liquors were purified by column chromatography on silica (8% MeOH in CHCl$_3$) affording additional portion of product (61 mg, 27%). Overall yield 85%. Mp 226-228° C. [α]$_D$ −81.5 (c 0.254, DMSO). $^1$H NMR (600.1 MHz, DMSO-d$_6$): 3.61 (dd, 1H, $J_{gem}$=12.0, $J_{5'b,4'}$=3.6, H-5'b); 3.72 (dd, 1H, $J_{gem}$=12.0, $J_{5'a,4'}$=3.9, H-5'a); 3.97 (td, 1H, $J_{4',5'}$=3.9, 3.6, $J_{4',3'}$=3.9, H-4'); 4.16 (dd, 1H, $J_{3',2'}$=4.9, $J_{3',4'}$=3.9, H-3'); 4.41 (dd, 1H, $J_{2',1'}$=5.6, $J_{2',3'}$=4.9, H-2'); 6.14 (d, 1H, $J_{1',2'}$=5.6, H-1'); 7.80 (d, 1H, $J_{5,4}$=3.3, H-5-thiazolyl); 7.91 (d, 1H, $J_{4,5}$=3.3, H-4-thiazolyl); 8.48 (s, 1H, H-2); 8.62 (s, 1H, H-6); 8.99 and 10.88 (2×bs, 2H, NH$_2$). $^{13}$C NMR (150.9 MHz, DMSO-d$_6$): 61.12 (CH$_2$-5'); 70.19 (CH-3'); 74.78 (CH-2'); 85.80 (CH-4'); 87.63 (CH-1'); 99.39 (C-4a); 113.09 (C-5); 120.13 (CH-5-thiazolyl); 125.34 (CH-6); 142.09 (CH-4-thiazolyl); 145.00 (CH-2); 148.55 (C-7a); 152.47 (C-4); 162.07 (C-2-thiazolyl). MS (ESI) m/z 350 (M+H), 372 (M+Na). HRMS (ESI) for C$_{14}$H$_{16}$N$_5$O$_4$S [M+H] calcd: 350.0918; found: 350.0918. Anal. Calcd for C$_{14}$H$_{15}$N$_5$O$_4$S.½H$_2$O.CH$_3$OH: C, 46.15; H, 5.16; N, 17.94. Found: C, 46.41; H, 4.96; N, 17.67.

Example 18

4-Amino-5-(1H-imidazol-4-yl)-7-(β-D-ribofuranosyl)-7H-pyrrolo[2,3-d]pyrimidine (2r)

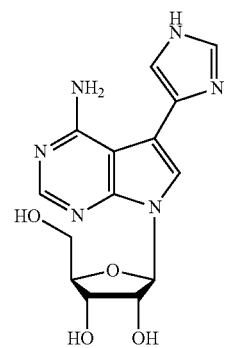

To a solution of 4-iodo-1-trityl-1H-imidazole (609 mg, 1.4 mmol) in dry THF (6 ml) was added EtMgBr (1M in THF, 1.5 ml, 1.5 mmol) and the mixture was stirred at RT for 10 min. Then a solution of ZnCl$_2$ (1M in THF, 2.8 ml, 2.8 mmol) was dropwise added and the mixture was stirred for 2 h. Resulting thick slurry was transferred to an argon purged mixture of 2',3',5'-tri-O-TBS-7-iodotubericidine {compound 4 from Example 17, Step 1} (515 mg, 0.7 mmol) and Pd(PPh$_3$)$_4$ (40 mg, 0.035 mmol) and the mixture was stirred at 90° C. for 16 h. The mixture was diluted with CHCl$_3$ (20 ml) and washed with aq EDTA (sat., 20 ml). Aqueous layer was re-extracted with CHCl$_3$ (2×5 ml). Collected organic extracts were dried over MgSO$_4$, evaporated and chromatographed on silica (hexanes/AcOEt, 4:1→3:1) affording crude TBS,Tr-protected product contaminated by N-tritylimidazole. Crude product was deprotected by stirring in aq TFA (90% v/v, 2 ml) at RT for 18 h. The volatiles were removed in vacuo and the residue was several times co-evaporated with MeOH and finally loaded on silica by co-evaporation from MeOH. Column chromatography on silica (0→10% MeOH in CHCl$_3$) afforded title compound 2r as white powder (179 mg, 77%). Compound was recrystallized from MeOH/water. Mp 276-278° C. [α]$_D$ −61.4 (c 0.249, DMSO). $^1$H NMR (500.0 MHz, DMSO-d$_6$): 3.53 (ddd, 1H, J$_{gem}$=12.0, J$_{5'b,OH}$=6.5, J$_{5'b,4'}$=4.2, H-5'b); 3.64 (dd, 1H, J$_{gem}$=12.0, J$_{5'a,OH}$=4.8, J$_{5'a,4'}$=4.2, H-5'a); 3.89 (td, 1H, J$_{4',5'}$=4.2, J$_{4',3'}$=3.4, H-4'); 4.09 (ddd, 1H, J$_{3',2'}$=5.0, J$_{3',OH}$=4.8, J$_{3',4'}$=3.4, H-3'); 4.41 (ddd, 1H, J$_{2',OH}$=6.5, J$_{2',1'}$=6.3, J$_{2',3'}$=5.0, H-2'); 5.14 (d, 1H, J$_{OH,3'}$=4.8, OH-3'); 5.30 (dd, 1H, J$_{OH,5'}$=6.5, 4.8, OH-5'); 5.34 (d, 1H, J$_{OH,2'}$=6.5, OH-5'); 6.03 (d, 1H, J$_{1',2'}$=6.3, H-1'); 7.14 (bs, 1H, NH$_a$H$_b$); 7.50 (d, 1H, J$_{5,NH}$=2.0, J$_{5,2}$=0.8, H-5-imidazole); 7.68 (s, 1H, H-6); 7.81 (d, 1H, J$_{2,5}$=0.8, H-2-imidazole); 8.01 (s, 1H, H-2); 9.99 (bs, 1H, NH$_a$H$_b$); 12.31 (bs, 1H, NH-imidazole). $^{13}$C NMR (125.7 MHz, DMSO-d$_6$): 62.11 (CH$_2$-5'); 70.87 (CH-3'); 73.76 (CH-2'); 85.23 (CH-4'); 87.30 (CH-1'); 100.77 (C-4a); 110.84 (C-5); 111.81 (CH-5-imidazole); 117.90 (CH-6); 134.95 (CH-2-imidazole); 135.10 (C-4-imidazole); 150.56 (C-7a); 152.08 (CH-2); 158.59 (C-4). MS (ESI) m/z 333 (M+H), 355 (M+Na). HRMS (ESI) for C$_{14}$H$_{17}$N$_6$O$_4$ [M+H] calcd: 333.1306; found: 333.1306. Anal. Calcd for C$_{14}$H$_{16}$N$_6$O$_4$: C, 50.60; H, 4.85; N, 25.29. Found: C, 50.55; H, 5.01; N, 24.28.

Example 19

4-Amino-5-(1H-imidazol-2-yl)-7-(β-D-ribofuranosyl)-7H-pyrrolo[2,3-d]pyrimidine (2s)

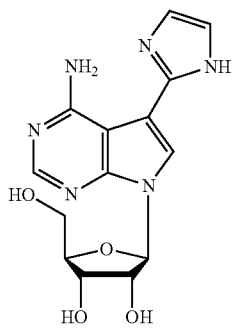

To a stirred solution of 1-(N,N-dimethylsulfamoyl)-1H-imidazole (875 mg, 5 mmol) in THF (15 ml) was dropwise added n-butyllithium (1.6 M in hexane, 3.1 ml, 5 mmol) at −78° C. during 30 min. Then a solution of ZnCl$_2$ (1M in THF, 10 ml, 10 mmol) was dropwise added at −78° C. and the mixture was warmed to RT during 45 min. Resulting orange solution was transferred to an argon purged mixture of 2',3',5'-tri-O-TBS-7-iodotubericidine {compound 4 from Example 17, Step 1} (735 mg, 1 mmol) and Pd(PPh$_3$)$_4$ (116 mg, 0.1 mmol) and the mixture was stirred at 90° C. for 24 h. The mixture was diluted with AcOEt (50 ml) and washed with aq EDTA (sat., 25 ml). Aqueous layer was re-extracted with AcOEt (10 ml). Collected organic extracts were dried over MgSO$_4$, evaporated and the residue was chromatographed on silica (hexanes/AcOEt, 5:1→1:1; then AcOEt) affording product in a mixture with unseparable starting protected imidazole. This mixture was directly deprotected by stirring in aq HCl (1M, 2 ml) and MeOH (2 ml) at 100° C. for 24 h. Volatiles were removed in vacuo and the rest was co-evaporated with water (5×). The residue was treated with MeOH and undissolved solid (imidazole) was filtered off and washed with MeOH. Filtrate was evaporated and reverse phase chromatography (0→100% MeOH in water) afforded crude product, which was yet re-purified by column chromatography on silica (8% MeOH in CHCl$_3$) providing title compound 2s as yellowish foam (42 mg, 13%). Compound was recrystallized from MeOH/water. Mp 153-156° C. [α]$_D$ −72.1 (c 0.19, DMSO). $^1$H NMR (499.8 MHz, DMSO-d$_6$): 3.56 (ddd, 1H, J$_{gem}$=11.9, J$_{5'b,OH}$=6.5, J$_{5'b,4'}$=4.6, H-5'b); 3.64 (dd, 1H, J$_{gem}$=11.9, J$_{5'a,OH}$=5.0, J$_{5'a4'}$=4.1, H-5'a); 3.92 (ddd, 1H, J$_{4',5'}$=4.6, 4.1, J$_{4',3'}$=3.4, H-4'); 4.10 (ddd, 1H, J$_{3',OH}$=5.2, J$_{3',2'}$=5.0, J$_{3',4'}$=3.4, H-3'); 4.36 (ddd, 1H, J$_{2',OH}$=6.3, J$_{2',1'}$=6.0, J$_{2',3'}$=5.0, H-2'); 5.16 (dd, 1H, J$_{OH,5'}$=6.5, 5.0, OH-5'); 5.17 (d, 1H, J$_{OH,3'}$=5.2, OH-3'); 5.39 (d, 1H, J$_{OH,1}$=6.3, OH-5'); 6.05 (d, 1H, J$_{1',2'}$=6.0, H-1'); 7.00 (t, 1H, J$_{4,5}$=J$_{4,NH}$=1.4, H-4-imidazole); 7.22 (dd, 1H, J$_{5,NH}$=2.0, J$_{5,4}$=1.4, H-5-imidazole); 7.24 (bs, 1H, NH$_a$H$_b$); 7.86 (s, 1H, H-6); 8.06 (s, 1H, H-2); 10.23 (bs, 1H, NH$_a$H$_b$); 12.42 (bs, 1H, NH-imidazole). $^{13}$C NMR (125.7 MHz, DMSO-d$_6$): 62.25 (CH$_2$-5'); 70.90 (CH-3'); 73.99 (CH-2'); 85.27 (CH-4'); 87.33 (CH-1'); 100.12 (C-4a); 107.87 (C-5); 116.81 (CH-5-imidazole); 119.44 (CH-6); 127.22 (CH-4-imidazole); 142.49 (C-2-imidazole); 150.82 (C-7a); 152.91 (CH-2); 158.58 (C-4). MS (ESI) m/z 333 (M+H), 355 (M+Na). HRMS (ESI) for C$_{14}$H$_{17}$N$_6$O$_4$ [M+H] calcd: 333.1306; found: 333.1306. Anal. Calcd for C$_{14}$H$_{16}$N$_6$O$_4$·1.85H$_2$O·0.55 CH$_3$OH: C, 45.60; H, 5.76; N, 21.93. Found: C, 45.67; H, 5.66; N, 21.86.

Example 20

4-Amino-7-(2-C-methyl-β-D-ribofuranosyl)-5-phenyl-7H-pyrrolo[2,3-d]pyrimidine (7a)

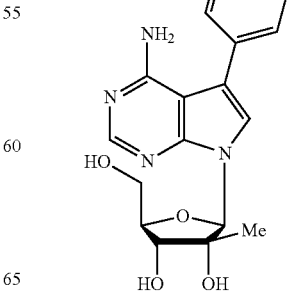

Step 1. 4-Chloro-5-iodo-7-(2-C-methyl-2,3,5-tri-O-benzoyl-β-D-ribofuranosyl)-7H-pyrrolo[2,3-d]pyrimidine (10).

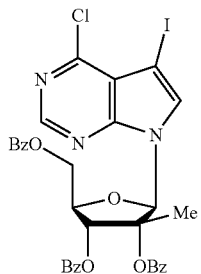

To a mixture of 4-chloro-5-iodo-7H-pyrrolo[2,3-d]pyrimidine 8 (903 mg, 3.23 mmol), 2-C-methyl-1,2,3,5-tetra-O-benzoyl-β-D-ribofuranose 9 (1.7 g, 2.93 mmol) and DBU (1.3 ml, 8.69 mmol) in MeCN (20 ml) was dropwise added TMSOTf (2.1 ml, 11.62 mmol) at 0° C. and the mixture was then stirred at 70° C. for 22.5 h. After cooling, the mixture was diluted with AcOEt (100 ml), washed with aq NaHCO$_3$ (sat., 25 ml), water (25 ml) and brine (25 ml). The organic layer was dried over MgSO$_4$ and evaporated. The residue was chromatographed on silica (hexanes/toluene, 1:1; then hexanes/toluene/MeCN, 49:49:2→3:3:4) affording title compound 10 as a white foam (1.04 g, 48%). Compound was recrystallized from EtOH. Mp 95° C. [α]$^{20}_D$ −69.3 (c 0.280, CHCl$_3$). $^1$H NMR (500 MHz, CDCl$_3$): 1.59 (s, 3H, CH$_3$); 4.72 (td, 1H, J$_{4',3'}$=J$_{4',5'b}$=5.8, J$_{4',5'a}$=3.4, H-4'); 4.85 (dd, 1H, J$_{gem}$=12.2, J$_{5'b,4'}$=5.8, H-5'b); 4.95 (dd, 1H, J$_{gem}$=12.2, J$_{5'a,4'}$=3.4, H-5'a); 6.03 (d, 1H, J$_{3',4'}$=5.8, H-3'); 6.95 (s, 1H, H-1'); 7.34, 7.46 and 7.47 (3×m, 3×2H, H-m-Bz); 7.54, 7.59 and 7.61 (3×m, 3×1H, H-p-Bz); 7.69 (s, 1H, H-6); 7.96, 8.10 and 8.11 (3×m, 3×2H, H-o-Bz); 8.75 (s, 1H, H-2). $^{13}$C NMR (125.7 MHz, CDCl$_3$): 17.92 (CH$_3$); 52.68 (C-5); 63.33 (CH$_2$-5'); 75.55 (CH-3'); 80.04 (CH-4'); 84.93 (C-2'); 88.95 (CH-1'); 117.71 (C-4a); 128.49, 128.54 and 128.63 (CH-m-Bz); 128.65, 129.50 and 129.61 (C-i-Bz); 129.78, 129.83 and 129.92 (CH-o-Bz); 132.66 (CH-6); 133.38, 133.66, 133.72 (CH-p-Bz); 150.68 (C-7a); 151.17 (CH-2); 153.15 (C-4); 165.09, 165.33 and 166.32 (CO). IR (CHCl$_3$): 3092, 3066, 3034, 1727, 1602, 1587, 1577, 1538, 1504, 1493, 1451, 1444, 1339, 1316, 1269, 1248, 1178, 1162, 1141, 1116, 1070, 1027, 1002, 952, 943, 843, 822, 725, 712, 686, 617, 600. MS (FAB): m/z 738 (M+H). HRMS (FAB) for C$_{33}$H$_{26}$ClIN$_3$O$_7$ [M+H] calcd: 738.0504; found: 738.0491. Anal. Calcd for C$_{33}$H$_{25}$ClIN$_3$O$_7$: C, 53.71; H, 3.41; N, 5.69. Found: C, 53.91; H, 3.29; N, 5.38.

Step 2. 4-Amino-5-iodo-7-(2-C-methyl-β-D-ribofuranosyl)-7H-pyrrolo[2,3-d]pyrimidine (6).

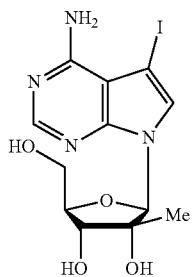

A mixture of compound 10 from Step 1 (200 mg, 0.27 mmol) and aq ammonia (25% w/w, 3 ml) in dioxane (3 ml) was stirred in a sealed tube at 120° C. for 10 h. After cooling the volatiles were evaporated and crude product was purified by chromatography on silica (CHCl$_3$→CHCl$_3$/MeOH, 8:2) and then re-purified by reverse phase chromatography (0→100% MeOH in water) to afford title compound 6 as white solid (76 mg, 69%). Compound was recrystallized from MeOH/MeCN. Mp 207° C. [α]$^{20}_D$ −39.0 (c 0.274, MeOH). $^1$H NMR (600 MHz, DMSO-d$_6$): 0.67 (s, 3H, CH$_3$); 3.65 (ddd, 1H, J$_{gem}$=12.1, J$_{5'b,OH}$=4.8, J$_{5'b,4'}$=2.7, H-5'b); 3.81 (ddd, 1H, J$_{gem}$=12.1, J$_{5'a,OH}$=4.8, J$_{5'a,4'}$=2.0, H-5'a); 3.79 (ddd, 1H, J$_{4',3'}$=9.1, J$_{4',5'}$=2.7, 2.0, H-4'); 3.93 (bd, 1H, J$_{3',4'}$=9.1, H-3'); 5.14 (s, 1H, OH-2'); 5.16 (bs, 1H, OH-3'); 5.22 (t, 1H, J$_{OH,5'}$=4.8, OH-5'); 6.10 (s, 1H, H-1'); 6.67 (bs, 2H, NH$_2$); 7.82 (s, 1H, H-6); 8.10 (s, 1H, H-2). $^{13}$C NMR (151 MHz, DMSO-d$_6$): 19.89 (CH$_3$); 51.68 (C-5); 59.46 (CH$_2$-5'); 71.76 (CH-3'); 78.87 (C-2'); 82.39 (CH-4'); 90.71 (CH-1'); 103.11 (C-4a); 126.81 (CH-6); 149.88 (C-7a); 152.23 (CH-2); 157.43 (C-4). IR (KBr): 3474, 3429, 3392, 3366, 1631, 1582, 1553, 1504, 1440, 1343, 1295, 1147, 1128, 1070, 1045, 789. MS (FAB): m/z 407 (M+H). HRMS (FAB) for C$_{12}$H$_{16}$IN$_4$O$_4$ [M+H] calcd: 407.0216; found: 407.0225. Anal. Calcd for C$_{12}$H$_{15}$IN$_4$O$_4$: C, 35.48; H, 3.72; N, 13.79. Found: C, 35.37; H, 3.72; N, 13.39.

Step 3. 4-Amino-7-(2-C-methyl-β-D-ribofuranosyl)-5-phenyl-7H-pyrrolo[2,3-d]pyrimidine (7a)

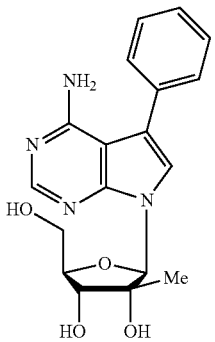

An argon purged mixture of compound 6 from Step 2 (49 mg, 0.12 mmol), phenylboronic acid (25 mg, 0.20 mmol), Na$_2$CO$_3$ (144 mg, 1.36 mmol), TPPTS (15.5 mg, 0.027 mmol) and Pd(OAc)$_2$ (1.4 mg, 6.2 μmol) in water/MeCN (2:1, 1.8 ml) was stirred at 80° C. for 1 h. After cooling, volatiles were removed by evaporation and the residue was purified by reverse phase chromatography (0→100% MeOH in water) affording title compound 7a as white solid (30 mg, 70%). Mp 129° C. [α]$^{20}_D$ −55.7 (c 0.226, MeOH). $^1$H NMR (600 MHz, DMSO-d$_6$): 0.75 (s, 3H, CH$_3$); 3.65 (bdd, 1H, J$_{gem}$=12.2, J$_{5'b,4'}$=2.9, H-5'b); 3.82 (bdd, 1H, J$_{gem}$=12.2, J$_{5'a,4'}$=2.1, H-5'a); 3.86 (ddd, 1H, J$_{4',3'}$=9.1, J$_{4',5'}$=2.9, 2.1, H-4'); 4.02 (d, 1H, J$_{3',4'}$=9.1, H-3'); 5.15 (bs, 3H, OH-2',3',5'); 6.10 (bs, 2H, NH$_2$); 6.23 (s, 1H, H-1'); 7.36 (m, 1H, H-p-Ph); 7.44-7.50 (m, 4H, H-o,m-Ph); 7.70 (s, 1H, H-6); 8.16 (s, 1H, H-2). $^{13}$C NMR (151 MHz, DMSO-d$_6$): 20.00 (CH$_3$); 59.60 (CH$_2$-5'); 72.01 (CH-3'); 78.88 (C-2'); 82.39 (CH-4'); 90.51 (CH-1'); 100.09 (C-4a); 116.41 (C-5); 120.75 (CH-6); 127.05 (CH-p-Ph); 128.64 (CH-o-Ph); 129.23 (CH-m-Ph); 134.89 (C-i-Ph); 150.67 (C-7a); 151.94 (CH-2); 157.49 (C-4). IR (KBr): 3480, 3431, 3400, 1631, 1622, 1585, 1566, 1537, 1489, 1464, 1445, 1299, 1178, 1123, 1073, 1058, 1029, 799, 763, 705, 550. MS (FAB) m/z 357 (M+H). HRMS (FAB) for $C_{18}H_{21}N_4O_4$: [M+H] calcd: 357.1563; found: 357.1557. Anal. Calcd for $C_{18}H_{20}N_4O_4 \cdot 1.6H_2O$: C, 56.13; H, 6.07; N, 14.54. Found: C, 56.52; H, 5.74; N, 14.14.

Example 21

4-Amino-5-(4-methoxyphenyl)-7-(2-C-methyl-β-D-ribofuranosyl)-7H-pyrrolo[2,3-d]pyrimidine (7b)

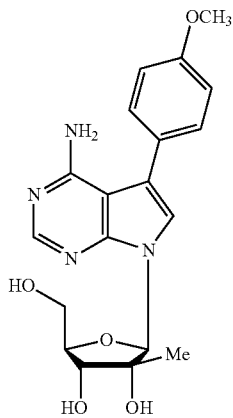

Title compound was prepared by following the procedure in Example 20, Step 3. White solid. Yield 67%. Mp 127° C. $[\alpha]^{20}_D$ −48.4 (c 0.225, MeOH). $^1$H NMR (600 MHz, DMSO-$d_6$): 0.74 (s, 3H, $CH_3$); 3.64 (bdd, 1H, $J_{gem}$=12.21, $J_{5'b,4'}$=2.9, H-5'b); 3.80 (s, 3H, $CH_3O$); 3.81 (bdd, 1H, $J_{gem}$=12.1, $J_{5'a,4'}$=2.1, H-5'a); 3.85 (ddd, 1H, $J_{4',3'}$=9.1, $J_{4',5'}$=2.9, 2.1, H-4'); 4.01 (d, 1H, $J_{3',4'}$=9.1, H-3'); 5.13 (bs, 3H, OH-2',3',5'); 6.08 (bs, 2H, $NH_2$); 6.22 (s, 1H, H-1'); 7.04 (m, 2H, H-m-$C_6H_4OMe$); 7.36 (m, 2H, H-o-$C_6H_4OMe$); 7.60 (s, 1H, H-6); 8.14 (s, 1H, H-2). $^{13}$C NMR (151 MHz, DMSO-$d_6$): 19.99 ($CH_3$); 55.39 ($CH_3O$); 59.61 ($CH_2$-5'); 72.03 (CH-3'); 78.87 (C-2'); 82.34 (CH-4'); 90.47 (CH-1'); 100.31 (C-4a); 114.65 (CH-m-$C_6H_4OMe$); 116.06 (C-5); 120.14 (CH-6); 127.04 (C-i-$C_6H_4OMe$); 129.91 (CH-o-$C_6H_4OMe$); 150.45 (C-7a); 151.85 (CH-2); 157.51 (C-4); 158.58 (C-p-$C_6H_4OMe$). IR (KBr): 3435, 2836, 1631, 1622, 1586, 1565, 1539, 1506, 1464, 1419, 1293, 1247, 1174, 1110, 1072, 1033, 839, 798, 791, 712, 550. MS (FAB) m/z 387 (M+H). HRMS (FAB) for $C_{19}H_{23}N_4O_5$ [M+H] calcd: 387.1668; found: 387.1665. Anal. Calcd for $C_{19}H_{22}N_4O_5 \cdot 1.6H_2O$: C, 54.96; H, 6.12; N, 13.49. Found: C, 55.30; H, 5.91; N, 13.18.

Example 22

4-Amino-7-(2-C-methyl-β-D-ribofuranosyl)-5-(naphtalen-1-yl)-7H-pyrrolo[2,3-d]pyrimidine (7c)

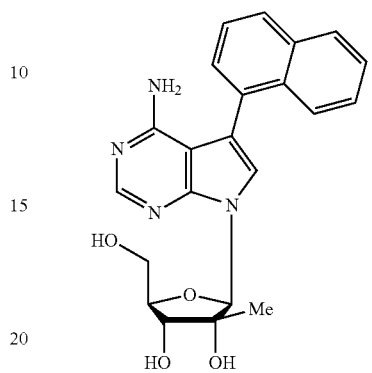

Title compound was prepared by following the procedure in Example 20, Step 3. Crude product was prepurified by chromatography on silica (0→20% MeOH in $CHCl_3$) before final reverse phase chromatography. Tan solid. Yield 41%. Mp 142° C. $[\alpha]^{20}_D$ −58.6 (c 0.239, MeOH). $^1$H NMR (500 MHz, DMSO-$d_6$, T=353 K): 0.90 (s, 3H, $CH_3$); 3.67 (dd, 1H, $J_{gem}$=12.2, $J_{5'b,4'}$=3.5, H-5'b); 3.83 (dd, 1H, $J_{gem}$=12.2, $J_{5'a,4'}$=2.3, H-5'a); 3.91 (ddd, 1H, $J_{4',3'}$=8.9, $J_{4',5'}$=3.5, 2.3, H-4'); 4.04 (d, 1H, $J_{3',4'}$=8.9, H-3'); 4.89 (bs, 3H, OH-2',3',5'); 5.39 (bs, 2H, $NH_2$); 6.34 (s, 1H, H-1'); 7.500 (ddd, 1H, $J_{7,8}$=8.3, $J_{7,6}$=6.9, $J_{7,5}$=1.3, H-7-naphth); 7.502 (dd, 1H, $J_{2,3}$=6.9, $J_{2,4}$=1.3, H-2-naphth); 7.56 (ddd, 1H, $J_{6,5}$=8.1, $J_{6,7}$=6.9, $J_{6,8}$=1.3, H-6-naphth); 7.60 (dd, 1H, $J_{3,4}$=8.3, $J_{3,2}$=6.9, H-3-naphth); 7.63 (s, 1H, H-6); 7.75 (dddd, 1H, $J_{8,7}$=8.3, $J_{8,6}$=1.3, $J_{8,4}$=1.0, $J_{8,5}$=0.8, H-8-naphth); 7.98 (ddd, 1H, $J_{4,3}$=8.3, $J_{4,2}$=1.3, $J_{4,8}$=1.0, H-4-naphth); 8.01 (ddd, 1H, $J_{5,6}$=8.1, $J_{5,7}$=1.3, $J_{5,8}$=0.8, H-5-naphth); 8.19 (s, 1H, H-2). $^{13}$C NMR (151 MHz, DMSO-$d_6$, T=353 K): 19.73 ($CH_3$); 59.70 ($CH_2$-5'); 72.30 (CH-3'); 78.69 (C-2'); 82.28 (CH-4'); 90.64 (CH-1'); 102.10 (C-4a); 113.02 (C-5); 121.50 (CH-6); 125.27 (CH-8-naphth); 125.38 (CH-3-naphth); 125.98 (CH-6-naphth); 126.42 (CH-7-naphth); 127.82 (CH-4-naphth); 128.12 (CH-2,5-naphth); 131.63 (C-1-naphth); 132.13 (C-8a-naphth); 133.39 (C-4a-naphth); 150.05 (C-7a); 151.61 (CH-2); 156.96 (C-4). IR (KBr): 3478, 3438, 3395, 3058, 2973, 1620, 1583, 1578, 1568, 1533, 1507, 1468, 1398, 1377, 1298, 1256, 1178, 1143, 1117, 1071, 1050, 1035, 1018, 852, 799, 786, 780, 740. MS (ESI) m/z 407 (M+H), 429 (M+Na). HRMS (ESI) for $C_{22}H_{23}N_4O_4$ [M+H] calcd: 407.1714; found: 407.1704. Anal. Calcd for $C_{22}H_{22}N_4O_4 \cdot 1.5H_2O$: C, 60.96; H, 5.81; N, 12.93. Found: C, 61.30; H, 5.72; N, 13.28.

Example 23

4-Amino-7-(2-C-methyl-β-D-ribofuranosyl)-5-(naphtalen-2-yl)-7H-pyrrolo[2,3-d]pyrimidine (7d)

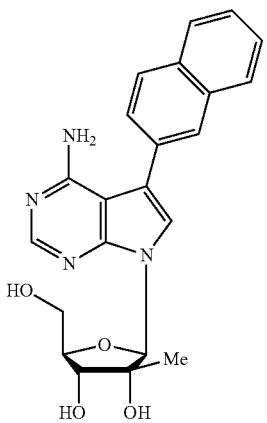

Title compound was prepared by following the procedure in Example 20, Step 3. Crude product was prepurified by chromatography on silica (0→20% MeOH in CHCl$_3$) before final reverse phase chromatography. Cream solid. Yield 65%. Mp 143° C. [α]$^{20}_D$ −64.3 (c 0.253, MeOH). $^1$H NMR (500 MHz, DMSO-d$_6$): 0.79 (s, 3H, CH$_3$); 3.66 (ddd, 1H, J$_{gem}$=12.6, J$_{5'b,OH}$=5.0, J$_{5'b,4'}$=2.9, H-5'b); 3.84 (ddd, 1H, J$_{gem}$=12.6, J$_{5'a,OH}$=5.0, J$_{5'a,4'}$=2.1, H-5'a); 3.88 (ddd, 1H, J$_{4',3'}$=9.1, J$_{4',5'}$=2.9, 2.1, H-4'); 4.06 (bdd, 1H, J$_{3',4'}$=9.1, J$_{3',OH}$=4.6, H-3'); 5.11-5.17 (bm, 3H, OH-2',3',5'); 6.19 (bs, 2H, NH$_2$); 6.27 (s, 1H, H-1'); 7.52 (m, 1H, H-6-naphth); 7.55 (m, 1H, H-7-naphth); 7.62 (dd, 1H, J$_{3,4}$=8.5, J$_{3,1}$=1.8, H-3-naphth); 7.81 (s, 1H, H-6); 7.94-7.97 (m, 3H, H-1,5,8-naphth); 8.01 (d, 1H, J$_{4,3}$=8.5, H-4-naphth); 8.18 (s, 1H, H-2). $^{13}$C NMR (125.7 MHz, DMSO-d$_6$): 20.03 (CH$_3$); 59.66 (CH$_2$-5'); 72.08 (CH-3'); 78.90 (C-2'); 82.41 (CH-4'); 90.57 (CH-1'); 100.24 (C-4a); 116.45 (C-5); 121.14 (C-6); 126.10 (CH-6-naphth); 126.76 (CH-7-naphth); 126.82 (CH-1-naphth); 127.23 (CH-3-naphth); 127.87 and 128.02 (CH-5,8-naphth); 128.70 (CH-4-naphth); 132.00 (C-4a-naphth); 132.35 (C-1-naphth); 133.46 (C-8a-naphth); 150.82 (C-7a); 152.02 (CH-2); 157.61 (C-4). IR (KBr): 3506, 3481, 3452, 3402, 3325, 3242, 3210, 3110, 3052, 2973, 1645, 1624, 1605, 1587, 1567, 1535, 1503, 1469, 1378, 1298, 1274, 1142, 1128, 1116, 1075, 1057, 1050, 1019, 897, 860, 821, 796, 767, 750, 478. MS (ESI) m/z 407 (M+H), 429 (M+Na). HRMS (ESI) for C$_{22}$H$_{23}$N$_4$O$_4$ [M+H] calcd: 407.1714; found: 407.1715. Anal. Calcd for C$_{22}$H$_{22}$N$_4$O$_4$·1.3H$_2$O: C, 61.47; H, 5.77; N, 13.03. Found: C, 61.83; H, 5.51; N, 12.65.

Example 24

4-Amino-5-(furan-2-yl)-7-(2-C-methyl-β-D-ribofuranosyl)-7H-pyrrolo[2,3-d]pyrimidine (7e)

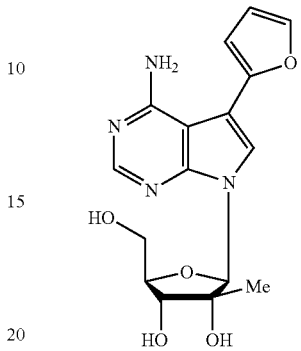

Title compound was prepared by following the procedure in Example 20, Step 3. White solid. Yield 55%. Mp 130° C. [α]$^{20}_D$ −53.3 (c 0.250, MeOH). $^1$H NMR (600 MHz, DMSO-d$_6$): 0.72 (s, 3H, CH$_3$); 3.68 and 3.85 (2×bd, 2H, J$_{gem}$=12.0, H-5'); 3.87 (ddd, 1H, J$_{4',3'}$=9.1, J$_{4',5'}$=2.9, 2.0, H-4'); 4.00 (bd, 1H, J$_{3',4'}$=9.1, H-3'); 5.16 (bs, 2H, OH-2',3'); 5.25 (bs, 1H, OH-5'); 6.19 (s, 1H, H-1'); 6.58 (dd, 1H, J$_{3,4}$=3.3, J$_{3,5}$=0.8, H-3-furyl); 6.60 (dd, 1H, J$_{4,3}$=3.3, J$_{4,5}$=1.9, H-4-furyl); 6.90 (bs, 2H, NH$_2$); 7.78 (dd, 1H, J$_{5,4}$=1.9, J$_{5,3}$=0.8, H-5-furyl); 8.01 (s, 1H, H-6); 8.14 (s, 1H, H-2). $^{13}$C NMR (151 MHz, DMSO-d$_6$): 19.91 (CH$_3$); 59.66 (CH$_2$-5'); 71.92 (CH-3'); 78.85 (C-2'); 82.48 (CH-4'); 90.60 (CH-1'); 99.03 (C-4a); 105.22 (CH-3-furyl); 106.10 (C-5); 112.13 (CH-4-furyl); 120.07 (CH-6); 142.17 (CH-5-furyl); 148.98 (C-2-furyl); 150.60 (C-7a); 152.35 (CH-2); 157.46 (C-4). IR (KBr): 3474, 3385, 3351, 3245, 3200, 1630, 1575, 1560, 1531, 1497, 1472, 1455, 1379, 1299, 1124, 1072, 1049, 1016, 893, 795, 594. MS (ESI) m/z 347 (M+H), 369 (M+Na). HRMS (ESI) for C$_{16}$H$_{19}$N$_4$O$_5$ [M+H] calcd: 347.1355; found: 347.1347. Anal. Calcd for C$_{16}$H$_{18}$N$_4$O$_5$·0.7H$_2$O: C, 53.54; H, 5.45; N, 15.61. Found: C, 53.86; H, 5.48; N, 15.22.

Example 25

4-Amino-7-(2-C-methyl-β-D-ribofuranosyl)-5-(thiophen-2-yl)-7H-pyrrolo[2,3-d]pyrimidine (7f)

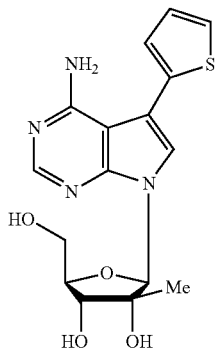

Title compound was prepared by following the procedure in Example 20, Step 3. White solid. Yield 77%. Mp 131° C. $[\alpha]^{20}_D$ −51.4 (c 0.255, MeOH). $^1$H NMR (600 MHz, DMSO-$d_6$): 0.73 (s, 3H, CH$_3$); 3.65 (dd, 1H, $J_{gem}$=12.3, $J_{5'b,4'}$=2.9, H-5'b); 3.83 (dd, 1H, $J_{gem}$=12.3, $J_{5'a,4'}$=2.1, H-5'a); 3.86 (ddd, 1H, $J_{4',3'}$=9.1, $J_{4',5'}$=2.9, 2.1, H-4'); 4.00 (bd, 1H, $J_{3',4'}$=9.1, H-3'); 5.20 (bs, 3H, OH-2',3',5'); 6.19 (s, 1H, H-1'); 6.30 (bs, 2H, NH$_2$); 7.13 (dd, 1H, $J_{3,4}$=3.5, $J_{3,5}$=1.2, H-3-thienyl); 7.16 (dd, 1H, $J_{4',5'}$=5.2, $J_{4,3}$=3.5, H-4-thienyl); 7.55 (dd, 1H, $J_{5,4}$=5.2, $J_{5,3}$=1.1, H-2-thienyl); 7.82 (s, 1H, H-6); 8.16 (s, 1H, H-2). $^{13}$C NMR (151 MHz, DMSO-$d_6$): 19.96 (CH$_3$); 59.37 (CH$_2$-5'); 71.76 (CH-3'); 78.88 (C-2'); 82.38 (CH-4'); 90.53 (CH-1'); 100.27 (C-4a); 108.51 (C-5); 121.64 (CH-6); 125.93 (CH-5-thienyl); 126.42 (CH-3-thienyl); 128.53 (CH-4-thienyl); 136.04 (C-2-thienyl); 150.40 (C-7a); 152.26 (CH-2); 157.47 (C-4). IR (KBr): 3471, 3380, 3350, 3235, 3195, 1622, 1591, 1575, 1549, 1507, 1460, 1430, 1372, 1349, 1296, 1228, 1122, 1071, 1050, 850, 796, 707, 559. MS (ESI) m/z 363 (M+H), 385 (M+Na). HRMS (ESI) for C$_{16}$H$_{19}$N$_4$O$_4$S [M+H] calcd: 363.1127; found: 363.1121. Anal. Calcd for C$_{16}$H$_{18}$N$_4$O$_4$S·0.95H$_2$O: C, 50.64; H, 5.28; N, 14.76. Found: C, 51.03; H, 5.06; N, 14.40.

Example 26

4-Amino-5-(furan-3-yl)-7-(2-C-methyl-β-D-ribofuranosyl)-7H-pyrrolo[2,3-d]pyrimidine (7g)

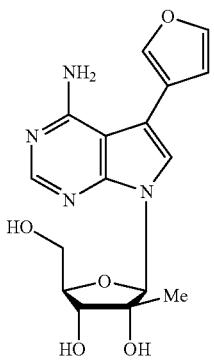

Title compound was prepared by following the procedure in Example 20, Step 3. Reaction time 2.5 h. White solid. Yield 59%. Mp 123° C. $[\alpha]^{20}_D$ −54.5 (c 0.217, MeOH). $^1$H NMR (600 MHz, DMSO-$d_6$): 0.72 (s, 3H, CH$_3$); 3.65 (dd, 1H, $J_{gem}$=12.2, $J_{5'b,4'}$=3.0, H-5'b); 3.82 (dd, 1H, $J_{gem}$=12.2, $J_{5'a,4'}$=2.1, H-5'a); 3.85 (ddd, 1H, $J_{3',4'}$=9.1, $J_{4',5'}$=3.0, 2.1, H-4'); 3.99 (d, 1H, $J_{3',4'}$=9.1, H-3'); 5.16 (bs, 3H, OH-2',3',5'); 6.19 (s, 1H, H-1'); 6.25 (bs, 2H, NH$_2$); 6.66 (dd, 1H, $J_{4,5}$=1.7, $J_{4,2}$=0.8, H-4-furyl); 7.65 (s, 1H, H-6); 7.79 (t, 1H, $J_{5,2}$=$J_{5,4}$=1.7, H-5-furyl); 7.80 (dd, 1H, $J_{2,5}$=1.7, $J_{2,4}$=0.8, H-2-furyl); 8.13 (s, 1H, H-2). $^{13}$C NMR (151 MHz, DMSO-$d_6$): 19.99 (CH$_3$); 59.74 (CH$_2$-5'); 72.08 (CH-3'); 78.87 (C-2'); 82.41 (CH-4'); 90.56 (CH-1'); 100.67 (C-4a); 106.27 (C-5); 111.78 (CH-4-furyl); 119.00 (C-3-furyl); 120.61 (CH-6); 139.79 (CH-2-furyl); 144.43 (CH-5-furyl); 150.52 (C-7a); 152.03 (CH-2); 157.68 (C-4). IR (KBr): 3478, 3337, 3243, 3208, 3150, 1623, 1583, 1561, 1534, 1498, 1455, 1378, 1357, 1350, 1300, 1159, 1120, 1071, 1056, 1026, 874, 793, 602. MS (ESI) m/z 347 (M+H). HRMS (ESI) for C$_{16}$H$_{19}$N$_4$O$_5$ [M+H] calcd: 347.1350; found: 347.1349. Anal. Calcd for C$_{16}$H$_{18}$N$_4$O$_5$·1.7H$_2$O: C, 50.98; H, 5.72; N, 14.86. Found: C, 51.30; H, 5.33; N, 14.46.

Example 27

4-Amino-7-(2-C-methyl-β-D-ribofuranosyl)-5-(thiophen-3-yl)-7H-pyrrolo[2,3-d]pyrimidine (7h)

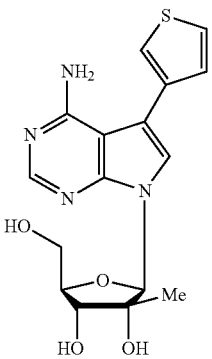

Title compound was prepared by following the procedure in Example 20, Step 3. White solid. Yield 62%. Mp 128° C. $[\alpha]^{20}_D$ −60.3 (c 0.222, MeOH). $^1$H NMR (600 MHz, DMSO-$d_6$): 0.74 (s, 3H, CH$_3$); 3.65 (ddd, 1H, $J_{gem}$=12.1, $J_{5'b,OH}$=4.8, $J_{5'b,4'}$=2.9, H-5'b); 3.82 (ddd, 1H, $J_{gem}$=12.1, $J_{5'a,OH}$=4.8, $J_{5'a,4'}$=2.1, H-5'a); 3.85 (ddd, 1H, $J_{4',3'}$=9.0, $J_{4',5'}$=2.9, 2.1, H-4'); 4.00 (dd, 1H, $J_{3',4'}$=9.0, $J_{3',OH}$=7.1, H-3'); 5.12 (d, 1H, $J_{OH,3'}$=7.1, OH-3'); 5.13 (s, 1H, OH-2'); 5.16 (t, 1H, $J_{OH,5'}$=4.8, OH-5'); 6.20 (s, 1H, H-1'); 6.20 (bs, 2H, NH$_2$); 7.24 (dd, 1H, $J_{4,5}$=4.9, $J_{4,2}$=1.4, H-4-thienyl); 7.49 (dd, 1H, $J_{2,5}$=2.9, $J_{2,4}$=1.4, H-2-thienyl); 7.698 (dd, 1H, $J_{5,4}$=4.9, $J_{5,2}$=2.9, H-5-thienyl); 7.70 (s, 1H, H-6); 8.14 (s, 1H, H-2). $^{13}$C NMR (151 MHz, DMSO-$d_6$): 20.01 (CH$_3$); 59.67 (CH$_2$-5'); 72.04 (CH-3'); 78.89 (C-2'); 82.41 (CH-4'); 90.55 (CH-1'); 100.44 (C-4a); 111.08 (C-5); 120.73 (CH-6); 122.11 (CH-2-thienyl); 127.66 (CH-5-thienyl); 128.72 (CH-4-thienyl); 135.16 (C-3-thienyl); 150.38 (C-7a); 151.96 (CH-2); 157.57 (C-4). IR (KBr): 3475, 3351, 3240, 3200, 3120, 3107, 1621, 1594, 1575, 1549, 1510, 1465, 1409, 1378, 1346, 1297, 1139, 1123, 1072, 1045, 861, 788. MS (ESI) m/z 363 (M+H), 385 (M+Na). HRMS (ESI) for C$_{16}$H$_{19}$N$_4$O$_4$S [M+H] calcd: 363.1122; found: 363.1122. Anal. Calcd for C$_{16}$H$_{18}$N$_4$O$_4$S·1.1H$_2$O: C, 50.28; H, 5.33; N, 14.66. Found: C, 50.42; H, 5.20; N, 14.45.

Example 28

4-Amino-5-(benzofuran-2-yl)-7-(2-C-methyl-β-D-ribofuranosyl)-7H-pyrrolo[2,3-d]pyrimidine (7i)

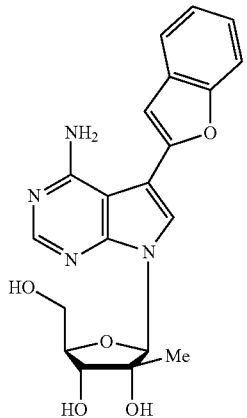

Title compound was prepared by following the procedure in Example 20, Step 3. White solid. Yield 66%. Mp 248° C. (dec.). $[\alpha]^{20}_D$ −55.0 (c 0.220, MeOH). $^1$H NMR (500 MHz, DMSO-$d_6$): 0.76 (s, 3H, CH$_3$); 3.72 (ddd, 1H, $J_{gem}$=12.5, $J_{5'b,OH}$=5.0, $J_{5'b,4'}$=2.9, H-5130); 3.88 (ddd, 1H, $J_{gem}$=12.5, $J_{5'a,OH}$=5.0, $J_{5'a,4'}$=2.0, H-5'a); 3.90 (ddd, 1H, $J_{4',3'}$=9.2, $J_{4',5'}$=2.9, 2.0, H-4'); 4.04 (dd, 1H, $J_{3',4'}$=9.2, $J_{3',OH}$=7.0, H-3'); 5.17 (d, 1H, $J_{OH,3'}$=7.0, OH-3'); 5.19 (s, 1H, OH-2'); 5.28 (t, 1H, $J_{OH,5'}$=5.0, OH-5'); 6.23 (s, 1H, H-1); 6.98 (bs, 2H, NH$_2$); 7.04 (d, 1H, $J_{3,7}$=1.0, H-3-benzofuryl); 7.27 (td, 1H, $J_{5,4}$=$J_{5,6}$=7.3, $J_{5,7}$=1.4, H-5-benzofuryl); 7.29 (td, 1H, $J_{6,5}$=$J_{6,7}$=7.3, $J_{6,4}$=1.7, H-6-benzofuryl); 7.61-7.67 (m, 2H, H-4,7-benzofuryl); 8.19 (s, 1H, H-2); 8.26 (s, 1H, H-6). $^{13}$C NMR (125.7 MHz, DMSO-$d_6$): 19.96 (CH$_3$); 59.72 (CH$_2$-5'); 71.97 (CH-3'); 78.91 (C-2'); 82.59 (CH-4'); 90.74 (CH-1); 99.19 (C-4a); 101.58 (CH-3-benzofuryl); 105.47 (C-5); 111.30 (CH-7-benzofuryl); 120.81 (CH-4-benzofuryl); 122.32 (CH-6); 123.73 (CH-5-benzofuryl); 124.08 (CH-6-benzofuryl); 129.01 (C-3a-benzofuryl); 150.94 (C-7a); 151.45 (C-2-benzofuryl); 152.58 (CH-2); 154.00 (C-7a-benzofuryl); 157.50 (C-4). MS (ESI, negative mode) m/z 395 (M−H). HRMS (ESI, negative mode) for $C_{20}H_{19}N_4O_5$: [M−H] calcd: 395.1350; found: 395.1358. Anal. Calcd for $C_{20}H_{20}N_4O_5 \cdot \frac{1}{3}H_2O$: C, 59.70; H, 5.18; N, 13.92. Found: C, 59.98; H, 5.13; N, 13.46.

Example 29

4-Amino-5-phenyl-7-(β-D-ribofuranosyl)-7H-pyrrolo[2,3-d]pyrimidine 5'-O-triphosphate sodium salt (13a)

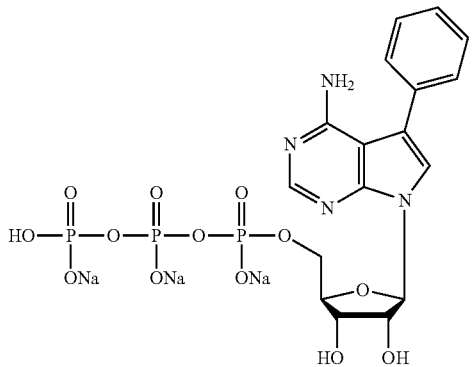

Step 1. 4-Amino-5-iodo-7-(β-D-ribofuranosyl)-7H-pyrrolo[2,3-d]pyrimidine 5'-O-triphosphate sodium salt (11)

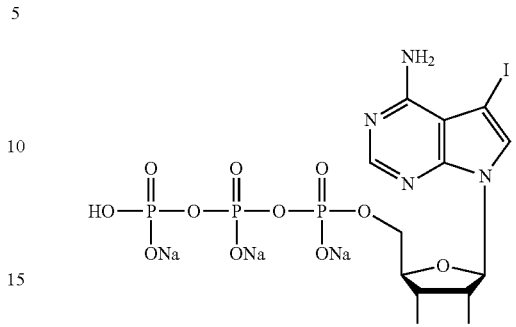

Phosphorus oxychloride (45 µl, 0.49 mmol) was dropwise added to a stirred mixture of 7-iodotubericidine 1 (150 mg, 0.38 mmol) in trimethyl phosphate (1 ml) at 0° C. and the solution was stirred at 0° C. for 1.25 h. A freshly prepared solution of bis(tri-n-butylammonium) pyrophosphate (1.05 g, 1.91 mmol) and tri-n-butylamine (0.4 ml, 1.66 mmol) in dry DMF (4 ml) was stirred with molecular sieves at 0° C. for at least 15 min and then added to the stirred reaction mixture at 0° C. The mixture was held at the same temperature for 1.5 h before being quenched with aq TEAB (2M, 1.2 ml). Volatiles were removed in vacuo and the rest was several times co-evaporated with water. The residue was purified by ion-exchange chromatography on DEAE-Sephadex (0→60% 2M aq TEAB in $H_2O$) and obtained triethylammonium salt of product was converted to sodium salt by passing through column of Dowex 50 (Na$^+$ form). Lyophilization afforded title compound 11 as a white cotton (131 mg, 48%). $^1$H NMR (500 MHz, $D_2O$+phosphate buffer, pH=7.1, ref$_{dioxane}$=3.75 ppm): 4.15 (ddd, 1H, $J_{gem}$=11.6, $J_{H,P}$=4.9, $J_{5'b,4'}$=3.3, H-5'b); 4.24 (ddd, 1H, $J_{gem}$=11.6, $J_{H,P}$=6.6, $J_{5'a,4'}$=3.2, H-5'a); 4.34 (m, 1H, $J_{4',5'}$=3.3, 3.2, $J_{4',3'}$=2.9, $J_{H,P}$=2.1, H-4'); 4.54 (ddd, 1H, $J_{3',2'}$=5.3, $J_{3',4'}$=2.9, $J_{H,P}$=0.4, H-3'); 4.65 (dd, 1H, $J_{2',1'}$=6.7, $J_{2',3'}$=5.3, H-2'); 6.21 (d, 1H, $J_{1',2'}$=6.7, H-1'); 7.71 (s, 1H, H-8); 8.09 (s, 1H, H-2). $^{13}$C NMR (125.7 MHz, $D_2O$+phosphate buffer, pH=7.1, ref$_{dioxane}$=69.3 ppm): 55.01 (C-7); 68.18 (d, $J_{C,P}$=6, CH$_2$-5'); 73.21 (CH-3'); 76.51 (CH-2'); 86.33 (d, $J_{C,P}$=9, CH-4'); 88.50 (CH-1'); 106.76 (C-4a); 129.78 (CH-6); 152.52 (C-7a); 154.17 (CH-2); 159.72 (C-4). $^{31}$P ($^1$H dec.) NMR (202.4 MHz, $D_2O$+phosphate buffer, pH=7.1, ref$_{H3PO4}$=0 ppm): −20.78 (t, J=19.5, $P_β$); −9.66 (d, J=19.5, $P_α$); −7.00 (d, J=19.5, $P_γ$). MS (ESI) m/z 699 (M+H), 721 (M+Na). MS (ESI, negative mode) m/z 631 (M−3Na+2H), 653 (M−2Na+H), 675 (M−Na). HRMS (ESI, negative mode)$^-$ for $C_{11}H_{14}IN_4NaO_{13}P_3$ [M−2Na+H] calcd: 652.8713; found: 652.8731.

Step 2. 4-Amino-5-phenyl-7-(β-D-ribofuranosyl)-7H-pyrrolo[2,3-d]pyrimidine 5'-O-triphosphate sodium salt (13a)

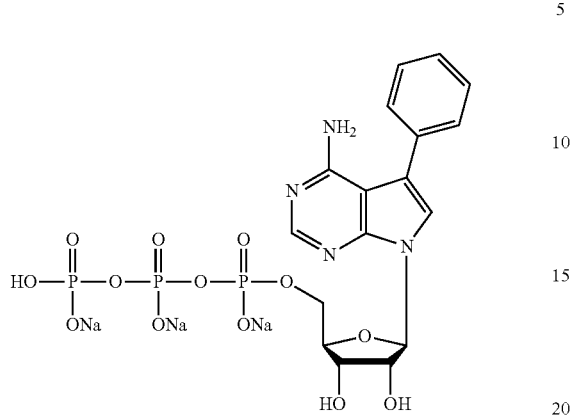

An an argon purged mixture of Pd(OAc)$_2$ (1.5 mg, 6.7 μmop and TPPTS (17.3 mg, 30 μmop in water/MeCN (2:1, 1.2 ml) was sonicated to full dissolution and quarter of this pre-prepared solution (0.3 ml, ¼ of total amount) was added to an argon purged mixture of compound 11 from Step 1 (20.1 mg, 29 μmol), phenylboronic acid (5.2 mg, 42 μmol), Cs$_2$CO$_3$ (27 mg, 83 μmol) in water/MeCN (2:1, 0.6 ml) and the mixture was stirred at 110° C. for 30 min. After cooling, the mixture was filtered through microfilter and separated by HPLC on C-18 phase (0→100% MeOH in 0.1M aq TEAB) affording after ion exchange on Dowex 50 (Na$^+$ form) and lyophilization title compound 13a as white cotton (8.6 mg, 46%). $^1$H NMR (500 MHz, D$_2$O+phosphate buffer, pH=7.1, ref$_{dioxane}$=3.75 ppm): 4.14 (ddd, 1H, J$_{gem}$=11.6, J$_{H,P}$=4.7, J$_{5'b,4'}$=3.5, H-5'b); 4.25 (ddd, 1H, J$_{gem}$=11.6, J$_{H,P}$=6.5, J$_{5'a,4'}$=3.3, H-5'a); 4.35 (m, 1H, J$_{4',5'}$=3.5, 3.3, J$_{4',3'}$=2.9, J$_{H,P}$=1.7, H-4'); 4.57 (dd, 1H, J$_{3',2'}$=5.4, J$_{3',4'}$=2.9, H-3'); 4.73 (dd, 1H, J$_{2',1'}$=6.9, J$_{2',3'}$=5.4, H-2'); 6.30 (d, 1H, J$_{1',2'}$=6.9, H-1'); 7.45 (m, 1H, H-p-Ph); 7.49-7.56 (m, 4H, H-o,m-Ph); 7.57 (s, 1H, H-6); 8.16 (s, 1H, H-2). $^{13}$C NMR (125.7 MHz, D$_2$O+phosphate buffer, pH=7.1, ref$_{dioxane}$=69.3 ppm): 68.22 (d, J$_{C,P}$=5, CH$_2$-5'); 73.26 (CH-3'); 76.24 (CH-2'); 86.31 (d, J$_{C,P}$=9, CH-4'); 88.34 (CH-1'); 103.75 (C-4a); 121.56 (C-5); 122.86 (CH-6); 130.41 (CH-p-Ph); 131.59 and 131.94 (CH-o,m-Ph); 136.10 (C-i-Ph); 153.15 (C-7a); 153.67 (CH-2); 159.61 (C-4). $^{31}$P ($^1$H dec.) NMR (202.4 MHz, D$_2$O+phosphate buffer, pH=7.1, ref$_{H3PO4}$=0 ppm): −21.32 (dd, J=19.3, 19.0, P$_β$); −10.45 (d, J=19.3, P$_α$); −6.98 (d, J=19.0, P$_γ$). MS (ESI, negative mode) m/z 581 (M−3Na+2H), 603 (M−2Na+H), 625 (M−Na). HRMS (ESI, negative mode)$^-$ for C$_{17}$H$_{20}$N$_4$O$_{13}$P$_3$ [M−3Na+2H] calcd: 581.0240; found: 581.0253.

Example 30

4-Amino-5-(4-fluorophenyl)-7-(β-D-ribofuranosyl)-7H-pyrrolo[2,3-d]pyrimidine 5'-O-triphosphate sodium salt (13b)

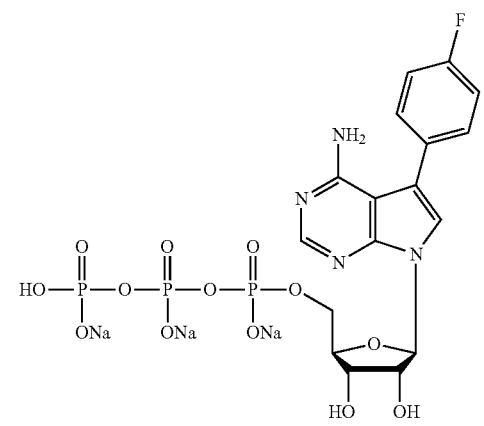

Title compound was prepared by following the procedure in Example 29, Step 2. White cotton. Yield 25%. $^1$H NMR (500 MHz, D$_2$O+phosphate buffer, pH=7.1, ref$_{dioxane}$=3.75 ppm): 4.13 (dt, 1H, J$_{gem}$=11.4, J$_{H,P=J5'b,4'}$=4.2, H-5'b); 4.25 (ddd, 1H, J$_{gem}$=11.4, J$_{H,P}$=6.5, J$_{5'a,4'}$=3.3, H-5'a); 4.35 (bddd, 1H, J$_{4',5'}$=4.2, 3.3, J$_{4',3'}$=2.7, H-4'); 4.58 (dd, 1H, J$_{3',2'}$=5.4, J$_{3',4'}$=2.7, H-3'); 4.72 (dd, 1H, J$_{2',1'}$=6.9, J$_{2',3'}$=5.4, H-2'); 6.31 (d, 1H, J$_{1',2'}$=6.9, H-1'); 7.24 (m, 2H, H-m-C$_6$H$_4$F); 7.53 (m, 2H, H-o-C$_6$H$_4$F); 7.56 (s, 1H, H-6); 8.17 (s, 1H, H-2). $^{13}$C NMR (125.7 MHz, D$_2$O+phosphate buffer, pH=7.1, ref$_{dioxane}$=69.3 ppm): 68.19 (d, J$_{C,P}$=6, CH$_2$-5'); 73.26 (CH-3'); 76.21 (CH-2'); 86.34 (d, J$_{C,P}$=9, CH-4'); 88.26 (CH-1'); 103.93 (C-4a); 118.57 (d, J$_{C,F}$=22, CH-m-C$_6$H$_4$F); 120.54 (C-5); 122.83 (CH-6); 132.26 (d, J$_{C,F}$=3, C-i-C$_6$H$_4$F); 133.44 (d, J$_{C,F}$=8, CH-o-C$_6$H$_4$F); 153.24 (C-7a); 154.16 (CH-2); 159.98 (C-4); 164.95 (d, J$_{C,F}$=244, C-p-C$_6$H$_4$F). $^{31}$P ($^1$H dec.) NMR (202.4 MHz, D$_2$O+phosphate buffer, pH=7.1, ref$_{H3PO4}$=0 ppm): −21.04 (dd, J=18.9, 18.4, P$_β$); −10.39 (d, J=18.9, P$_α$); −6.12 (d, J=18.4, P$_γ$). MS (ESI, negative mode) m/z 621 (M−2Na+H), 643 (M−Na). HRMS (ESI, negative mode) for C$_{17}$H$_{17}$FN$_4$Na$_2$O$_{13}$P$_3$ [M−Na] calcd: 642.9779; found: 642.9789.

Example 31

4-Amino-5-(furan-2-yl)-7-(β-D-ribofuranosyl)-7H-pyrrolo[2,3-d]pyrimidine 5'-O-triphosphate sodium salt (13c)

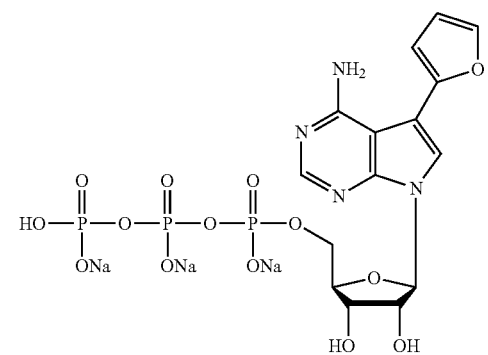

Title compound was prepared by following the procedure in Example 29, Step 2. Re-purification by ion-exchange HPLC on Poros HQ (TEAB gradient) after HPLC on C-18. White cotton. Yield 27%. $^1$H NMR (500 MHz, D$_2$O+ phosphate buffer, pH=7.1, ref$_{dioxane}$=3.75 ppm): 4.19 (ddd, 1H, J$_{gem}$=11.7, J$_{H,P}$=4.7, J$_{5'b,4'}$=3.2, H-5'b); 4.28 (ddd, 1H, J$_{gem}$=11.7, J$_{H,P}$=6.2, J$_{5'a,4'}$=2.8, H-5'a); 4.36 (ddd, 1H, J$_{4',5'}$=3.2, 2.8, J$_{4',3'}$=2.9, H-4'); 4.59 (dd, 1H, J$_{3',2'}$=5.2, J$_{3',4'}$=2.9, H-3'); 4.71 (dd, 1H, J$_{2',1'}$=6.6, J$_{2',3'}$=5.2, H-2'); 6.25 (d, 1H, J$_{1',2'}$=6.6, H-1'); 6.57 (dd, 1H, J$_{4,3}$=3.4, J$_{4,5}$=1.9, H-4-furyl); 6.75 (dd, 1H, J$_{3,4}$=3.4, J$_{3,5}$=0.7, H-3-furyl); 7.57 (dd, 1H, J$_{5,4}$=1.9, J$_{5,3}$=0.7, H-5-furyl); 7.84 (s, 1H, H-6); 8.08 (s, 1H, H-2). $^{13}$C NMR (125.7 MHz, D$_2$O+phosphate buffer, pH=7.1, ref$_{dioxane}$=69.3 ppm): 68.14 (d, J$_{C,P}$=5, CH$_2$-5'); 73.28 (CH-3'); 76.60 (CH-2'); 86.40 (d, J$_{C,P}$=9, CH-4'); 88.60 (CH-1'); 102.45 (C-4a); 108.95 (CH-3-furyl); 111.18 (C-5); 114.80 (CH-4-furyl); 122.05 (CH-6); 144.63 (CH-5-furyl); 150.34 (C-2-furyl); 152.81 (C-7a); 153.46 (CH-2); 159.28 (C-4). $^{31}$P ($^1$H dec.) NMR (202.4 MHz, D$_2$O+ phosphate buffer, pH=7.1, ref$_{H3PO4}$=0 ppm): −21.09 (dd, J=19.2, 18.7, P$_\beta$); −10.43 (d, J=19.2, P$_\alpha$); −6.25 (d, J=18.7, P$_\gamma$). MS (ESI, negative mode) m/z 593 (M−2Na+H), 615 (M−Na). HRMS (ESI, negative mode) for C$_{15}$H$_{17}$N$_4$NaO$_{14}$P$_3$ [M−2Na+H] calcd: 592.9846; found: 592.9868; for C$_{15}$H$_{16}$N$_4$Na$_2$O$_{14}$P$_3$ [M−Na] calcd: 614.9666; found: 614.9686; for C$_{15}$H$_{14}$N$_4$Na$_4$O$_{14}$P$_3$ [M−2H+Na] calcd: 658.9310; found: 658.9321.

Example 32

4-Amino-7-(β-D-ribofuranosyl)-5-(thiophen-2-yl)-7H-pyrrolo[2,3-d]pyrimidine 5'-O-triphosphate sodium salt (13d)

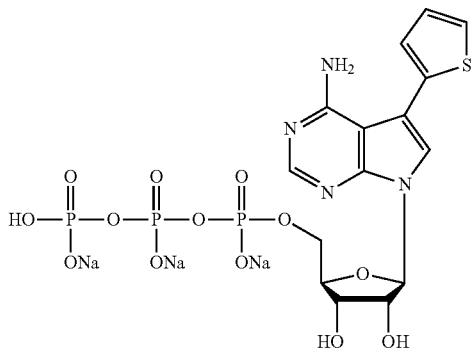

Title compound was prepared by following the procedure in Example 29, Step 2. White solid. Yield 53%. $^1$H NMR (500 MHz, D$_2$O+phosphate buffer, pH=7.1, ref$_{dioxane}$=3.75 ppm): 4.14 (ddd, 1H, J$_{gem}$=11.7, J$_{H,P}$=4.9, J$_{5'b,4'}$=3.6, H-5'b); 4.28 (ddd, 1H, J$_{gem}$=11.7, J$_{H,P}$=6.9, J$_{5'a,4'}$=3.6, H-5'a); 4.35 (td, 1H, J$_{4',5'}$=3.6, J$_{4',3'}$=2.7, H-4'); 4.58 (dd, 1H, J$_{3',2'}$=5.3, J$_{3',4'}$=2.7, H-3'); 4.73 (dd, 1H, J$_{2',1'}$=7.1, J$_{2',3'}$=5.3, H-2'); 6.30 (d, 1H, J$_{1',2'}$=7.1, H-1'); 7.21 (dd, 1H, J$_{4,5}$=5.0, J$_{4,3}$=3.5, H-4-thienyl); 7.22 (dd, 1H, J$_{3,4}$=3.5, J$_{3,5}$=1.4, H-3-thienyl); 7.51 (dd, 1H, J$_{5,4}$=5.0, J$_{5,3}$=1.4, H-5-thienyl); 7.64 (s, 1H, H-6); 8.18 (s, 1H, H-2). $^{13}$C NMR (125.7 MHz, D$_2$O+ phosphate buffer, pH=7.1, ref$_{dioxane}$=69.3 ppm): 68.20 (d, J$_{C,P}$=5, CH$_2$-5'); 73.22 (CH-3'); 76.21 (CH-2'); 86.40 (d, J$_{C,P}$=9, CH-4'); 88.28 (CH-1'); 104.13 (C-4a); 113.58 (C-5); 123.93 (CH-6); 129.26 (CH-5-thienyl); 130.14 (CH-3-thienyl); 130.95 (CH-4-thienyl); 137.11 (C-2-thienyl); 153.14 (C-7a); 154.52 (CH-2); 160.04 (C-4). $^{31}$P ($^1$H dec.) NMR (202.4 MHz, D$_2$O+phosphate buffer, pH=7.1, ref$_{H3PO4}$=0 ppm): −21.12 (bdd, J=20.5, 19.4, P$_\beta$); −10.41 (d, J=19.4, P$_\alpha$); −6.23 (d, J=20.5, P$_\gamma$). MS (ESI, negative mode) m/z 609 (M−2Na+H), 631 (M−Na). HRMS (ESI, negative mode) for C$_{15}$H$_{17}$N$_4$NaO$_{13}$P$_3$S [M−2Na+H] calcd: 608.9618; found: 608.9637.

Example 33

4-Amino-5-(furan-3-yl)-7-(β-D-ribofuranosyl)-7H-pyrrolo[2,3-d]pyrimidine 5'-O-triphosphate sodium salt (13e)

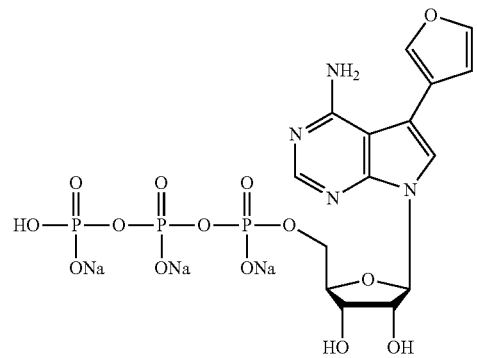

Title compound was prepared by following the procedure in Example 29, Step 2. Re-purification by ion-exchange HPLC on Poros HQ (TEAB gradient) after HPLC on C-18. Pale yellow solid. Yield 37%. $^1$H NMR (600 MHz, D$_2$O+ phosphate buffer, pH=7.1, ref$_{dioxane}$=3.75 ppm): 4.14 (ddd, 1H, J$_{gem}$=11.2, J$_{H,P}$=4.9, J$_{5'b,4'}$=2.9, H-5'b); 4.25 (ddd, 1H, J$_{gem}$=11.2, J$_{H,P}$=6.4, J$_{5'a,4'}$=3.1, H-5'a); 4.35 (ddd, 1H, J$_{4',5'}$=3.2, 2.9, J$_{4',3'}$=2.4, H-4'); 4.57 (dd, 1H, J$_{3',2'}$=5.4, J$_{3',4'}$=2.4, H-3'); 4.73 (dd, 1H, J$_{2',1'}$=6.9, J$_{2',3'}$=5.4, H-2'); 6.29 (d, 1H, J$_{1',2'}$=6.9, H-1'); 6.73 (dd, 1H, J$_{4,5}$=1.9, J$_{4,2}$=0.9, H-4-furyl); 7.58 (s, 1H, H-6); 7.65 (dd, 1H, J$_{5,4}$=1.9, J$_{5,2}$=1.6, H-5-furyl); 7.75 (dd, 1H, J$_{2,5}$=1.6, J$_{2,4}$=0.9, H-2-furyl); 8.16 (s, 1H, H-2). $^{13}$C NMR (151 MHz, D$_2$O+ phosphate buffer, pH=7.1, ref$_{dioxane}$=69.3 ppm): 68.22 (d, J$_{C,P}$=5, CH$_2$-5'); 73.32 (CH-3'); 76.22 (CH-2'); 86.35 (d, J$_{C,P}$=9, CH-4'); 88.24 (CH-1'); 104.39 (C-4a); 111.40 (C-5); 114.18 (CH-4-furyl); 120.38 (C-3-furyl); 122.84 (CH-6); 143.14 (CH-2-furyl); 147.03 (CH-5-furyl); 153.22 (C-7a); 154.35 (CH-2); 160.22 (C-4). $^{31}$P ($^1$H dec.) NMR (202.4 MHz, D$_2$O+phosphate buffer, pH=7.1, ref$_{H3PO4}$=0 ppm): −20.54 (bdd, J=17.8, 15.0, P$_\beta$); −10.35 (d, J=17.8, P$_\alpha$); −5.66 (d, J=15.0, P$_\gamma$). MS (ESI, negative mode) m/z 593 (M−2Na+H), 615 (M−Na). HRMS (ESI, negative mode) for C$_{15}$H$_{16}$N$_4$Na$_2$O$_{14}$P$_3$ [M−Na] calcd: 614.9666; found: 614.9678.

Example 34

4-Amino-7-(β-D-ribofuranosyl)-5-(thiophen-3-yl)-7H-pyrrolo[2,3-d]pyrimidine 5'-O-triphosphate sodium salt (13f)

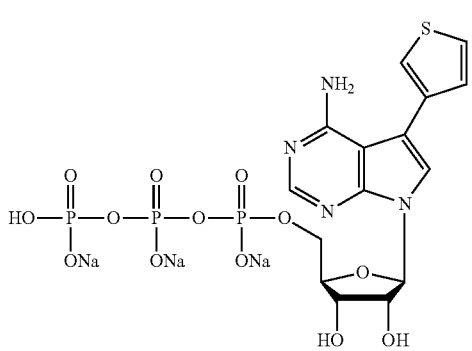

Title compound was prepared by following the procedure in Example 29, Step 2. White cotton. Yield 67%. $^1$H NMR (500 MHz, D$_2$O+phosphate buffer, pH=7.1, ref$_{dioxane}$=3.75 ppm): 4.14 (ddd, 1H, J$_{gem}$=11.6, J$_{H,P}$=4.8, J$_{5'b,4'}$=3.5, H-5'b); 4.25 (ddd, 1H, J$_{gem}$=11.6, J$_{H,P}$=6.6, J$_{5'a,4'}$=3.2, H-5'a); 4.35 (ddd, 1H, J$_{4',5'}$=3.5, 3.2, J$_{4',3'}$=2.7, H-4'); 4.58 (dd, 1H, J$_{3',2'}$=5.3, J$_{3',4'}$=2.7, H-3'); 4.74 (dd, 1H, J$_{2',1'}$=7.0, J$_{2',3'}$=5.3, H-2'); 6.30 (d, 1H, J$_{1',2'}$=7.0, H-1'); 7.33 (dd, 1H, J$_{4,5}$=5.0, J$_{4,2}$=1.4, H-4-thienyl); 7.52 (dd, 1H, J$_{2,5}$=3.0, J$_{2,4}$=1.4, H-2-thienyl); 7.607 (s, 1H, H-6); 7.610 (dd, 1H, J$_{5,4}$=5.0, J$_{5,2}$=3.0, H-5-thienyl); 8.17 (s, 1H, H-2). $^{13}$C NMR (125.7 MHz, D$_2$O+phosphate buffer, pH=7.1, ref$_{dioxane}$=69.3 ppm): 68.20 (d, J$_{C,P}$=5, CH$_2$-5'); 73.30 (CH-3'); 76.24 (CH-2'); 86.38 (d, J$_{C,P}$=9, CH-4'); 88.28 (CH-1'); 104.09 (C-4a); 116.08 (C-5); 122.81 (CH-6); 125.88 (CH-2-thienyl); 130.18 (CH-5-thienyl); 131.28 (CH-4-thienyl); 136.31 (C-3-thienyl); 153.09 (C-7a); 154.20 (CH-2); 160.06 (C-4). $^{31}$P ($^1$H dec.) NMR (202.4 MHz, D$_2$O+phosphate buffer, pH=7.1, ref$_{H3PO4}$=0 ppm): −21.14 (bdd, J=21.0, 19.3, P$_\beta$); −10.39 (d, J=19.3, P$_\alpha$); −6.45 (d, J=21.0, P$_\gamma$). MS (ESI, negative mode) m/z 609 (M−2Na+H), 631 (M−Na). HRMS (ESI, negative mode) for C$_{15}$H$_{17}$N$_4$NaO$_{13}$P$_3$S [M−2Na+H] calcd: 608.9618; found: 608.9635.

Example 35

4-Amino-5-phenyl-7-(β-D-ribofuranosyl)-7H-pyrrolo[2,3-d]pyrimidine 5'-O-monophosphate sodium salt (14a)

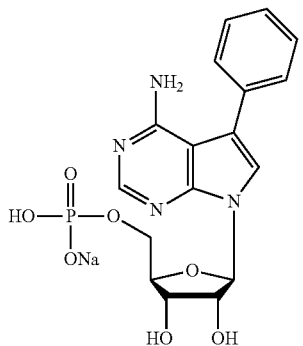

Step 1. 4-Amino-5-iodo-7-(β-D-ribofuranosyl)-7H-pyrrolo[2,3-d]pyrimidine 5'-O-monophosphate sodium salt (12)

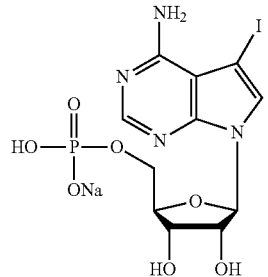

Phosphorus oxychloride (70 μl, 0.77 mmol) was dropwise added to a stirred mixture of 7-iodotubericidine 1 (250 mg, 0.64 mmol) in trimethyl phosphate (2 ml) at 0° C. and the solution was stirred at 0° C. for 2 h. The reaction was quenched by the addition of aq TEAB (2M, 2 ml) and after evaporation the rest was several times co-evaporated with water. The residue was purified by ion-exchange chromatography on DEAE-Sephadex (0→60% 2M aq TEAB in water) affording after ion-exchange on Dowex 50 (Na$^+$ form) and lyophilization title compound 12 as a white cotton (229 mg, 73% yield). $^1$H NMR (500 MHz, D$_2$O, ref$_{dioxane}$=3.75 ppm): 3.97 (dt, 1H, J$_{gem}$=11.4, J$_{H,P}$=4.0, H-5'b); 4.00 (ddd, 1H, J$_{gem}$=11.4, J$_{H,P}$=5.3, J$_{5'a,4'}$=3.7, H-5'a); 4.30 (m, 1H, J$_{4',5'}$=4.0, 3.7, J$_{4',3'}$=3.0, J$_{H,P}$=1.0, H-4'); 4.44 (dd, 1H, J$_{3',2'}$=5.4, J$_{3',4'}$=3.0, H-3'); 4.63 (dd, 1H, J$_{2',1'}$=6.7, J$_{2',3'}$=5.4, H-2'); 6.20 (d, 1H, J$_{1',2'}$=6.7, H-1'); 7.70 (s, 1H, H-6); 8.08 (s, 1H, H-2). $^{13}$C NMR (125.7 MHz, D$_2$O, ref$_{dioxane}$=69.3 ppm): 54.97 (C-5); 66.81 (d, J$_{C,P}$=5, CH$_2$-5'); 73.50 (CH-3'); 76.59 (CH-2'); 86.74 (d, J$_{C,P}$=9, CH-4'); 88.52 (CH-1'); 106.71 (C-4a); 129.72 (CH-6); 152.45 (C-7a); 154.24 (CH-2); 159.74 (C-4). $^{31}$P ($^1$H dec.) NMR (202.4 MHz, D$_2$O, ref$_{H3PO4}$=0 ppm): 3.24. MS (ESI, negative mode) m/z 471 (M−Na). HRMS (ESI, negative mode) for C$_{11}$H$_{13}$N$_4$IO$_7$P: [M−Na] calcd: 470.9561; found: 470.9576.

Step 2. 4-Amino-5-phenyl-7-(β-D-ribofuranosyl)-7H-pyrrolo[2,3-d]pyrimidine 5'-O-monophosphate sodium salt (14a)

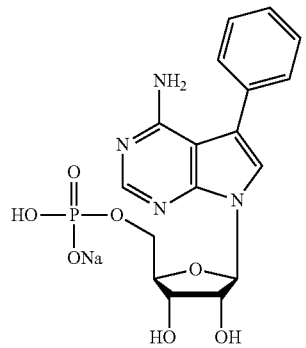

An argon purged mixture of Pd(OAc)$_2$ (1.7 mg, 7.6 μmol) and TPPTS (21.7 mg, 38 μmol) in water/MeCN (2:1, 1.6 ml) was sonicated to dissolution and quarter of resulting solution (0.4 ml, ¼ of total amount) was added to an argon purged mixture of compound 12 from Step 1 (17 mg, 34 μmol), phenylboronic acid (7.9 mg, 65 μmol) and Na$_2$CO$_3$ (17 mg, 160 μmol) in water/MeCN (2:1, 0.8 ml) and the mixture was stirred at 125° C. for 1.5 h. After cooling, the mixture was filtered through microfilter and purified by HPLC on C-18 phase (0→100% MeOH in 0.1M aq TEAB) affording after ion exchange on Dowex 50 (Na$^+$ form) and lyophilization title compound 14a as white solid (14.4 mg, 94%). $^1$H NMR (500 MHz, D$_2$O, ref$_{dioxane}$=3.75 ppm): 3.91 (dt, 1H, $J_{gem}$=11.4, $J_{H,P}$=$J_{5'b,4'}$=4.4, H-5'b); 3.95 (ddd, 1H, $J_{gem}$=11.4, $J_{H,P}$=5.6, $J_{5'a,4'}$=4.2, H-5'a); 4.30 (ddd, 1H, $J_{4',5'}$=4.4, 4.2, $J_{4',3'}$=2.7, H-4'); 4.46 (dd, 1H, $J_{3',2'}$=5.4, $J_{3',4'}$=2.7, H-3'); 4.75 (dd, 1H, $J_{2',1'}$=7.1, $J_{2',3'}$=5.4, H-2'); 6.31 (d, 1H, $J_{1',2'}$=7.1, H-1'); 7.46 (m, 1H, H-p-Ph); 7.54 (m, 2H, H-m-Ph); 7.56 (m, 2H, H-o-Ph); 7.58 (s, 1H, H-6); 8.18 (s, 1H, H-2). $^{13}$C NMR (125.7 MHz, D$_2$O, ref$_{dioxane}$=69.3 ppm): 66.53 (d, $J_{C,P}$=5, CH$_2$-5'); 73.61 (CH-3'); 76.15 (CH-2'); 86.94 (d, $J_{C,P}$=9, CH-4'); 88.22 (CH-1'); 103.97 (C-4a); 121.38 (C-5); 122.79 (CH-6); 130.44 (CH-p-Ph); 131.72 (CH-o-Ph); 131.91 (CH-m-Ph); 136.31 (C-i-Ph); 153.35 (C-7a); 154.40 (CH-2); 160.15 (C-4). $^{31}$P ($^1$H dec.) NMR (202.4 MHz, D$_2$O, ref$_{H3PO4}$=0 ppm): 4.64. MS (ESI) m/z 445 (M+H), 467 (M+Na). HRMS (ESI) for C$_{17}$H$_{19}$N$_4$NaO$_7$P: [M+H] calcd: 445.0884; found: 445.0880.

Example 36

4-Amino-5-(4-fluorophenyl)-7-(β-D-ribofuranosyl)-7H-pyrrolo[2,3-d]pyrimidine 5'-O-monophosphate sodium salt (14b)

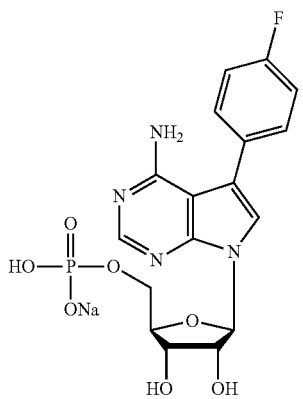

Title compound was prepared by following the procedure in Example 35, Step 2. White solid. Yield 47%. $^1$H NMR (500 MHz, D$_2$O, ref$_{dioxane}$=3.75 ppm): 3.90 (dt, 1H, $J_{gem}$=11.4, $J_{H,P}$=$J_{5'b,4'}$=4.1, H-5'b); 3.94 (ddd, 1H, $J_{gem}$=11.4, $J_{H,P}$=5.6, $J_{5'a,4'}$=4.1, H-5'a); 4.30 (tdd, 1H, $J_{4',5'}$=4.1, $J_{4',3'}$=2.7, $J_{H,P}$=1.1, H-4'); 4.46 (dd, 1H, $J_{3',2'}$=5.4, $J_{3',4'}$=2.7, H-3'); 4.74 (dd, 1H, $J_{2',1'}$=7.2, $J_{2',3'}$=5.4, H-2'); 6.30 (d, 1H, $J_{1',2'}$=7.2, H-1'); 7.25 (m, 2H, H-m-C$_6$H$_4$F); 7.54 (m, 2H, H-o-C$_6$H$_4$F); 7.57 (s, 1H, H-6); 8.18 (s, 1H, H-2). $^{13}$C NMR (125.7 MHz, D$_2$O, ref$_{dioxane}$=69.3 ppm): 66.52 (d, $J_{C,P}$=4, CH$_2$-5'); 73.61 (CH-3'); 76.17 (CH-2'); 86.97 (d, $J_{C,P}$=9, CH-4'); 88.20 (CH-1'); 104.07 (C-4a); 118.55 (d, $J_{C,P}$=22, CH-m-C$_6$H$_4$F); 120.44 (C-5); 122.89 (CH-6); 132.35 (d, $J_{C,P}$=3, C-i-C$_6$H$_4$F); 133.55 (d, $J_{C,P}$=8, CH-o-C$_6$H$_4$F); 153.31 (C-7a); 154.45 (CH-2); 160.18 (C-4); 165.00 (d, $J_{C,P}$=245, C-p-C$_6$H$_4$F). $^{31}$P ($^1$H dec.) NMR (202.4 MHz, D$_2$O, ref$_{H3PO4}$=0 ppm): 4.65. MS (ESI, negative mode) m/z 439 (M−Na), 461 (M−H). HRMS (ESI, negative mode) for C$_{17}$H$_{17}$FN$_4$O$_7$P [M−Na] calcd: 439.0813; found: 439.0828; for C$_{17}$H$_{16}$FN$_4$NaO$_7$P [M−H] calcd: 461.0633; found: 461.0647.

Example 37

4-Amino-5-(furan-2-yl)-7-(β-D-ribofuranosyl)-7H-pyrrolo[2,3-d]pyrimidine 5'-O-monophosphate sodium salt (14c)

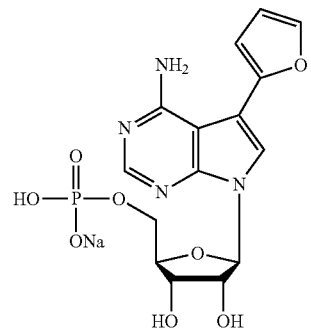

Title compound was prepared by following the procedure in Example 35, Step 2. Tan cotton. Yield 34%. $^1$H NMR (500 MHz, D$_2$O, ref$_{dioxane}$=3.75 ppm): 3.94 (ddd, 1H, $J_{gem}$=11.4, $J_{H,P}$=4.0, $J_{5'b,4'}$=2.6, H-5'b); 3.98 (ddd, 1H, $J_{gem}$=11.4, $J_{H,P}$=5.2, $J_{5'a,4'}$=3.7, H-5'a); 4.31 (m, 1H, $J_{4',5'}$=3.7, 2.6, $J_{4',3'}$=2.9, $J_{H,P}$=1.1, H-4'); 4.47 (dd, 1H, $J_{3',2'}$=5.3, $J_{3',4'}$=2.9, H-3'); 4.73 (dd, 1H, $J_{2',1'}$=6.9, $J_{2',3'}$=5.3, H-2'); 6.28 (d, 1H, $J_{1',2'}$=6.9, H-1'); 6.61 (dd, 1H, $J_{4,3}$=3.3, $J_{4,5}$=1.9, H-4-furyl); 6.78 (dd, 1H, $J_{3,4}$=3.3, $J_{3,5}$=0.7, H-3-furyl); 7.63 (dd, 1H, $J_{5,4}$=1.9, $J_{5,3}$=0.7, H-5-furyl); 7.87 (s, 1H, H-6); 8.14 (s, 1H, H-2). $^{13}$C NMR (125.7 MHz, D$_2$O, ref$_{dioxane}$=69.3 ppm): 66.52 (d, $J_{C,P}$=5, CH$_2$-5'); 73.65 (CH-3'); 76.41 (CH-2'); 87.09 (d, $J_{C,P}$=9, CH-4'); 88.38 (CH-1); 102.81 (C-4a); 109.23 (CH-3-furyl); 111.01 (C-5); 114.78 (CH-4-furyl); 122.30 (CH-6); 144.85 (CH-5-furyl); 150.56 (C-2-furyl); 153.34 (C-7a); 154.57 (CH-2); 160.08 (C-4). $^{31}$P ($^1$H dec.) NMR (202.4 MHz, D$_2$O, ref$_{H3PO4}$=0 ppm): 4.37. MS (ESI, negative mode) m/z 411 (M−Na), 433 (M−H). HRMS (ESI, negative mode) for C$_{15}$H$_{16}$N$_4$O$_8$P [M−Na] calcd: 411.0700; found: 411.0702.

Example 38

4-Amino-7-(β-D-ribofuranosyl)-5-(thiophen-2-yl)-7H-pyrrolo[2,3-d]pyrimidine 5'-O-monophosphate sodium salt (14d)

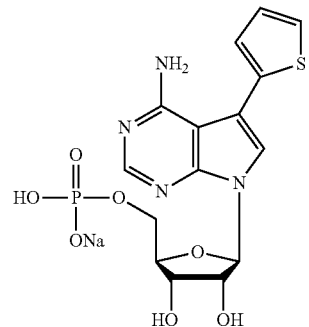

Title compound was prepared by following the procedure in Example 35, Step 2. Tan cotton. Yield 51%. $^1$H NMR (500 MHz, D$_2$O, ref$_{dioxane}$=3.75 ppm): 3.91 (dt, 1H, J$_{gem}$=11.4, J$_{H,P}$=J$_{5'b,4'}$=3.3, H-5''b); 3.95 (ddd, 1H, J$_{gem}$=11.4, J$_{H,P}$=5.4, J$_{5'a,4'}$=4.2, H-5'a); 4.30 (ddd, 1H, J$_{4',5'}$=4.2, 3.3, J$_{4',3'}$=2.8, H-4'); 4.45 (dd, 1H, J$_{3',2'}$=5.4, J$_{3',4'}$=2.8, H-3'); 4.72 (dd, 1H, J$_{2',1'}$=7.0, J$_{2',3'}$=5.4, H-2'); 6.28 (d, 1H, J$_{1',2'}$=7.0, H-1'); 7.21 (dd, 1H, J$_{4,5}$=4.8, J$_{4,3}$=3.5, H-4-thienyl); 7.22 (dd, 1H, J$_{3,4}$=3.5, J$_{3,5}$=1.5, H-3-thienyl); 7.51 (dd, 1H, J$_{5,4}$=4.8, J$_{5,3}$=1.5, H-5-thienyl); 7.65 (s, 1H, H-6); 8.17 (s, 1H, H-2). $^{13}$C NMR (125.7 MHz, D$_2$O, ref$_{dioxane}$=69.3 ppm): 66.53 (d, J$_{C,P}$=5, CH$_2$-5'); 73.57 (CH-3'); 76.18 (CH-2'); 86.97 (d, J$_{C,P}$=9, CH-4'); 88.22 (CH-1'); 104.21 (C-4a); 113.44 (C-5); 124.02 (CH-6); 129.30 (CH-5-thienyl); 130.25 (CH-3-thienyl); 130.93 (CH-4-thienyl); 137.08 (C-2-thienyl); 153.12 (C-7a); 154.63 (CH-2); 160.11 (C-4). $^{31}$P ($^1$H dec.) NMR (202.4 MHz, D$_2$O, ref$_{H3PO4}$=0 ppm): 4.57. MS (ESI, negative mode) m/z 427 (M−Na), 449 (M−H). HRMS (ESI, negative mode) for C$_{15}$H$_{16}$SN$_4$O$_7$P [M−Na] calcd: 427.0472; found: 427.0473.

Example 39

4-Amino-5-(furan-3-yl)-7-(β-D-ribofuranosyl)-7H-pyrrolo[2,3-d]pyrimidine 5'-O-monophosphate sodium salt (14e)

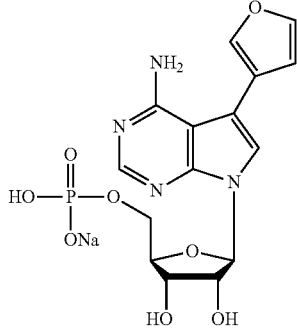

Title compound was prepared by following the procedure in Example 35, Step 2. White cotton. Yield 45%. $^1$H NMR (500 MHz, D$_2$O, ref$_{dioxane}$=3.75 ppm): 3.91 (dt, 1H, J$_{gem}$=11.3, J$_{H,P}$=J$_{5'b,4'}$=4.1, H-5'b); 3.95 (ddd, 1H, J$_{gem}$=11.3, J$_{H,P}$=5.2, J$_{5'a,4'}$=4.1, H-5'a); 4.30 (td, 1H, J$_{4',5'}$=4.1, J$_{4',3'}$=2.7, H-4'); 4.46 (dd, 1H, J$_{3',2'}$=5.6, J$_{3',4'}$=2.7, H-3'); 4.73 (dd, 1H, J$_{2',1'}$=7.0, J$_{2',3'}$=5.6, H-2'); 6.28 (d, 1H, J$_{1',2'}$=7.0, H-1'); 6.73 (dd, 1H, J$_{4',5'}$=1.8, J$_{4,2}$=0.9, H-4-furyl); 7.60 (s, 1H, H-6); 7.66 (dd, 1H, J$_{5,4}$=1.8, J$_{5,2}$=1.6, H-5-furyl); 7.75 (dd, 1H, J$_{2,5}$=1.6, J$_{2,4}$=0.9, H-2-furyl); 8.17 (s, 1H, H-2). $^{13}$C NMR (151 MHz, D$_2$O, ref$_{dioxane}$=69.3 ppm): 66.51 (d, J$_{C,P}$=4, CH$_2$-5'); 73.66 (CH-3'); 76.19 (CH-2'); 87.04 (d, J$_{C,P}$=9, CH-4'); 88.14 (CH-1'); 104.48 (C-4a); 111.30 (C-5); 114.25 (CH-4-furyl); 120.37 (C-3-furyl); 122.96 (CH-6); 143.22 (CH-2-furyl); 147.02 (CH-5-furyl); 153.24 (C-7a); 154.46 (CH-2); 160.30 (C-4). $^{31}$P ($^1$H dec.) NMR (202.4 MHz, D$_2$O, ref$_{H3PO4}$=0 ppm): 4.55. MS (ESI, negative mode) m/z 411 (M−Na), 433 (M−H). HRMS (ESI, negative mode) for C$_{15}$H$_{16}$N$_4$O$_8$P [M−Na] calcd: 411.0700; found: 411.0706; for C$_{15}$H$_{15}$N$_4$O$_8$PNa [M−H] calcd: 433.0520; found: 411.0526.

Example 40

4-Amino-7-(β-D-ribofuranosyl)-5-(thiophen-3-yl)-7H-pyrrolo[2,3-d]pyrimidine 5'-O-monophosphate sodium salt (14f)

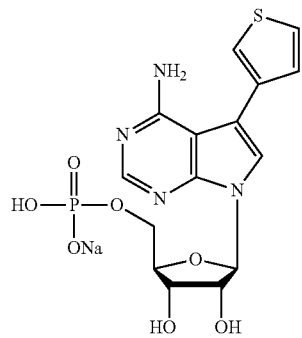

Title compound was prepared by following the procedure in Example 35, Step 2. Pink solid. Yield 47%. $^1$H NMR (600 MHz, D$_2$O, ref$_{dioxane}$=3.75 ppm): 3.91 (dt, 1H, J$_{gem}$=11.4, J$_{H,P}$=J$_{5'b,4'}$=4.1, H-5'b); 3.95 (ddd, 1H, J$_{gem}$=11.4, J$_{H,P}$=5.5, J$_{5'a,4'}$=4.0, H-5'a); 4.30 (m, 1H, J$_{4',5'}$=4.1, 4.0, J$_{4',3'}$=2.7, J$_{H,P}$=1.2, H-4'); 4.46 (dd, 1H, J$_{3',2'}$=5.4, J$_{3',4'}$=2.7, H-3'); 4.74 (dd, 1H, J$_{2',1'}$=7.1, J$_{2',3'}$=5.4, H-2'); 6.29 (d, 1H, J$_{1',2'}$=7.1, H-1'); 7.32 (dd, 1H, J$_{4,5}$=4.9, J$_{4,2}$=1.4, H-4-thienyl); 7.51 (dd, 1H, J$_{2,5}$=2.9, J$_{2,4}$=1.4, H-2-thienyl); 7.608 (dd, 1H, J$_{5,4}$=4.9, J$_{5,2}$=2.9, H-5-thienyl); 7.612 (s, 1H, H-6); 8.16 (s, 1H, H-2). $^{13}$C NMR (151 MHz, D$_2$O, ref$_{dioxane}$=69.3 ppm): 66.55 (d, J$_{C,P}$=5, CH$_2$-5'); 73.66 (CH-3'); 76.21 (CH-2'); 87.00 (d, J$_{C,P}$=9, CH-4'); 88.18 (CH-1'); 104.18 (C-4a); 115.99 (C-5); 122.83 (CH-6); 125.98 (CH-2-thienyl); 130.186 (CH-5-thienyl); 131.33 (CH-4-thienyl); 136.34 (C-3-thienyl); 153.11 (C-7a); 154.39 (CH-2); 160.19 (C-4). $^{31}$P ($^1$H dec.) NMR (202.4 MHz, D$_2$O, ref$_{H3PO4}$=0 ppm): 4.46. MS (ESI, negative mode) m/z 427 (M−Na), 449 (M−H). HRMS (ESI, negative mode) for C$_{15}$H$_{16}$SN$_4$O$_7$P: [M−Na] calcd: 427.0472; found: 427.0474; for C$_{15}$H$_{15}$SN$_4$O$_7$PNa: [M−H] calcd: 449.0291; found: 449.0295.

The invention has been described with reference to various specific and preferred embodiments and techniques. However, it should be understood that many variations and modifications may be made while remaining within the spirit and scope of the invention.

What is claimed is:

1. A compound of formula I:

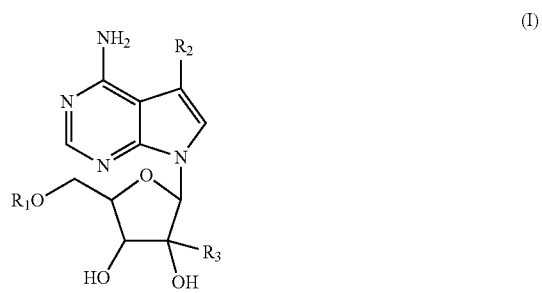

wherein:
R$_1$ is hydrogen, mono-, di-, or tri-phosphate;
R$_2$ is furan-2-yl, 1H-pyrrol-2-yl, 1H-pyrrol-3-yl, 1H-pyrazol-4-yl, 1H-pyrazol-3-yl, 1H-1,2,3-triazol-4- yl, thiazol-2-yl, 1H-imidazol-4-yl, 1H-imidazol-2-yl, thiophen-2-yl, furan-3-yl, thiophen-3-yl, or benzofuran-2-yl; and R$_3$ is hydrogen or alkyl; or a pharmaceutically acceptable salt thereof; or an optical isomer thereof; or a mixture of optical isomers.

2. The compound of claim 1, wherein R$_3$ is hydrogen; or a pharmaceutically acceptable salt thereof; or an optical isomer thereof; or a mixture of optical isomers.

3. The compound of claim 2, wherein R$_1$ is hydrogen; or a pharmaceutically acceptable salt thereof; or an optical isomer thereof; or a mixture of optical isomers.

4. The compound of claim 1, wherein R$_3$ is alkyl; or a pharmaceutically acceptable salt thereof; or an optical isomer thereof; or a mixture of optical isomers.

5. The compound of claim 4, wherein R$_1$ is hydrogen and R$_3$ is (C$_1$-C$_4$) alkyl; or a pharmaceutically acceptable salt thereof; or an optical isomer thereof; or a mixture of optical isomers.

6. A pharmaceutical composition comprising a therapeutically effective amount of the compound according to claim 1 and one or more pharmaceutically acceptable carriers.

7. The pharmaceutical composition according to claim 6, further comprising a second therapeutic agent selected from the group consisting of antracyclines, DNA intercalators, alkylating agents, hormonal agents, LHRH agonists and antagonists, aromatase inhibitors, antiandrogens, chemoprevention agents, cell-cycle chemopreventative agents, antineoplasts, antimitotic agents, plant alkaloids, topoisomerase I inhibitors, topoisomerase II inhibitors, proteosomes inhibitors, nucleoside analogues, cytokines, growth factors, antiangiogenic factors, and one or more pharmaceutically acceptable carriers.

8. A method of inhibiting tumor/cancer growth in a subject comprising administering to the subject a therapeutically effective amount of the compound according to claim 1.

9. A method of inhibiting cell proliferation in tumor/cancer cells in a subject comprising administering to the subject a therapeutically effective amount of the compound according to claim 1.

10. A method of treating a cellular proliferation disease in a subject comprising administering to the subject a therapeutically effective amount of the compound according to claim 1.

11. A method of treating a neoplastic disease in a subject comprising administering to the subject a therapeutically effective amount of the compound according to claim 1.

12. A method of treating a tumor or cancer in a subject comprising administering to the subject a therapeutically effective amount of the compound according to claim 1.

13. A compound selected from the following compounds:

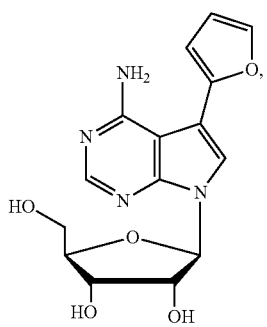

-continued

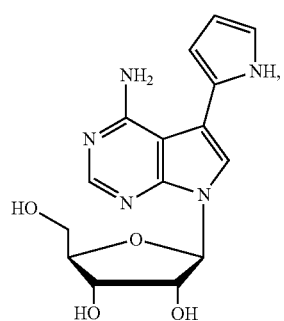

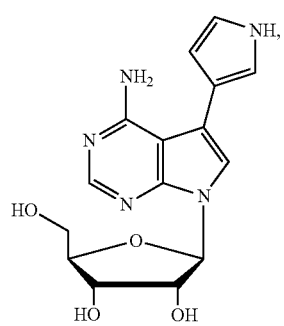

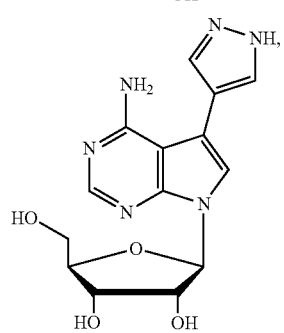

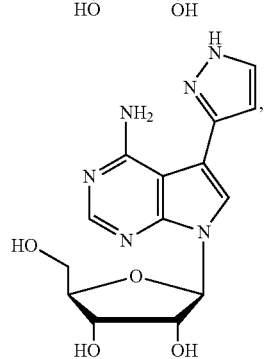

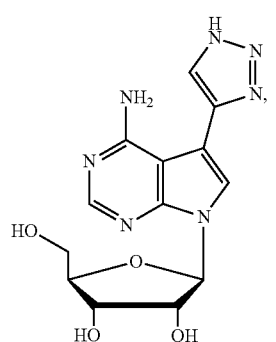

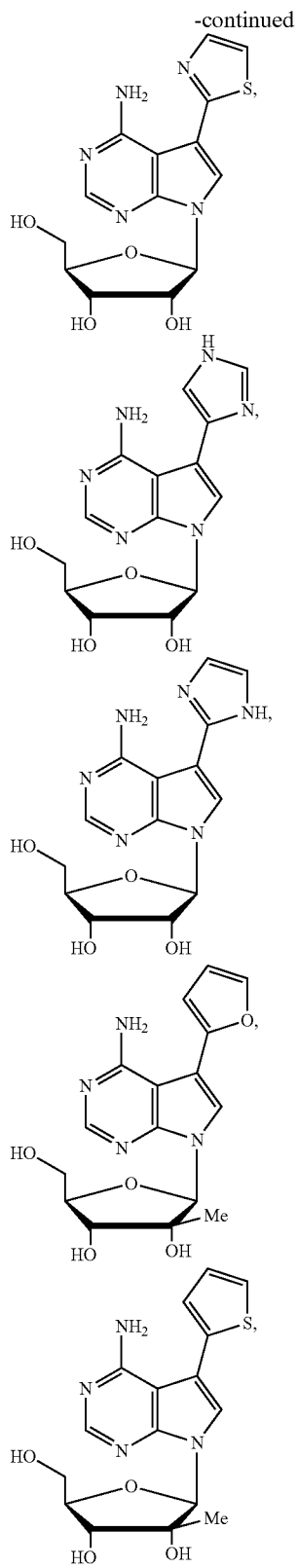

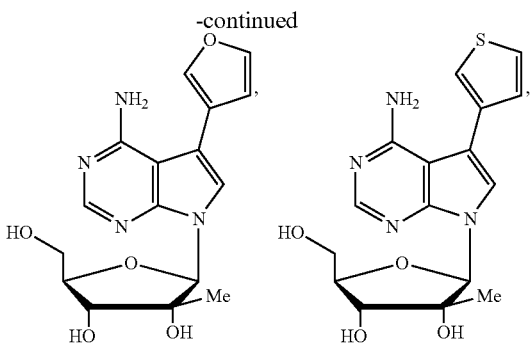

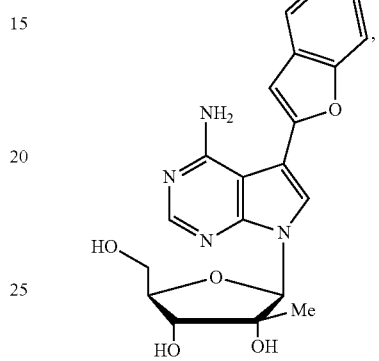

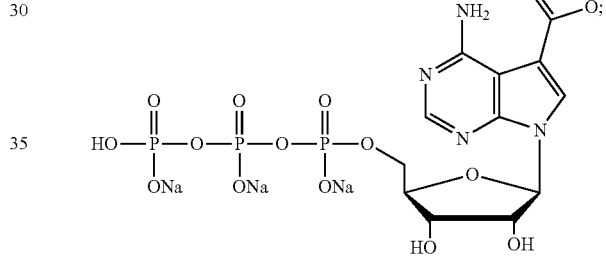

or a pharmaceutically acceptable salt thereof; or an optical isomer thereof; or a mixture of optical isomers.

14. A pharmaceutical composition comprising a therapeutically effective amount of the compound according to claim 13 and one or more pharmaceutically acceptable carriers.

15. The pharmaceutical composition according to claim 14, further comprising a second therapeutic agent selected from the group consisting of antracyclines, DNA intercalators, alkylating agents, hormonal agents, LHRH agonists and antagonists, aromatase inhibitors, antiandrogens, chemoprevention agents, cell-cycle chemopreventative agents, antineoplasts, antimitotic agents, plant alkaloids, topoisomerase I inhibitors, topoisomerase II inhibitors, proteosomes inhibitors, nucleoside analogues, cytokines, growth factors, anti-angiogenic factors, and one or more pharmaceutically acceptable carriers.

* * * * *